US006255315B1

(12) United States Patent
Patane et al.

(10) Patent No.: US 6,255,315 B1
(45) Date of Patent: Jul. 3, 2001

(54) ALPHA 1A ADRENERGIC RECEPTOR ANTAGONISTS

(75) Inventors: Michael A. Patane, Harleysville; Harold G. Selnick, Ambler; Mark G. Bock, Hatfield, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/458,169

(22) Filed: Dec. 9, 1999

Related U.S. Application Data

(62) Division of application No. 09/099,031, filed on Jun. 17, 1998, now Pat. No. 6,037,354.
(60) Provisional application No. 60/049,921, filed on Jun. 18, 1997.

(51) Int. Cl.[7] ............... A61K 31/513; C07D 401/14; C07D 239/32
(52) U.S. Cl. ............ 514/274; 544/330; 544/331; 544/332
(58) Field of Search ............... 544/330, 331, 544/332; 514/274

(56) References Cited

U.S. PATENT DOCUMENTS

| 4,049,821 | 9/1977 | Funderburk, Jr. ............ 424/274 |
| 4,109,005 | 8/1978 | Lunsford et al. ............ 424/274 |
| 4,226,612 | 10/1980 | Pilgram ............... 71/88 |
| 4,250,318 | 2/1981 | Dostert et al. ............ 548/229 |
| 4,254,135 | 3/1981 | Walsh et al. ............ 424/274 |
| 4,505,859 | 3/1985 | Poindexter ............ 260/453 P |
| 4,661,491 | 4/1987 | Regnier ............ 514/260 |
| 4,679,371 | 7/1987 | Atwal ............ 544/316 |
| 4,847,379 | 7/1989 | Atwal ............ 544/585 |
| 4,855,301 | 8/1989 | Atwal et al. ............ 514/274 |
| 4,882,431 | 11/1989 | Ishimitsu et al. ............ 540/603 |
| 5,023,338 | 6/1991 | Ocain ............ 548/336 |
| 5,124,457 | 6/1992 | Ungemach et al. ............ 546/196 |
| 5,202,330 | 4/1993 | Atwal et al. ............ 514/269 |
| 5,374,637 | 12/1994 | Van Daele et al. ............ 514/320 |
| 5,547,950 | 8/1996 | Hutchinson et al. ............ 514/252 |
| 5,565,571 | 10/1996 | Barbachyn et al. ............ 546/144 |
| 5,668,286 | 9/1997 | Yamada et al. ............ 546/209 |
| 5,719,154 | 2/1998 | Tucker et al. ............ 514/252 |

FOREIGN PATENT DOCUMENTS

| 0 234 830 | 9/1987 | (EP) . |
| 0 236 902 | 9/1987 | (EP) . |
| 0 628 551 | 12/1994 | (EP) . |
| 1 329 617 | 5/1963 | (FR) . |
| 2 092 585 | 8/1982 | (GB) . |
| 2 165 237 | 4/1986 | (GB) . |
| 2 092 577 | 8/1992 | (GB) . |
| 90/06118 | 6/1990 | (WO) . |
| 92/00073 | 1/1992 | (WO) . |
| 92/16213 | 10/1992 | (WO) . |
| 94/08040 | 4/1994 | (WO) . |
| 94/10989 | 5/1994 | (WO) . |
| 94/22829 | 10/1994 | (WO) . |
| 95/25106 | 9/1995 | (WO) . |
| 96/14846 | 5/1996 | (WO) . |
| 97/17969 | 5/1997 | (WO) . |
| 97/27188 | 7/1997 | (WO) . |
| 97/30995 | 8/1997 | (WO) . |
| 97/42956 | 11/1997 | (WO) . |

OTHER PUBLICATIONS

K.S. Atwal et al., "Substituted 1,4–Dihydropyrimidines. 3 Synthesis of Selectively Functionalized 2–Hetero–1,4–dihydropyrimidines", J. Org.Chem., 54(25), 5898–907 (1989).

Chemical Abstracts No.58:11360a: R. Merten et al., "Reaction of acylated aldehyde animals with unsaturated hydrocarbons", Angew. Chem. 74,866–71 (1962).

Derwent CPI Abstracts No. 90–041598, "Remedy for Dysuria", Abstract of JP01–319418, Nippon Chemifar (1990).

Derwent CPI Abstracts No. 87–027600, "New 1,3–oxazolidin–2–one derivatives", Abstract of JP61–286375, Nippon Chemifar (1987).

W.C. Wong et al., "Design and Synthesis of Dihydropyrimidines as Alpha 1a Adrenoceptor Selective Antagonists", Abstract No. MEDI 064, 215th ACS National Meeting, Dallas, TX (Mar. 29–Apr. 2, 1998).

B. Lagu et al., "Design Synthesis and Evaluation of Dihydropyrimidinones as Alpha 1a Selective Antagonists", Abstract No, MEDI 065, 215th ACS National Meeting, Dallas, TX (Mar. 29–Apr. 2, 1998).

D. Nagarathnam et al., "Design, Synthesis and Evaluation of Dihydropyrimidinones as Alpha 1a Selective Antagonists: 6. Synthesis and Structure–Activity Relationship of SNAP 6553 and Analogs", Abstract No. MEDI 066, 215th ACS National Meeting, Dallas, TX (Mar. 29–Apr. 2, 1998).

(List continued on next page.)

*Primary Examiner*—Mukund J. Shah
*Assistant Examiner*—Deepak R. Rao
(74) *Attorney, Agent, or Firm*—Kenneth R. Walton; Melvin Winokur

(57) ABSTRACT

This invention relates to certain novel compounds and derivatives thereof, their synthesis, and their use as alpha 1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha relductase inhibitory compound, such that both acute and chronic relief from the effects of benign prostatic hyperplasia are achieved.

30 Claims, No Drawings

OTHER PUBLICATIONS

M.R. Marzabadi et al, "Design, Synthesis and Evaluation of Dihydropyrimidinones and Dihydropyrimidines as Alpha 1a Selective Antagonists: Modification of the Diarylpiperidine Moiety", Abstract No. MEDI 067, 215th ACS National Meeting, Dallas, TX (Mar. 29–Apr. 2, 1998).

G.C. Rovnyak et al., "Dihydropyrimidine Calcium Channel Blockers. 4. Basic 3–Substituted–4–aryl–1, 4 dihydropyrimidine–5–carboxylic Acid Esters. Potent Antihypertensive Agents", J. Med. Chem, 35 (17), 3254–63 (1992).

K.S. Atwal et al., "Dihydropyrimidine Calcium Channel Blockers. 3 3–Carbamoyl–4–1,2,3, 4–tetrahydro–6methyl–5pyrimidinecarboxylic Acid Esters as Orally Effective Antihypertensive Agents" J. Med. Chem, 34(2), 806–11 (1991).

K.S. Atwal et al., "Dihydropyrimidine Calcium Channel Blockers, 2. 3–Substituted–4–aryl–1, 4–dihydro–6–methyl–5–pyrimidinecarboxylic Acid Esters as Potent Mimics of Dihydropyridines" J. Med. Chem., 33(9), 2629–35 (1990).

ALPHA 1A ADRENERGIC RECEPTOR ANTAGONISTS

This application is a division of U.S. Ser. No. 09/099,031, filed Jun. 17, 1998 now U.S. Pat. No. 6,037,354, which claims the benefit of U.S. Provisional Application Ser. No. 60/049,921, filed Jun. 18, 1997.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha idrenergic receptors, the reader's attention is directed to Robert R. Ruffolo, Jr., α-*Adrenoreceptors: Molecular Biology, Biochemistry and Pharmacology*, (Progress in Basic and Clinical Pharmacology series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1 d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc's product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the alpha$_1$ subtype was reported. In addition, in WO 92/161213, combinations of 5α-reductase inhibitory compounds and alpha1-adrenergic receptor blockers (terazosin, doxazosin, prazosin, bunazosin, indoramin, alfuzosin) were disclosed. However, no information as to the alpha 1, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published Apr. 14, 1994 and WO94/10989, published May 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH. The instant patent disclosure discloses novel compounds which selectively bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

It has now been found that the compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc. The compounds of the present invention have the structure:

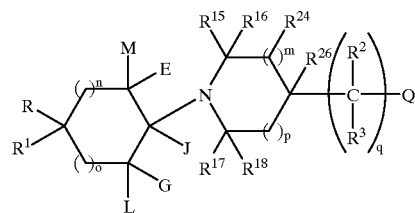

wherein Q is selected from

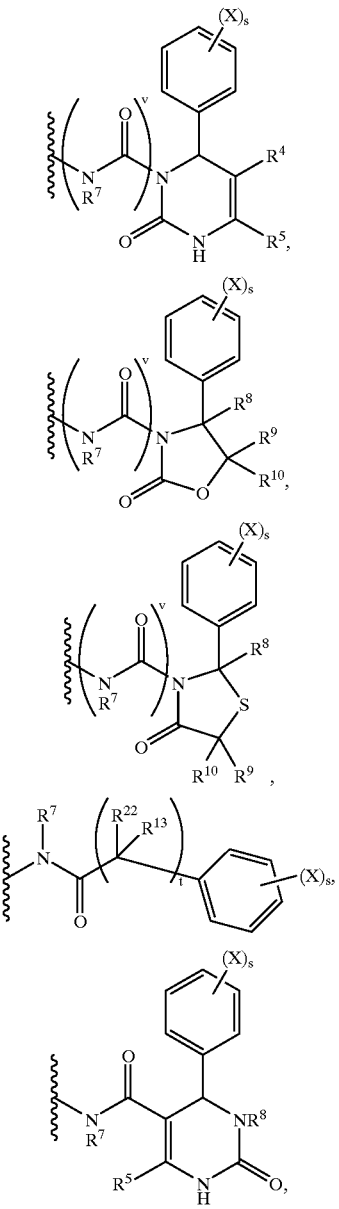

-continued

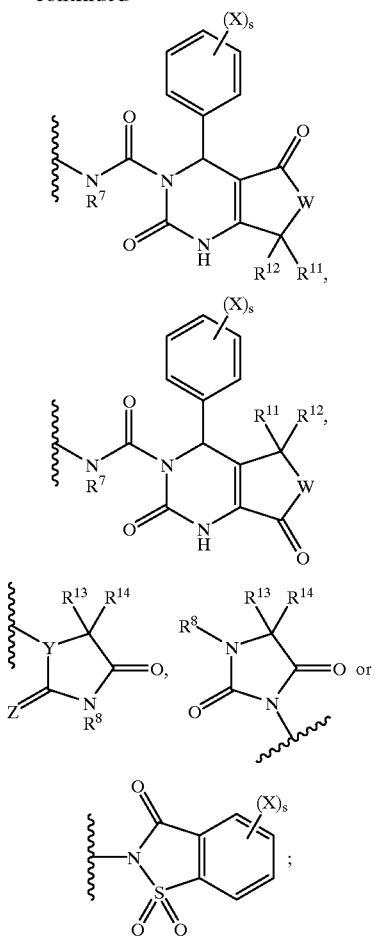

E, G, L and M are each independently selected from hydrogen, $C_{1-8}$ alkyl, $C_{3-8}$ cycloalkyl, $(CH_2)_{0-4}OR^6$, $(CH_2)_{0-4}N(R^{19})_2$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$;

J is selected from hydrogen, $C_{1-8}$ alkyl, $C_{3-8}$ cycloalkyl, $(CH_2)_{1-4}OR^6$, $(CH_2)_{1-4}N(R^{19})_2$, $(CH_2)_{1-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$, or $(CH_2)_{0-4}SO_2N(R^{19})_2$;

$R^1$ is selected from unsubstituted, mono- or poly-substituted phenyl wherein the substituents on the phenyl are independently selected from halogen, $CF_3$, cyano, nitro, $OR^6$, $N(R^{19})2$, $NR^{19}COR^{20}$, $NR^{19}CON(R^{20})_2$, $NR^{19}SO_2R^6$, $NR^{19}SO_2N(R^{20})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, pyridyl N-oxide (N→O) pyrazinyl, thienyl, thiazolyl, furanyl, quinazolinyl or naphthyl wherein the substituents on the pyridyl, pyrazinyl, thienyl, thiazolyl, furanyl, quinazolinyl, or naphthyl are independently selected from $CF_3$, cyano, nitro, $N(R^{19})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

R is selected from hydrogen, cyano, $OR^6$, $CO_2R^{19}$, $CON(R^{19})_2$, tetrazole, isooxadiazole, unsubstituted, mono- or poly-substituted phenyl wherein the substituents on the phenyl are independently selected from halogen, cyano, nitro, $OR^6$, $(CH_2)_{0-4}CO_2R^{19}$, $(CH_2)_{0-4}CON(R^{19})_2$, $N(R^{19})_2$, $NR^{19}COR^6$, $NR^{19}CON(R^{20})_2$, $NR^{19}SO_2R^6$, $NR^{19}SO_2N(R^{20})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, thienyl, furanyl or niphthyl wherein the substituents on the pyridyl, thienyl, furanyl or naphthyl are independently selected from $CF_3$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

$R^2$, $R^3$ and $R^7$ are each independently selected from hydrogen, $C_{1-8}$ alkyl, $C_{4-8}$ cycloalkyl, $(CH_2)_{0-4}CO_2R^{19}$, $(CH_2)_{0-4}CON(R^{19})_2$, $(CH_2)_{0-4}COR^6$, $(CH_2)_{2-4}OR^6$, $(CH_2)_{1-4}CF_3$, $(CH_2)_{0-4}SO_2R^6$, $(CH_2)_{0-4}SO_2N(R^{19})_2$ or $(CH_2)_{1-4}CN$;

$R^4$ is selected from hydrogen, $(CH_2)_{0-4}COR^6$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$;

$R^5$, $R^8$, $R^{10}$, $R^{15}$, $R^{16}$, $R^{17}$ and $R^{18}$ are each independently selected from hydrogen, $C_{1-8}$ alkyl, $C_{3-8}$ cycloalkyl, $(CH_2)_{2-4}OR^6$ or $(CH_2)_{0-4}CF_3$;

$R^6$ is selected from hydrogen, $C_{1-8}$ alkyl, $C_{3-8}$ cycloalkyl or $(CH_2)_{0-4}CF_3$;

$R^9$ is selected from hydrogen, $C_{1-8}$ alkyl, $C_{3-8}$ cycloalkyl, $CO_2R^6$, $CON(R^6)_2$, $(CH_2)_{1-4}OR^6$ or $(CH_2)_{0-4}CF_3$;

$R^{11}$ and $R^{12}$ are each independently selected from hydrogen, $C_{1-8}$ alkyl or $C_{3-8}$ cycloalkyl;

$R^{13}$ and $R^{14}$ are each independently selected from hydrogen, $C_{1-8}$ alkyl, $C_{3-8}$ cycloalkyl, $(CH_2)_{1-4}OR^6$, $(CH_2)_{0-4}CF_3$, unsubstituted, mono- or poly-substituted phenyl wherein the substituents on the phenyl are independently selected from halogen, $CF_3$, cyano, nitro, $OR^6$, $(CH_2)_{0-4}CON(R^{19})_2$, $(CH_2)_{0-4}CO_2R^{19}$ or $C_{1-4}$ alkyl; or unsubstituted, mono- or poly-substituted: pyridyl, thienyl, furanyl or naphthyl wherein the substituents on the pyridyl, thienyl, furanyl or naphthyl are independently selected from $CF_3$, phenyl, $OR^6$, halogen, $C_{1-4}$ alkyl or $C_{3-8}$ cycloalkyl;

$R^{19}$ and $R^{20}$ are each independently selected from hydrogen, $C_{1-8}$ alkyl, $C_{3-8}$ cycloalkyl or $(CH_2)_{1-4}CF_3$;

$R^{22}$ is selected from hydrogen, $C_{1-8}$ alkyl, $C_{3-8}$ cycloalkyl, $(CH_2)_{0-4}OR^6$ or $(CH_2)_{0-4}CF_3$;

$R^{24}$ and $R^{26}$ are each independently selected from hydrogen or $OR^{28}$;

$R^{28}$ is selected from hydrogen, $C_{1-8}$ alkyl, $C_{3-8}$ cycloalkyl or $(CH_2)_{0-4}CF_3$;

W is O or $NR^{11}$; each X is independently selected from halogen, cyano, nitro, $C_{1-8}$ alkyl, $C_{3-8}$ cycloalkyl, $(CH_2)_{0-4}OR^6$ or $(CH_2)_{0-4}CF_3$;

Y is $C-R^6$ or N;

Z is hydrogen, oxygen or sulphur;

m, p and q are each independently an integer of from zero to two provided that when q is zero, $R^{26}$ is hydrogen;

n, o, s and t are each independently an integer of from zero to four;

v is an integer from zero to one;

and the pharmaceutically acceptable salts thereof.

A first embodiment of the invention is a compound having the structure

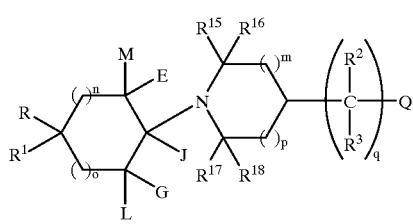

wherein $R^1$ is selected from unsubstituted, mono- or poly-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $(CH_2)_{1-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl, or naphthyl are independently selected from $CF_3$, cyano, nitro, $N(R^{19})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

$R^4$ is selected from $(CH_2)_{0-4}COR^6$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$; and $R^9$ is selected from hydrogen, $C_{1-8}$ alkyl, $C_{3-8}$ cycloalkyl, $(CH_2)_{2-4}OR^6$ or $(CH_2)_{0-4}CF_3$;

all other variables are as originally defined above; and the pharmaceutically acceptable salts thereof.

In a second embodiment of the invention is the compound of the formula

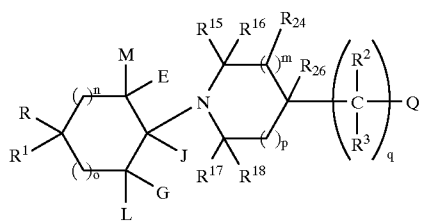

wherein

E, G, L, M and J are each independently selected from hydrogen, $C_{1-8}$ alkyl, $C_{3-8}$ cycloalkyl, or $(CH_2)_{0-4}CF_3$;

$R^1$ is selected from unsubstituted, mono-, di- or tri-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono-, di- or tri-substituted pyridyl, pyridyl N-oxide (N→O), pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

R is selected from hydrogen, cyano, $OR^6$, $CO_2R^{19}$, $CON(R^{19})_2$, tetrazole, isooxadiazole, unsubstituted, mono-, di- or tri-substituted phenyl wherein the substituents on the phenyl are independently selected from halogen, cyano, nitro, $OR^6$, $(CH_2)_{0-4}CO_2R^{19}$, $(CH_2)_{0-4}CON(R^{19})_2$, $N(R^{19})_2$, $NR^{19}COR^6$, $NR^{19}CON(R^{20})_2$, $NR^{19}SO_2R^6$, $NR^{19}SO_2N(R^{20})_2$, $(CH_2)_{0-4}SO_2N(R^{19})_2$, $(CH_2)_{0-4}SO_2R^6$ or $C_{1-4}$ alkyl; or unsubstit mono-, di- or tri-substituted pyridyl, thienyl, furanyl or naphthyl wherein the substituents on the pyridyl, thienyl, furanyl or naphthyl are independently selected from $CF_3$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

$R^2$, $R^3$ and $R^7$ are each independently selected from hydrogen, $C_{1-8}$ alkyl, $C_{4-8}$ cycloalkyl or $(CH_2)_{1-4}CF_3$;

$R^{13}$ and $R^{14}$ are each independently selected from hydrogen, $C_{1-8}$ alkyl, $C_{3-8}$ cycloalkyl, $(CH_2)_{1-4}OR^6$, $(CH_2)_{0-4}CF_3$, unsubstitited, mono-, di- or tri-substituted phenyl wherein the substituents on the phenyl are independently selected from halogen, $CF_3$, cyano, nitro, $OR^6$, $(CH_2)_{0-4}CON(R^{19})_2$, $(CH_2)_{0-4}CO_2R^{19}$ or $C_{1-4}$ alkyl; or unsubstituted, mono-, di- or tri-substituted: pyridyl, thienyl, furanyl or naphthyl wherein the substituents on the pyridyl, thienyl, furanyl or naphthyl are independently selected from $CF_3$, phenyl, $OR^6$, halogen, $C_{1-4}$ alkyl or $C_{3-8}$ cycloalkyl; and n and t are each independently an integer from zero to two;

and all other variables are as originally defined above;

and the pharmaceutically acceptable salts thereof.

In a third embodiment of the invention is the compound of formula

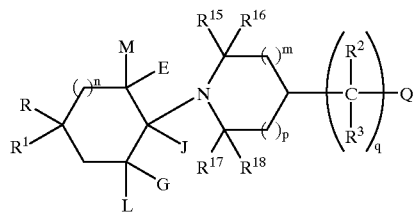

wherein $R^1$ is selected from unsubstituted, mono-, di- or tri-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl; and all other variables are as defined in the first embodiment;

and the pharmaceutically acceptable salts thereof.

In a first class of the invention is the compound selected from

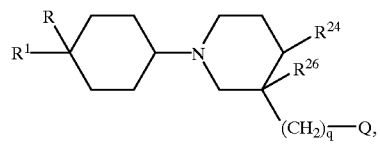

-continued

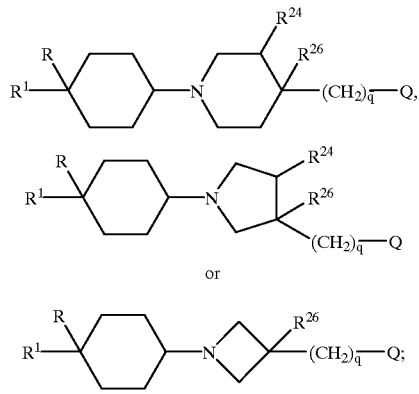

wherein Q is selected from

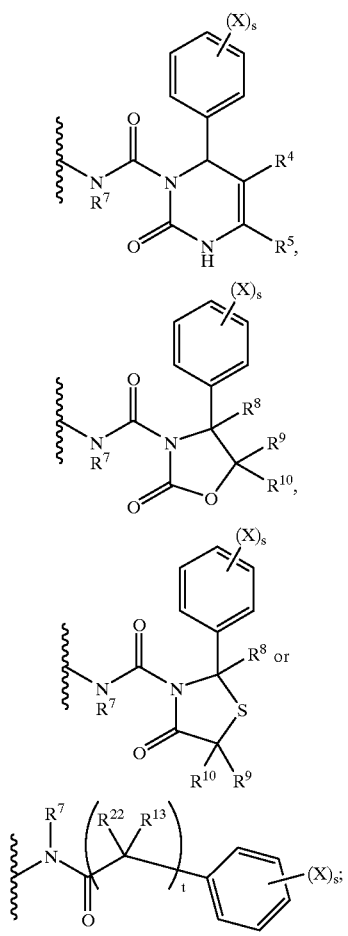

R¹ is selected from unsubstituted, mono-, di- or tri-substituted phenyl wherein the substituents on the phenyl are independently selected from halogen, $CF_3$, cyano, nitro, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl; or unsubstitu mono-, or di-substituted pyridyl or pyridyl N-oxide, wherein the substituents on the pyridyl or pyridyl N-oxide are independently selected from halogen, $CF_3$, cyano, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl;

R is selected from hydrogen, cyano, $OR^6$, $CO_2R^{19}$, $CON(R^{19})_2$, or unsubstituted, mono- or di-substituted phenyl wherein the substituents on the phenyl are independently selected from halogen, cyano, nitro, $OR^6$, $(CH_2)_{0-2}CO_2R^{19}$, $(CH_2)_{0-2}CON(R^{19})_2$ or $C_{1-4}$ alkyl;

$R^4$ is selected from hydrogen, $COR^6$, $CO_2R^{19}$, $SO_2R^6$ or $CON(R^{19})_2$;

$R^5$ is selected from hydrogen, $C_{1-6}$ alkyl, $C_{3-6}$ cycloalkyl, $(CH_2)_{0-3}OR^6$ or $(CH_2)_{0-3}CF_3$;

$R^6$ is selected from hydrogen, $C_{1-6}$ alkyl, $C_{3-6}$ cycloalkyl or $(CH_2)_{0-3}CF_3$;

$R^8$ and $R^{10}$ are each independently selected from hydrogen, $C_{1-6}$ alkyl, $C_{3-6}$ cycloalkyl, $(CH_2)_{2-4}OR^6$ or $(CH_2)_{0-3}CF_3$;

$R^9$ is selected from hydrogen, $C_{1-6}$ alkyl, $C_{3-6}$ cycloalkyl, $CO_2R^6$, $CON(R^6)2$, $(CH_2)_{1-4}OR^6$ or $(CH_2)_{0-3}CF_3$;

$R^{13}$ is selected from hydrogen, $C_{1-6}$ alkyl, $C_{3-6}$ cycloalkyl, $(CH_2)_{2-4}OR^6$, $(CH_2)_{0-2}CF_3$ or unsubstituted, mono- or di-substituted phenyl wherein the substituents on the phenyl are independently selected from halogen, $CF_3$, cyano, nitro, amino, $OR^6$, $CO_2R^{19}$ or $C_{1-4}$ alkyl;

$R^{19}$ is selected from hydrogen, $C_{1-6}$ alkyl, $C_{3-6}$ cycloalkyl or $(CH_2)_{1-3}CF_3$; and $R^{22}$ is selected from hydrogen, $C_{1-6}$ alkyl, $C_{3-6}$ cycloalkyl, $(CH_2)_{0-4}OR^6$ or $(CH_2)_{0-3}CF_3$;

$R^{24}$ and $R^{26}$ are each independently selected from hydrogen or $OR^{28}$, wherein $R^{28}$ is selected from hydrogen, $C_{1-6}$ alkyl, $C_{3-6}$ cycloalkyl or $(CH_2)_{1-3}CF_3$;

s is an integer from zero to three;

and all other variables are as defined above in the second embodiment;

and the pharmaceutically acceptable salts thereof.

In a second class of the invention is the compound selected from

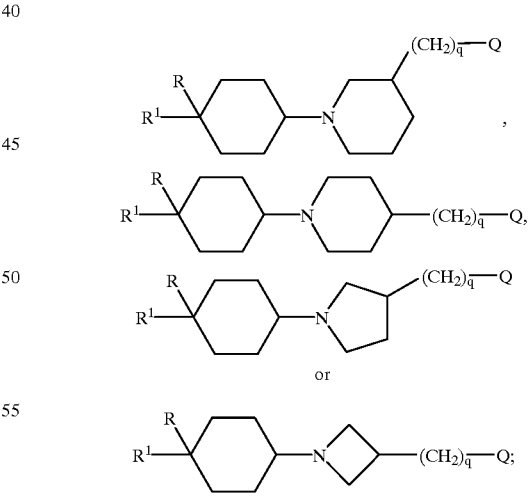

wherein $R^1$ is selected from unsubstituted, mono-, di- or tri-substituted phenyl wherein the substituents on the phenyl are independently selected from halogen, $CF_3$, cyano, nitro, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl; or unsubstitut mono-, or di-substituted pyridyl wherein the substitueiits on the pyridyl are independently selected from halogen, $CF_3$, cyano, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl;

$R^4$ is selected from $COR^6$, $CO_2R^{19}$, $SO_2R^6$, or $CON(R^{19})2$; and all other variables are as defined above in the third embodiment; and the pharmaceutically acceptable salts thereof.

In a first subclass of the invention is the compound selected from

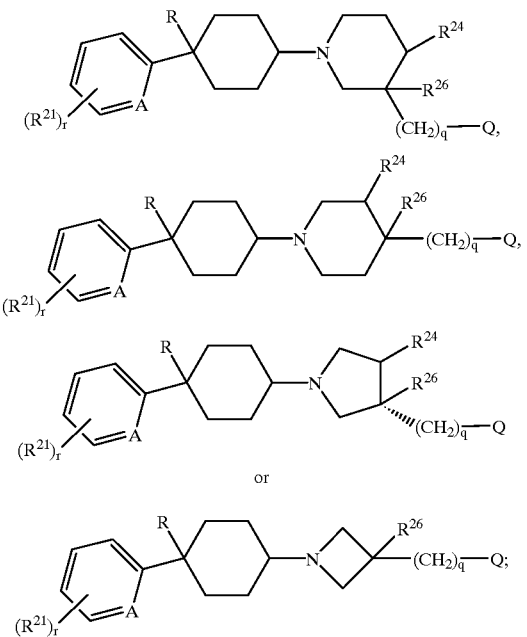

wherein Q is selected from

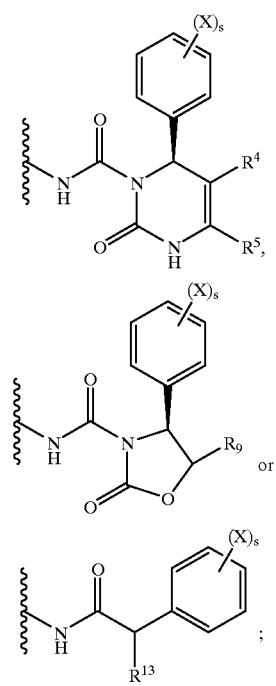

R is selected from hydrogen, $OR^6$ or cyano;

A is selected from $C-R^{21}$ or N or $N \rightarrow O$;

$R^{13}$ is selected from hydrogen, $C_{1-4}$ alkyl or unsubstituted, mono- or di-substituted phenyl wherein the substituents on the phenyl are independently selected from halogen, $CF_3$, cyano, nitro, amino, $OR^6$, $CO_2R^{19}$ or $C_{1-4}$ alkyl;

each X is a halogen;

each $R^{21}$ is independently selected from hydrogen, halogen, hydroxy, cyano, $OC_{1-4}$ alkyl, $OCF_3$, $OCH_2CF_3$, $CO_2-C_{1-4}$ alkyl, $CONH_2$, $SO_2NH_2$ or $SO_2C_{1-4}$ alkyl; and $R^{24}$ and $R^{26}$ are each independently selected from hydrogen or $OR^{28}$, wherein $R^{28}$ is selected from hydrogen, $C_{1-4}$ alkyl, or $(CH_2)_{0-2}CF_3$;

r is an integer from zero to two;

and all other variables are as defined in the first class above;

and the pharmaceutically acceptable salts thereof.

In a second subclass of the invention is the compound selected from

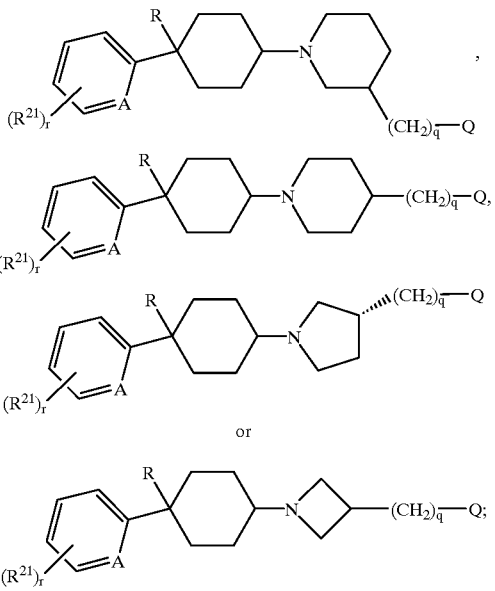

wherein A is selected from $C-R^{21}$ or N;

$R^{13}$ is selected from hydrogen, $C_{1-4}$ alkyl or unsubstituted, mono- or di-substituted phenyl wherein the substituents on the phenyl are independently selected from halogen, $CF_3$, cyano, nitro, amino, $OR^6$, $CO_2R^{19}$ or $C_{1-4}$ alkyl;

each X is a halogen;

each $R^{21}$ is independently selected from hydrogen, halogen, hydroxy, cyano, $OC_{1-4}$ alkyl, $OCF_3$, $OCH_2CF_3$, $CO_2-C_{1-4}$ alkyl, $CONH_2$, $SO_2NH_2$ or $SO_2C_{1-4}$ alkyl;

r is an integer from zero to two;

all other variables are as defined in the second class above; and the pharmaceutically acceptable salts thereof.

In a first illustration of the invention is the compound wherein Q is selected from

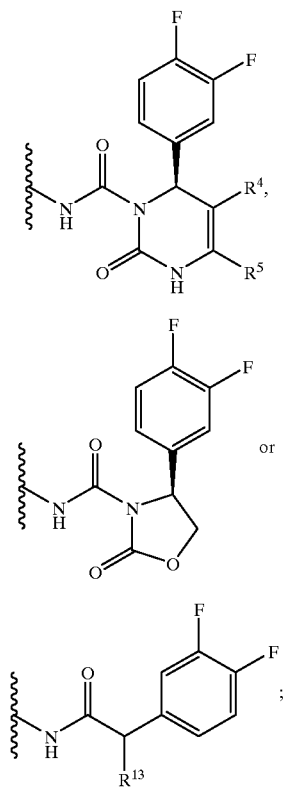

R is selected from hydrogen, hydroxy or cyano;

$R^4$ is $CO_2R^{19}$;

$R^5$ is $(CH_2)_{0-3}OR^6$;

q is an integer from zero to one;

and all other variables are as defined in the first subclass above;

and the pharmaceutically acceptable salts thereof; provided that the compound is not (4S)-trans-4-(3,4-difluorophenyl)-2-oxooxazolidine-3-carboxylic acid-[1-(4-hydroxy-4-pyridin-2-yl-cyclohexyl)-(3R)-pyrrolidin-3-yl]amide.

In a second illustration of the invention is the compound wherein Q is selected from

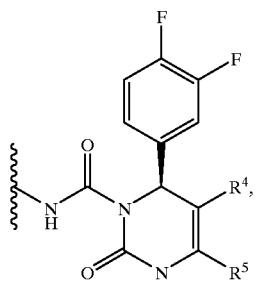

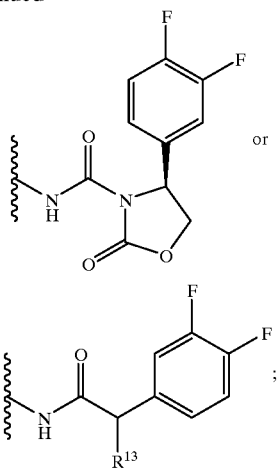

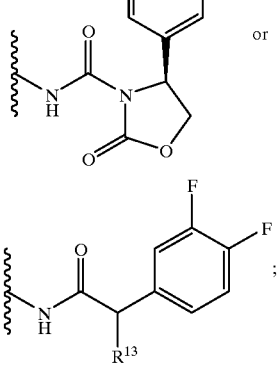

R is selected from hydrogen, hydroxy or cyano;

$R^4$ is $CO_2R^{19}$;

$R^5$ is $(CH_2)_{0-3}OR^6$;

q is an integer from zero to one;

and all other variables are as defined in the second subclass above;

and the pharmaceutically acceptable salts thereof; provided that the compound is not (4S)-trans-4-(3,4-difluorophenyl)-2-oxcoxazolidine-3-carboxylic acid-[1-(4-hydroxy-4-pyridin-2-yl-cyclohexyl)-(3R)-pyrrolidin-3-yl]amide.

In a third illustration of the invention is the compound wherein

R is H or OH;

Q is selected from

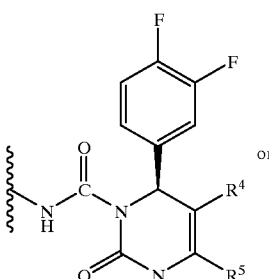

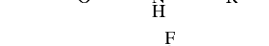

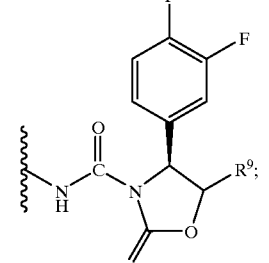

$R^4$ is H or $CO_2CH_3$;

$R^5$ is H, $CH_3$, or $CH_2OCH_3$;

$R^9$ is H, $CH_3$, cyclopropyl, $CONH_2$, $CH_2OH$, or $COOCH_3$;

q is an integer from zero to one; and all other variables are as defined in the first subclass above; and pharmaceutically acceptable salts thereof;

provided that the compound is not (4S)-trans-4-(3,4-difluorophenyl)- 2-oxooxazolidine-3-carboxylic acid-[1-(4-hydroxy-4-pyridin-2-yl-cyclohexyl)-(3R)-pyrrolidin-3-yl]amide hydrochloride.

One aspect of the invention is the compound having the formula:

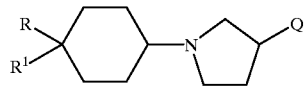

wherein

R is H or OH;

$R^1$ is suitably unsubstituted pyridyl, unsubstituted pyridyl N-oxide, unsubstituted phenyl, or mono- or poly-substituted phenyl; typically unsubstituted pyridyl, unsubstituted pyridyl N-oxide, unsubstituted phenyl, or mono- or di-substituted phenyl; more typically 2-pyridyl, 2-pyridyl N-oxide, 4-substituted phenyl, 2-substituted phenyl, or 2,4-substituted phenyl; wherein the phenyl substituents are independently selected from fluorine, cyano, OH, $OCH_3$, $CO_2CH_2CH_3$, and $CF_3$; and Q is

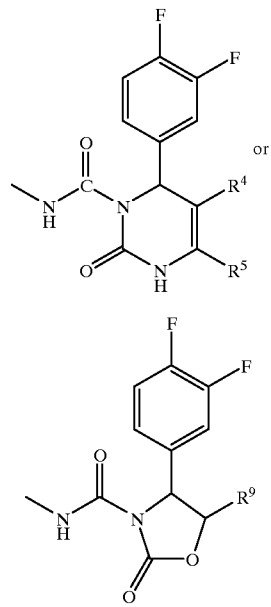

or more preferably is

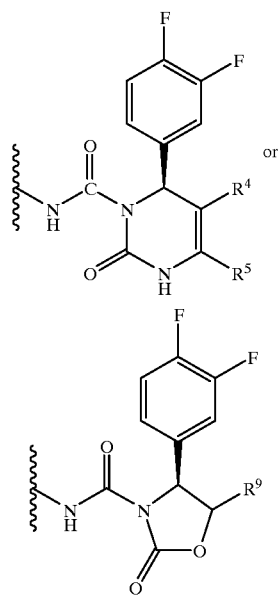

wherein
$R^4$ is H or $CO_2CH_3$;
$R^5$ is H, $CH_3$, or $CH_2OCH_3$; and
$R^9$ is H, $CH_3$, cyclopropyl, $CONH_2$, $CH_2OH$, or $COOCH_3$; provided that the compound is not (4S)-trans-4-(3,4-difluorophenyl)-2-oxooxazolidine-3-carboxylic acid-[1-(4-hydroxy-4-pyridin-2-yl-cyclohexyl)-(3R)-pyrrolidin-3-yl]amide hydrochloride.

Exemplifying the invention is the compound selected from (4S)-3-{1-[4-(2-cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester;

(4S)-cis-3-{1-[4-(2-cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester;

trans-4S-4-(3,4-difluorophenyl)-2-oxooxazolidine-3-carboxylic acid-{1-[4-(2-cyano-phenyl)-cyclohexyl]-3R-pyrrolidin-3-yl}amide;

(4S)-cis-4-(3,4-difluorophenyl)-2-oxooxazolidine-3-carboxylic acid-{1-[4-(2-cyano-phenyl)-cyclohexyl]-(3R)-pyrrolidin-3-yl}amide;

(4S)-trans-4-(3,4-difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-cis-4-(3,4-difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-trans-4-(3,4-difluorophenyl)-2-oxo-oxazolidine-3-carboxylic acid-{1-[4-(2-ethoxycarbonylphenyl)-cyclohexyl]-(3R)-pyrrolidin-3-yl}amide;

(4S)-cis-4-(3,4-difluorophenyl)-2-oxooxazolidine-3-carboxylic acid-{1-[4-(2-ethoxycarbonylphenyl)-cyclohexyl]-(3R)-pyrrolidLin-3-yl}amide;

(4S)-trans-4-(3,4-difluorophenyl)-3-[1-(4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester;

(4S)-cis-4-(3,4-difluorophenyl)-3-[1-(4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester;

(4S)-trans-4-(3,4-difluorophenyl)-2-oxo-oxazolidine-3-carboxylic acid-[1-(4-pyridin-2-yl-cyclohexyl)-(3R)-pyrrolidin-3-yl]amide;

(4S)-cis-4-(3,4-difluorophenyl)-2-oxooxazolidine-3-carboxylic acid-[1-(4-pyridin-2-yl-cyclohexyl)-(3R)-pyrrolidin-3-yl]amide;

(4S)-trans-4-(3,4-difluorophenyl)-6-methoxymethyl-3-{1-[4-(2-methoxyl-phenyl)-cyclohexyl]-(3R)-pyrrolidin-3-ylcarbamoyl}-2-oxo-1,2,3,4-tetrahydropyrimidine-5-carboxylic acid methyl ester;

(4S)-cis-4-(3,4-difluoro-phenyl)-6-methoxymethyl-3-{1-[4-(2-methoxyl-phenyl)-cyclohexyl]-(3R)-pyrrolidin-3-ylcarbamoyl}-2-oxo-1,2,3,4-tetrahydro-pyrimidine-5-carboxylic acid methyl ester;

(4S)-trans-4-(3,4-difluorophenyl)-2-oxooxazolidine-3-carboxylic acid-{1-[4-(2-methoxyphenyl)-cyclohexyl]-(3R)-pyrrolidin-3-yl}amide;

(4S)-cis-4-(3,4-difluorophenyl)-2-oxooxazolidine-3-carboxylic acid-{1-[4-(2-methoxyphenyl)-cyclohexyl]-(3R)-pyrrolidin-3-yl}amide;

(4S)-cis-4-(3,4-difluoro-phenyl)-3-[1-(4-hydroxy-4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester;

(4S)-trans-4-(3,4-difluoro-phenyl)-3-[1-(4-hydroxy-4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester;

(4S)-cis-4-(3,4-difluorophenyl)-2-oxooxazolidine-3-carboxylic acid-[1-(4-hydroxy-4-pyridin-2-yl-cyclohexyl)-(3R)-pyrroli(1in-3-yl]amide;

(4S)-4-(3,4-difluoro-phenyl)-3-{1-[4-(2-hydroxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester;

(4S)-cis-4-(3,4-difluoro-phenyl)-6-methoxymethyl-3-{1-[4-(2-hydroxy-phenyl)-cyclohexyl]-(3R)-pyrrolidin-3-ylcarbamoyl}-2-oxo-1,2,3,4-tetrahydro-pyrimidine-5-carboxylic acid methyl ester;

(4S)-trans-4-(3,4-difluorophenyl)-2-oxooxazolidine-3-carboxylic acid-{1-[4-(2-hydroxyphenyl)-cyclohexyl]-(3R)-pyrrolidin-3-yl}amide;

(4S)-cis-4-(3,4-difluorophenyl)-2-oxooxazolidine-3-carboxylic acid-{1-[4-(2-hydroxyphenyl)-cyclohexyl]-(3R)-pyrrolidin-3-yl}amide; and the pharmaceutically acceptable salts thereof.

Also exemplifying the invention is the compound selected from (4S)-trans-4-(3-,4-difluoro-phenyl)-3-{1-[4-(2-fluoro-phenyl)-cyclohexyl]-(3R)-pyrrolidin-3-ylcarbamoyl}-6-methoxymethyl-1,2,3,4-tetrahydro-pyrimidine-5-carboxylic acid methyl ester;

(4S)-trans-4-(3,4-difluoro-phenyl)-2-oxo-oxazolidine-3-carboxylic acid-{1-[4-(2-fluoro-phenyl)-cyclohexyl]-(3R)-pyrrolidin-3-yl}-aimide;

(4S)-trans-4-(3,4-difluoro-phenyl)-3-{1-[4-(4-fluoro-2-methoxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester;

(4S)-trans-4-(3,4-difluoro-phenyl)-2-oxo-oxazolidine-3-carboxylic acid {1-[4-(4-fluoro-2-methoxy-phenyl)-cyclohexyl]-(3R)-pyrrolidin-3-yl}-amide;

(4S)-4-(3,4-difluoro-phenyl)-3-{1-[4-(2-fluoro-phenyl)-4-hydroxy-cyclohexyl]-(3R)-pyrrolidin-3-ylcarbamoyl}-6-methoxymethyl-1,2,3,4-tetrahydro-pyrimidine-5-carboxylic acid methyl ester;

(4S)-4-(3,4-difluoro-phenyl)-2-oxo-oxazolidine-3-carboxylic acid-{1-[4-(2-fluoro-phenyl)-4-hydroxy-cyclohexyl]-(3R)-pyrrolidin-3-yl}-amide;

(4S)-4-(3,4-difluorophenyl)-2-oxo-oxazolidine-3-carboxylic acid {1-[4-hydroxy-4-(2-trifluoromethylphenyl)-cyclohexyl]-(3R)-pyrrolidin-3-yl} amide;

(4S)-4-(3,4-difluorophenyl)-3-{1-[4-hydroxy-4-(2-trifluoromethylphenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-4-(3,4-difluorophenyl)-2-oxo-oxazolidine-3-carboxylic acid {1-[4-(2-trifluoromethylphenyl)-cyclohexyl]-(3R)-pyrrolidin-3-yl} amide;

(4S)-4-(3,4-difluorophenyl)-6-methoxymethyl-2-oxo-3-{1-[4-(2-trifluoromethylphenyl)-cyclohexyl]-(3R)-pyrrolidin-3-ylcarbamoyl)}-1,2,3,4-tetrahydropyrimidine-5-carboxylic acid methyl ester;

(4S)-4-(3,4-difluorophenyl)-3-{1-[4-(4-fluorophenyl)-4-hydroxy-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-4-(3,4-difluorophenyl)-2-oxo-oxazolidine-3-carboxylic acid{1-[4-(4-fluorophenyl)-4-hydroxy-cyclohexyl]-(3R)-pyrrolidin-3-yl}amide;

(4S)-4-(3,4-difluorophenyl)-3-{1-[4-(4-fluorophenyl)-4-hydroxy-cyclohexyl]-(3R)-pyrrolidin-3-ylcarbamoyl}-6-methyl-2-oxo-1,2,3,4-tetrahydropyrimidine-5-carboxylic acid methyl ester;

(4S)-4-(3,4-difluorophenyl)-3-{1-[4-(4-fluorophenyl)-cyclohexyl]-(3R)-pyrrolidin-3-ylcarbamoyl}-6-methyl-2-oxo-1,2,3,4-tetryhydropyrimidine-5-carboxylic acid methyl ester;

(4S)-4-(3,4-difluorophenyl)-3-{1-[4-(4-fluorophenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-4-(3,4-difluorophenyl)-2-oxo-oxazolidine-3-carboxylic acid{1-[4-(4-fluorophenyl)-cyclohexyl]-(3R)-pyrrolidin-3-yl}amide;

(4S)-4-(3,4-difluorophenyl)-3-1-[4-(4-fluorophenyl)-4-hydroxy-cyclohexyl]-(3R)-pyrrolidin-3-ylcarbamoyl}-2-oxo-1,2,3,4-tetrahydropyrimidine-5-carboxylic acid methyl ester;

(4S)-3-{1-[4-(4-cyanophenyl)-4-hydroxycyclohexyl]-(3R)-pyrrolidin-3-ylcarbamoyl}-4-(3,4-difluorophenyl)-6-methoxymethyl-2-oxo-1,2,3,4-tetrahydropyrimidine-5-carboxylic acid methyl ester;

5-cyclopropyl-4-(3,4-difluorophenyl)-2-oxo-oxazolidine-3-carboxylic acid {1-[4-(2-fluorophenyl)-cyclohexyl]-(3R)-pyrrolidin-3-yl-amide;

(4S, 5S)-5-cyclopropyl-4-(3,4-difluorophenyl)-2-oxo-oxazolidine-3-carboxylic acid{1-[4-(4-fluorophenyl)-4-hydroxy-cyclolexyl]-(3R)-pyrrolidin-3-yl}amide;

(4S, 5S)-5-cyclopropyl-4-(3,4-difluorophenyl)-2-oxo-oxazolidine-3-carboxylic acid{1-[4-(4-cyanophenyl)-cyclohexyl]-(3R)-pyrrolidin-3-yl}amide;

(4S)-4-(3,4-difluorophenyl)-2-oxo-oxazolidine-3-carboxylic acid{1-[4-(4-cyanophenyl)-4-hydroxy-cyclohexyl]-(3R)-pyrrolidin-3-yl}amide;

(4S)-3-{1-[4-(4-cyanophenyl)-cyclohexyl]-(3R)-pyrrolidin-3-ylcarbamoyl}-4-(3,4-difluorophenyl)-6-methyl-2-oxo-1,2,3,4-tetrahydropyrimidine-5-carboxylic acid methyl ester;

(4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydropyrimidine-5-carboxylic acid methyl ester;

(4S)-3-{1-[4-(2-cyano-phenyl)-cyclohexyl]-(3R)-pyrrolidin-3-ylcarbamoyl}-4-(3,4-difluoro-phenyl)-6-methyl-2-oxo-1,2,3,4-tetrahydro-pyrimidine-5-carboxylic acid methyl ester;

(4S)-3-{1-[4-(2-cyano-4-fluoro-phenyl)-cyclohexyl]-(3R)-pyrrolidin-3-ylcarbamoyl}-4-(3,4-difluoro-phenyl)-6-methoxymethyl-2-oxo-1,2,3,4-tetrahydro-pyrimidine-5-carboxylic acid methyl ester;

(4S)-4-(3,4-difluoro-phenyl)-3-{1-[4-(4-fluoro-2-hydroxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester;

(4S)-4-(3,4-difluoro-phenyl)-2-oxo-oxazolidine-3-carboxylic acid {1-[4-(4-fluoro-2-hydroxy-phenyl)-cyclohexyl]-(3R)-pyrrolidin-3-yl}-amide;

(4S)-4-(3,4-difluoro-phenyl)-2-oxo-oxazolidine-3-carboxylic acid {1-[4-(2-cyano-4-fluoro-phenyl)-cyclohexyl]-(3R)-pyrrolidin-3-yl}-amide;

(4S)-4-(3,4-difluoro-phenyl)-2-oxo-oxazolidine-3-carboxylic acid {1-[4-(2-cyano-4-fluoro-phenyl)-cyclohexyl]-(3R)-pyrrolidin-3-yl}-amide;

(4S,5S)-4-(3,4-difluoro-phenyl)-5-methyl-2-oxo-oxazolidine-3-carboxylic acid {1-[4-(2-cyano-4-fluoro-phenyl)-cyclohexyl]-(3R)-])-pyrrolidin-3-yl}-amide;

(4S,5S)-5-Cyclopropyl-4-(3,4-difluoro-phenyl)-2-oxo-oxazolidine-3-carboxylic acid {1-[4-(2-cyano-4-fluoro-phenyl)-cyclohexyl]-(3R)-pyrrolidin-3yl}-amide;

(4S)-4-(3,4-difluoro-phenyl)-3-{1-[4-(2-fluoro-phenyl)-4-hydroxy-cyclohex-1-yl]-(3R)-pyrrolidin-3-ylcarbamoyl}-6-methyl-2-oxo-1,2,3,4-tetrahydro-pyrimidine-5-carboxylic acid methyl ester;

(4S)-trans-4-(3,4-difluoro-phenyl)-3-{1-[4-(2-fluoro-phenyl)-cyclohexyl]-(3R)-pyrrolidin-3-ylcarbamoyl}-6-methyl-2-oxo-1,2,3,4-tetrahydro-pyrimidine-5-carboxylic acid methyl ester;

(4S)-cis-4-(3,4-difluoro-phenyl)-3-[1-(4-hydroxy-4-pyridin-2-yl-cyclohexyl)-(3R)-pyrrolidin-3-ylcarbamoyl]-2-oxo-1,2,3,4-tetrahydro-pyrimidine-5-carboxylic acid methyl ester;

(4S)-trans-4-(3,4-difluorophenyl)-3-[1-(4-pyridin-2-yl-cyclohexyl)-(3R)-pyrrolidin-3-ylcarbamoyl]-2-oxo-1,2,3,4-tetrahydro-pyrimidine-5-carboxylic acid methyl ester;

(4S)-trans-3{1-[4-(2-cyano-phenyl)-piperidin-1-yl]-(3R)-pyrrolidin-3-ylcarbamoly}-4-(3,4-difluoro-phenyl)-2-oxo-1,2,3,4-tetrahydro-pyrimidine-5-carboxylic acid methyl ester;

(4S,5S)-trans-5-cyclopropyl-4-(3,4-difluorophenyl)-2-oxo-oxazolidine-3-carboxylic acid {1-[4-(4-fluorophenyl)-cyclohexyl]-(3R)-pyrrolidin-3-yl-amide;

(4S)-4-(3,4-difluoro-phenyl)-3-[1-(4-hydroxy-4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester;

(4S)-trans-4-(3,4-difluorophenyl)-5-methyl-2-oxooxazolidine-3-carboxylic acid-[1-(4-pyridin-2-yl-cyclohexyl)-(3R)-pyrrolidin-3-yl]amide;

trans-4S-(3,4-difluorophenyl)-3-[1-(4-oxopyridin-2-yl-cyclohexyl)-3R-pyrrolidin-3-ylcarbamoyl]-6-methyl-2-oxo-1,2,3,4-tetrahydro-pyrimidine-5-carboxylic acid methyl ester;

trans-2-(3,4-difluorophenyl)-1-[1-(4-pyridin-2-yl-cyclohexyl)-3R-pyrrolidin-3-ylcarbamoyl]-6-methoxymethyl-2-oxo-1,2,3,4-tetrahydro-pyrimidine;

(4S,5R)-trans-4-(3,4-difluorophenyl)-3-{1-[4-(4-fluoro-2-methoxycarbonylphenyl)-cyclohexyl]-(3R)-pyrrolidin-3-ylcarbamoyl}-2-oxo-oxazolidine-5-carboxylic acid methyl ester;

(4S,5R)-trans-4-(3,4-difluorophenyl)-3-(1-{4-[4-fluoro-2-(2,2,2-trifluoroethoxy)phenyl]cyclohexyl}-(3R)-pyrrolidin-3-ylcarbamoyl)-2-oxo-oxazolidine-5-carboxylic acid methyl ester;

(4S,5R)-trans-4-(3,4-difluorophenyl)-2-oxo-3-[1-(4-pyridin-2-ylcyclohexyl)-(3R)-pyrrolidin-3-ylcarbamoyl]-oxazolidine-5-carboxylic acid methyl ester;

(4S,5R)-trans-4-(3,4-difluorophenyl)-3-{1-[4-(4-fluoro-2-methoxyphenyl)cyclohexyl]-(3R)-pyrrolidin-3-ylcarbamoyl]-2-oxo-oxazolidine-5-carboxylic acid methyl ester;

(4S,5R)-3-{1-[4-Cyano-4-(2-methoxyphenyl)cyclohexyl]-(3R)-pyrrolidin-3-ylcarbamoyl}-4-(3,4-difluorophenyl)-2-oxo-oxazolidine-5-carboxylic acid methyl ester;

(4S,5R)-3-{1-[4-Cyano-4-(2-fluorophenyl)cyclohexyl]-(3R)-pyrrolidin-3-ylcarbamoyl}-4-(3,4-difluorophenyl)-2-oxo-oxazolidine-5-carboxylic acid methyl ester;

(4S,5R)-trans-3-{1-[4-(2-cyanophenyl)cyclohexyl]-(3R)-pyrrolidin-3-ylcarbamoyl}-4-(3,4-difluorophenyl)-2-oxo-oxazolidine-5-carboxylic acid methyl ester;

(4S,5R)-trans-4-(3,4-difluorophenyl)-5-hydroxymethyl-2-oxo-oxazolidine-3-carboxylic acid {1-[4-(4-fluorophenyl)cyclohexyl]-(3R)-pyrrolidin-3-yl}amide;

(4S,5R)-trans-4-(3,4-difluorophenyl)-5-hydroxymethyl-2-oxo-oxazolidine-3-carboxylic acid {1-[4-(4-fluoro-2-methoxyphenyl)cyclohexyl]-(3R)-pyrrolidin-3-yl}amide;

(4S,5R)-trans-4-(3,4-difluorophenyl)-3-{1-[4-(4-fluoro-2-methoxyphenyl)cyclohexyl]-(3R)-pyrrolidin-3-ylcarbainoyl]-2-oxo-oxazolidine-5-carboxamide;

(4S,5R)-trans-4-(3,4-difluorophenyl)-3-{1-[4-(4-fluorophenyl)cyclohexyl]-(3R)-pyrrolidin-3-ylcarbamoyl]-2-oxo-oxazolidine-5-carboxamide;

(4S,5R)-trans-4-(3,4-difluorophenyl)-3-{1-[4-(2-fluorophenyl)cyclohexyl]-(3R)-pyrrolidin-3-ylcarbamoyl]-2-oxo-oxazolidine-5-carboxamide;

(4S,5R)-trans-3-{1-[4-(2-cyano-4-fluorophenyl)cyclohexyl]-(3R)-pyrrolidin-3-ylcarbamoyl}-4-(3,4-difluorophenyl)-2-oxo-oxazolidine-5-carboxamide; and the pharmaceutically acceptable salts thereof.

In a preferred embodiment the compound is selected from Compound A:

Compound A:

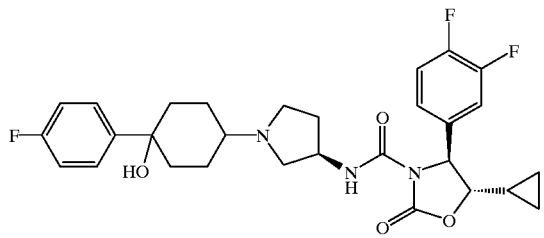

Compound B:

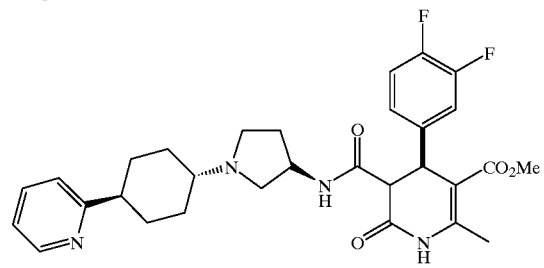

Compound C:

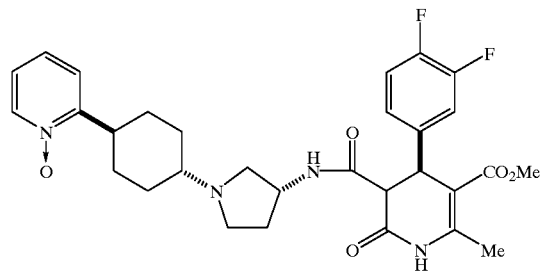

and the pharmaceutically acceptable salts thereof.

Another preferred embodiment is Compound A or a pharmaceutically acceptable salt thereof. Another preferred embodiment is Compound B or a pharmaceutically acceptable salt thereof. Still another preferred embodiment is Compound C or a pharmaceutically acceptable salt thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another example of the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another illustration of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing lower urinary tract tissue in a subject in need thereof which comprises administering to the subject a therapeutically effective amount of any of the compounds (or any of the compositions) described above.

More specifically exemplifying the invention is the method of inhibiting contraction of prostate tissue or relaxing lower urinary tract tissue wherein the compound (or composition) additionally does not cause a fall in blood pressures at dosages effective to inhibit contraction of prostate tissue.

More particularly illustrating the invention is the method of inhibiting contraction of prostate tissue or relaxing lower urinary tract tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see, K. A. Vatz, *Headache* 1997:37: 107–108) and cardiac arrhythmia.

An additional illustration of the invention is the use of any of the compounds described above in the preparation of a medicament for: a) the treatment of benign prostatic hyperplasia; b) relaxing lower urinary tract tissue; or c) inhibiting contraction of prostate tissue; in a subject in need thereof.

An additional example of the invention is, the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying at least ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Carasylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Compounds of this invention are used to reduce the acute symptoms of BPH. Thus, compounds of this invention may be used alone or in conjunction with a more long-term anti-BPH therapeutics, such as testosterone 5-α reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within it, scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight i)r branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent. The term "poly-substituted" as used herein shall include di-, tri-, tetra- and penta-substitution by a named substituent. Preferably, a poly-substituted moiety is di-, tri- or tetra-substituted by the named substituents, most preferably, di- or tri-substituted.

It is intended that the definition of any substituent or variable (e.g., X, $R^6$, $R^{19}$) at a particular location in a molecule be independent of its definitions elsewhere in that molecule. Thus,—$N(R^{19})2$ represents —$NH_2$, —$NHCH_3$, —$NHC_2H_5$, —$N(CH_3)C_2H_5$, etc. and

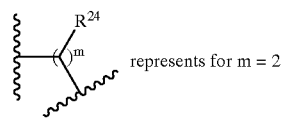

represents for m = 2

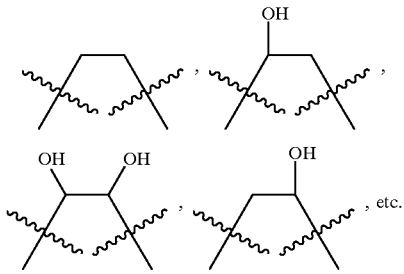

It is understood that substituents and substitution patterns on the compounds of the instant invention can be selected by one of ordinary skill in the art to provide compounds that are chemically stable and that can be readily synthesized by techniques known in the art as well as those methods set forth below. Where multiple substituent moieties are disclosed or claimed, the substituted compound can be independently substituted by one or more of the disclosed or claimed substituent moieties, singly or plurally.

The term "Z is hydrogen," when refering to the "Q" group

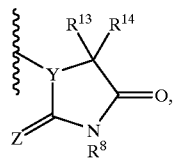

refers to moiety

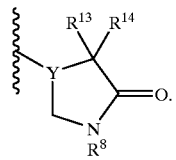

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyrid.azinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

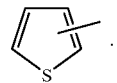

The terms "(+)-DHP" and "DHP" as used herein, refer to a dihydropyrimidinone group of the formula

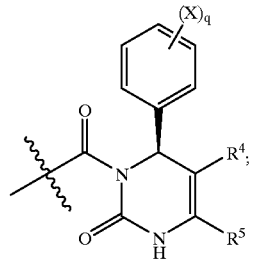

for example:

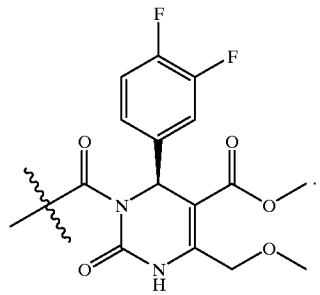

The term "activated (+)-DHP," as used herein, refers to a N-3-(activated)carbamate of the desired dihydropyrimidinone where the activating group is, for example, a p-nitrophenyloxy group. A specific example of an activated (+)-DHP is 4-(3,4-difluorophenyl)-5-methoxycarbonyl-6-methoxymethyl-2-oxo-1,2,3,4-tetrahydropyrimidine-3-carboxylic acid (4-nitrophenyl ester), also referred to as the compound 15.

The term "(S)-oxa" as used herein, refers; to an oxazolidinone group of the formula

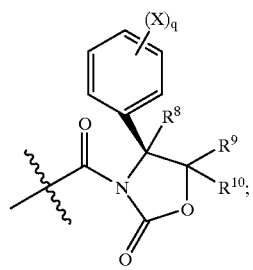

for example,

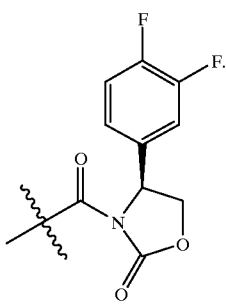

The term "activated (S)-oxa" as used herein, refers to an N-(activated)carbamate of the desired oxazolidinone where the activating group is, for example, a p-nitrophenyloxy group. A specific example of an activated (S)-oxa group is 4-(3,4-difluorophenyl)-2-oxo-oxazolidine-3-carboxylic acid 4-nitrophenyl ester (i.e., compound 16).

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition raay be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistrv*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificity of binding of compounds showing affinity for the alpha 1a receptor is shown by comparing affinity to membranes obtained from tranfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules;, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-lirked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicamE nt typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-α reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. No. 4,377,584 and 4,760,071, for example). In addition to PROSCAR®, which is principally active in prostatic tissue due to its selectivity for human 5-α reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. No.'s. 4,377,584 and 4,760,071 which describe dosages and formulations for 5α-reductase inhibitors.

Abbreviations used in the instant specification, particularly the Schemes and Examples, are as follows:

BCE=bromochloroethane
Boc or BOC=t-butyloxycarbonyl
BOPCl=bis(2-oxo-3-oxazolidinyl)phosphinic chloride
Cbz-Cl or CBZCl=benzyloxycarbonyl chloride
CSA=10-Camphorsulfonic acid
DAST=diethylaminosulfurtrifluoride
DEAD=diethylazodicarboxylate
DMF=N,N-dimethylformamide
DMSO=dimethylsulfoxide
EDCI=1-(3-dimethylaminopropyl)-3-ethylcarbodiimide hydrochloride
Et=ethyl
$Et_3N$=triethylamine
EtOAc=ethyl acetate
EtOH=ethanol
FABLRMS=fast atom bombardment low resolution mass spectroscopy
HMPA=hexamethylphosporamide
HPLC=high performance liquid chromatography
HOAc=acetic acid
HOBt=1-hydroxy benzotriazole hydrate
i-PrOH=2-propanol
i-Pr2NEt=diisopropylethylamine
LAH=lithium aluminum hydride
LDA=lithium diisopropyl amide
mCPBA=meta-chloroperbenzoic acid
Me=methyl
MeOH=methanol
NMR=nuclear magnetic resonance
PCTLC=preparative centrifugal thin layer chromatography
PEI=polyethylenimine
Ph=phenyl
pTSOH=p-toluenesulfonic acid
RT=retention time
TEBAC=benzyltriethylammonium chloride TFA=trifluoroacetic acid
THF=tetrahydrofuran
TLC=thin layer chromatography
TMS=trimethylsilyl
TMSCN=trimethylsilylcyanide The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

Many of the compounds claimed within this invention can be assembled as outlined in a general fashion in Scheme 1. Reductive amination of a hydroxy amino derivative with a cycloalkanone provides an intermediate which can be carried on via either of the two outlined methods; conversion of the hydroxy group to a halide or tosylate and displacement with an anionic equivalent of one of the Q groups. Alternatively, the hydroxy group can be manipulated into an amino group and acylated or alkylated to supply the desired amide as urea linked analogs.

An example of this approach is highlighted where the central portion of the antagonist is assembled from N-protected 3-hydroxy azetidine. Conversion of the hydroxy to a protected amino group and deprotection of the azetidine nitrogen provided the appropriate amine for reductive amination with a cycloalkanone. which after deprotection was acylated with an activated Q species. This was accomplished with the 3-aminomethyl azetidine linker in an analogous fashion.

Derivatives where the central molecular framework is a 4-amino piperidine were prepared from isonipecotic acid via the sequence outlined in Scheme 2. Isonipecotic acid was converted to 4-(tert-butoxycarbonyl)amino piperidine in three chemical steps. Reductive amination with 4-cyano 4-phenyl cyclohexanone provided a separable mixture of cis and trans products, which after Boc deprotection and acylation provided the desired antagonists.

The 3-amino piperidinyl bridged compounds were assembled in analogous fashion starting from nipecotic acid, Scheme 3. The corresponding 3-amino pyrroldinyl analogs were obtained by substituting the commercially available 3-(tert-butoxycaronyl)amino pyrrolidine for the corresponding piperidinyl material as shown in Scheme 4.

Selective acylation of the primary amines was accomplished by treatment of the amines with nearly equimolar quantities of the activated termini species (i.e., the "Q" groups). The activated termini species comprising the "Q" groups are readily prepared by one of ordinary skill in the art. For example, unsubstituted, alkyl- and cycloalkyl-substituted oxazolidinones are prepared and activated in general by published and well developed chemistry, in particular, of Evans. [Evans, D. A.; Nelson, J. V.; Taber, T. R. Top. Stereochem. 13, 1 (1982)] The starting materials, in general, are natural and unnatural amino acids. For instance, some of the preferred compounds are prepared from substituted phenyl glycine derivatives, which after reduction of the carboxylate and a phosgene equivalent mediated cyclization provides the substituted oxazolidinone ring system. Deprotonation with n-butyl lithium and addition to a THF solution of p-nitrophenylchloroformate produces the stable, isolable "activated" oxazolidinone (oxa).

Oxazolidinones substituted with carboxylate, carboxamide, and hydroxymethyl are prepared by hydroxyamination of olefins to provide protected aminoalcohols, using procedures as described in Sharpless et al., Angew. Chem. Int. Ed. Engl., 35, 2813 (1996). Deprotection under standard conditions followed by a phosgene equivalent to mediate cyclization provides the substituted oxazolidinone ring system. Deprotonation with a strong base, for example, lithium bis(trimethylsilyl)amide, and addition to a THF solution of p-nitrophenylchloroformate produces the stable, isolatable "activated" oxazolidinone.

Dihydropyrimidinones are prepared by condensation reaction of the aldehyde, urea and a 1,3-acetoacetate type derivative catalyzed by a Lewis Acid, a copper (I) species and acetic acid. Activation was accomplished by treatment with a strong base, for instance, $LiN(TMS)_2$, followed by addition to a THF solution of p-nitrophenylchloroformate.

Hydantoins and cycloimide were prepared in two chemical steps from ketones as outlined in the literature. More specifically, hydantoins were prepared according to known methodology, e.g., J. J. Edmunds et al., *J. Med. Chem.* 1995, 38, pp. 3759–3771; J. H. Poupart et al., *J. Chem. Res.* 1979, pp. 174–175. Saccharins were prepared according to known methods, e.g., page 40 and Examples 21 and 22 of PCT International Application Publication No. WO96/25934, published Aug. 29, 1996.

The dihydropyrimidinones and the unsubstituted, alkyl- and cycloalkyl-substituted oxazolidinones were synthesized independently in racemic form, and then separated utilizing preparative chiral HPLC. Their optical rotations were recorded. Then they were activated and reacted with prerequisite amines. From the receptor binding studies, a preferred isomer was identified, the (+) rotational isomer in each case. The absolute configurations were determined to be (S) for both the dihydropyrimidinones and oxazolidinones by correlating their optical rotations with x-ray crystal structures obtained of fragments involved in the production of the antagonists.

The oxazolidinones substituted with caiboxylate, carboxamide, and hydroxymethyl were prepared in enantiomer-enriched form and the assignments of (4S,5R) were made in accordance with Sharpless et al., Angew. Chem. Int. Ed. Engl., 35, 2813 (1996)

Antagonists with cycloalkyl linking chains can be assembled by reductive amination of the prerequisite amino alcohol and a ketone, for example, N-(2-cyanophenyl) piperidin-4-one, Scheme 5. Conversion of the hydroxy to a tosylate with tosyl anhydride, followed by displacement by the sodium or lithium salt of the desired Q group completes the synthesis of the targeted antagonists.

Some of the required ketones were readily assembled following the sequence outlined in Scheme 6. For example, a substituted benzyl nitrile, sulphone, etc. could be added to methyl acrylate (or other substituted acrylates), submitted to Dieckman cyclization, hydrolyzed and decarboxylated providing appropriately substituted ketones. Further modifications of the ketones can be accomplished following the Dieckman cyclization, which provides the β-keto ester which can be either: (a) submitted to a reductive amination and carried on to final product, (b) enolized and alkylated then reductively aminated, deprotected and further manipulated providing further substituted analogs; or (c) hydrolyzed and decarboxylated and run through the above described conditions producing the desired antagonists.

Another strategy for the synthesis of some geminally disubstituted cyclic ketones, in particular, 4,4-disubstituted cyclohexanones was accomplished as outlined in Schemes 7A and 7B starting from benzophenone derivatives and substituted methyl vinyl ketones which under basic conditions lead to the 4,4-aryl cyclohex-2-en-1-ones in good yield. Subsequent hydrogenation, reductive amination and deprotection provided the appropriate acylation/alkylation precursors. Alternatively, the 4,4-diaryl cyclohex-2-en-1-ones could be subjected to Michael addition of selected nucleophiles, alkylation or aldolyzation of the enolate of the resulting ketone then reductively aminated and carried through the standard chemical transformation to provide further elaborated antagonists.

The synthesis of some additional compounds of the present invention is described in Schemes 8–17. Schemes 16–17 describe the synthesis of the 3-aminomethyl-3-hydroxyazetidine and the 4-amino-3-hydroxypyrrolidine intermediates. The 3-aminomethyl-3-hydroxyazetidine was assembled from the commercially available N-protected 3-hydroxyl azetidine as outlined Scheme 16 Swern oxidation of the alcohol with dimethylsulfoxide and oxalyl chloride provided the azetidinone. The zinc iodide catalyzed addition of TMSCN produced the cyanohydrin. Subsequent LAH reduction of the nitrile and two protecting group manipulations yielded the key intermediate required for the reductive aminations with the cyclohexanones. Deprotection of the N-BOC carbamate and acylation with preferred activated "Q"-groups furnished the final targets. The synthesis of the 4-amino-3-hydroxypyrrolidine intermediate began with 3,4-pyrroline. BOC protection of the amine followed by mCPBA oxidation provided the epoxidation. Subsequent sodium azide opening of the epoxide and triphenylphosphine/water mediated reduction produced 4-amino-N-1-(1,1-dimethylethoxycarbonyl)-3-hydroxypyrrolidine. After two protecting manipulations the key amino intermediate was alkylated by reductive amination reactions with cyclohexanones. Following the cleavage of the CBZ protecting group acylation with preferred activated "Q"-groups furnished the final targets.

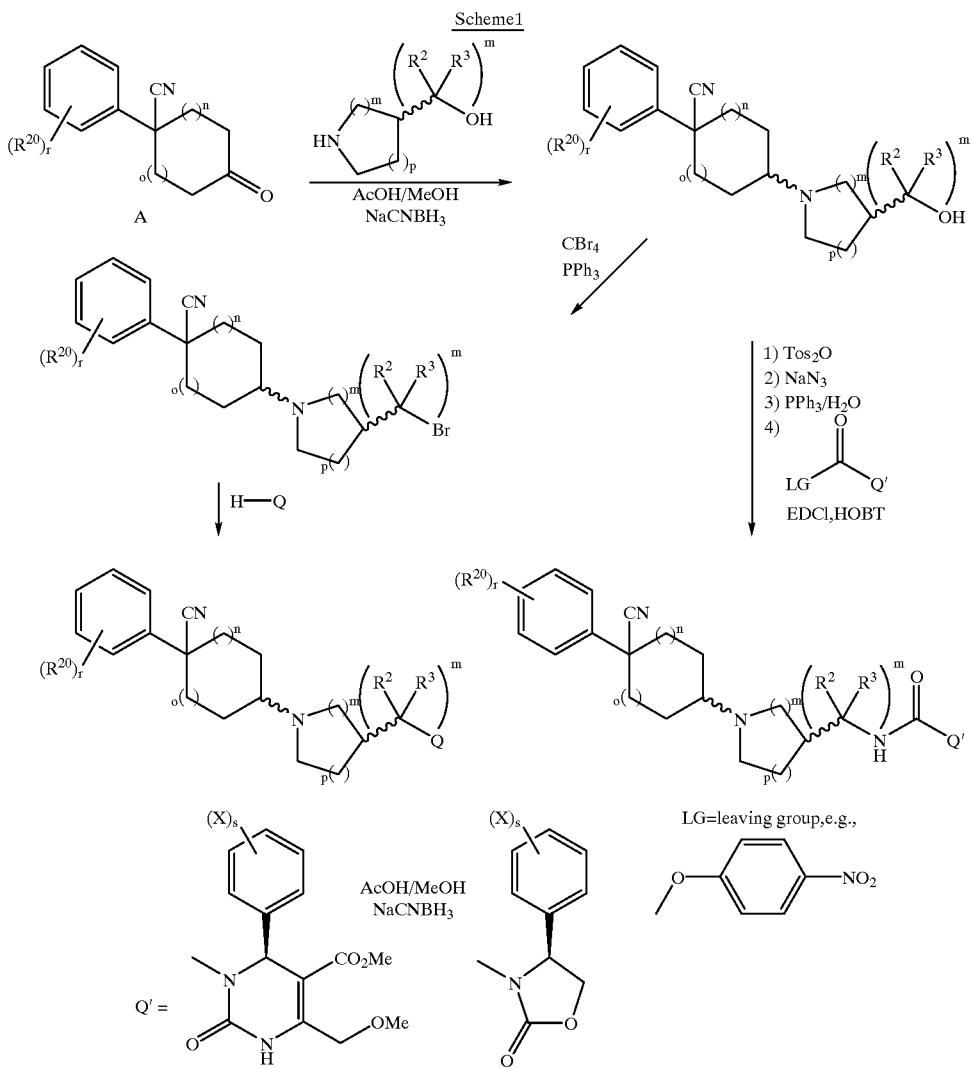

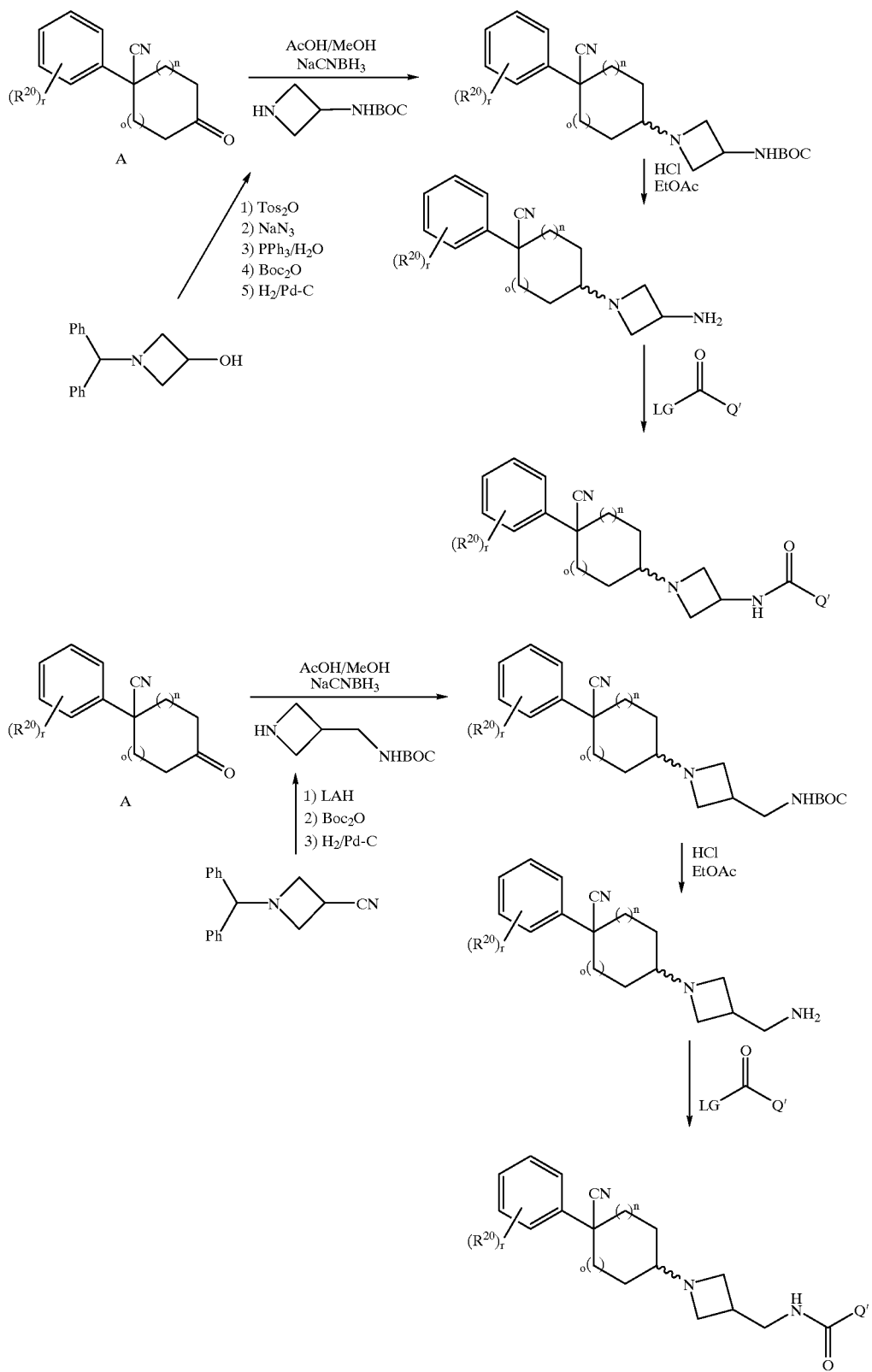

SCHEME 2
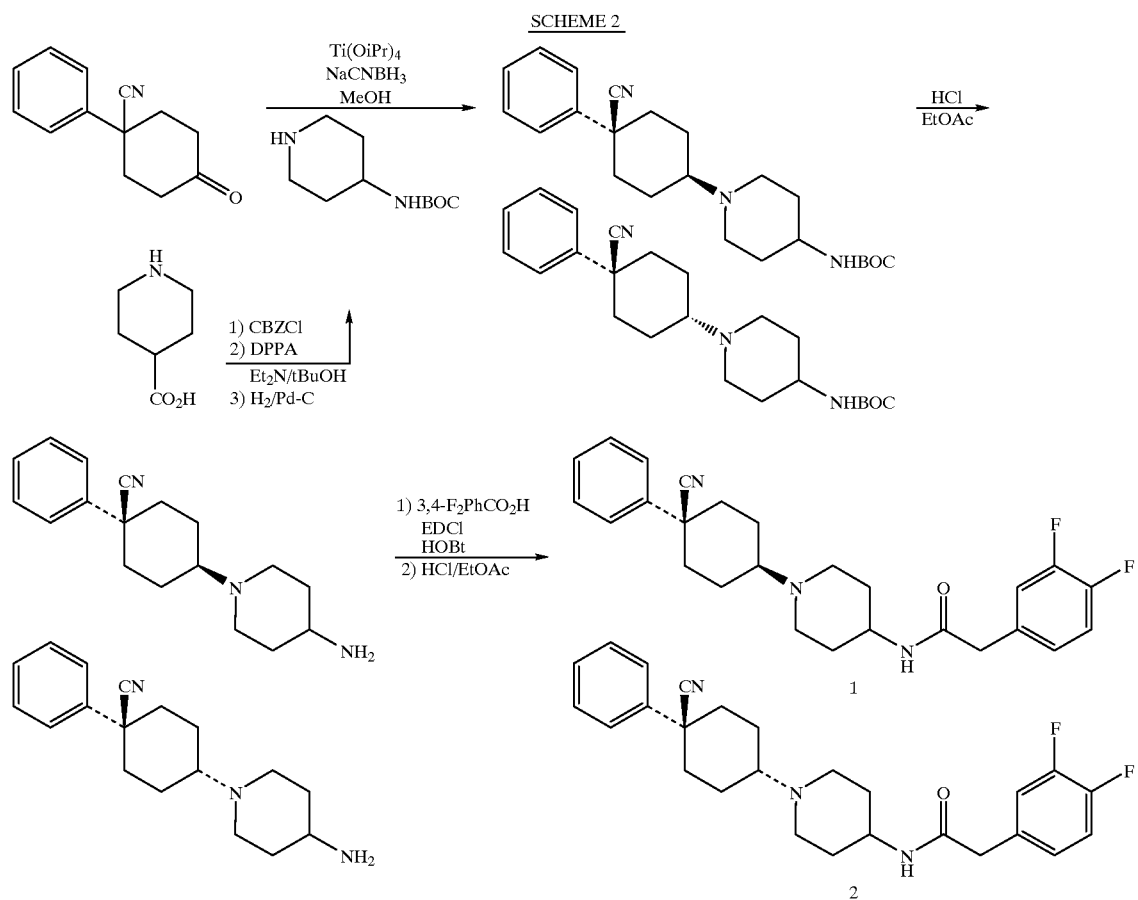
SCHEME 3
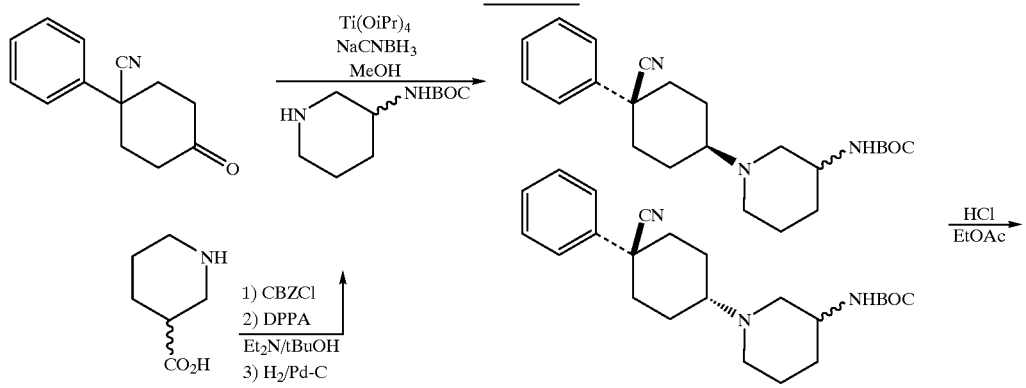

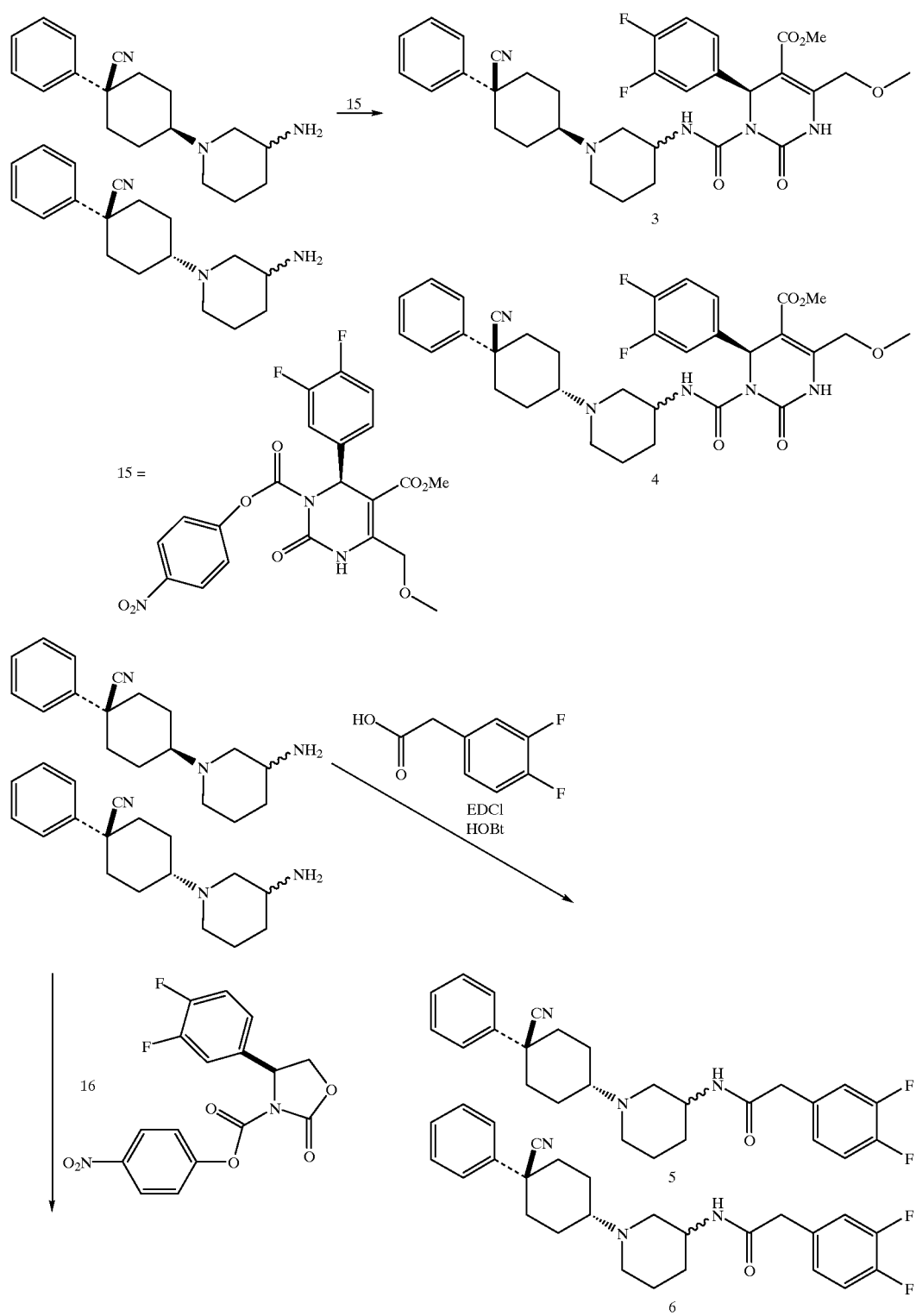

-continued
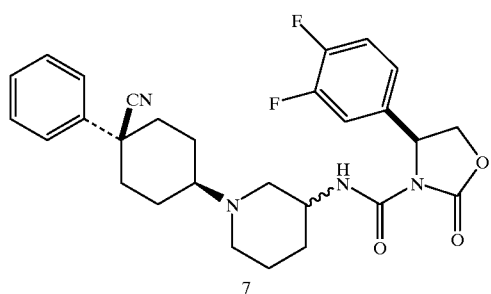
7
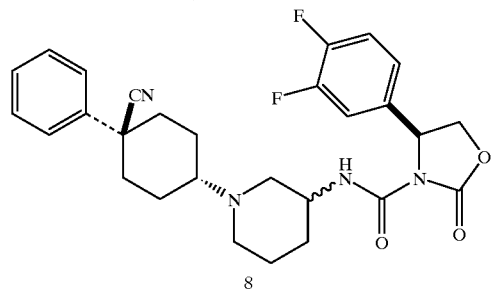
8
SCHEME 4
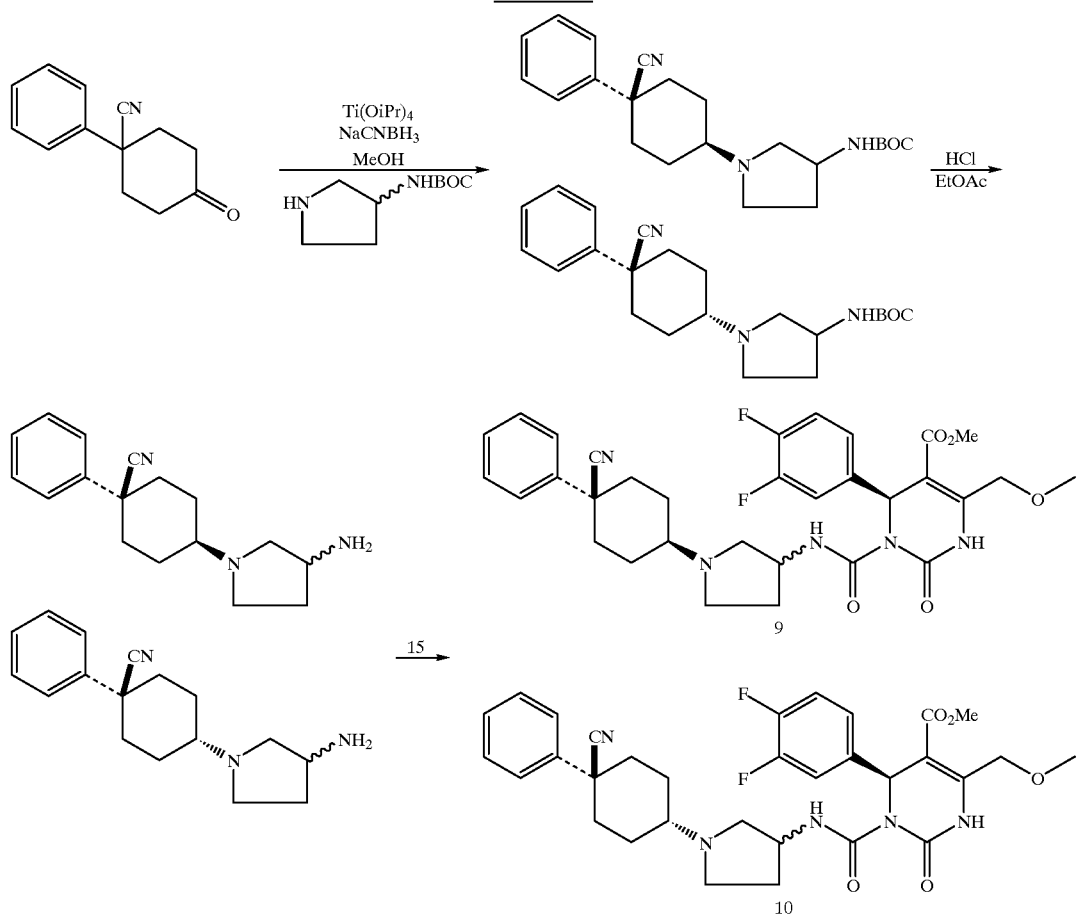

-continued
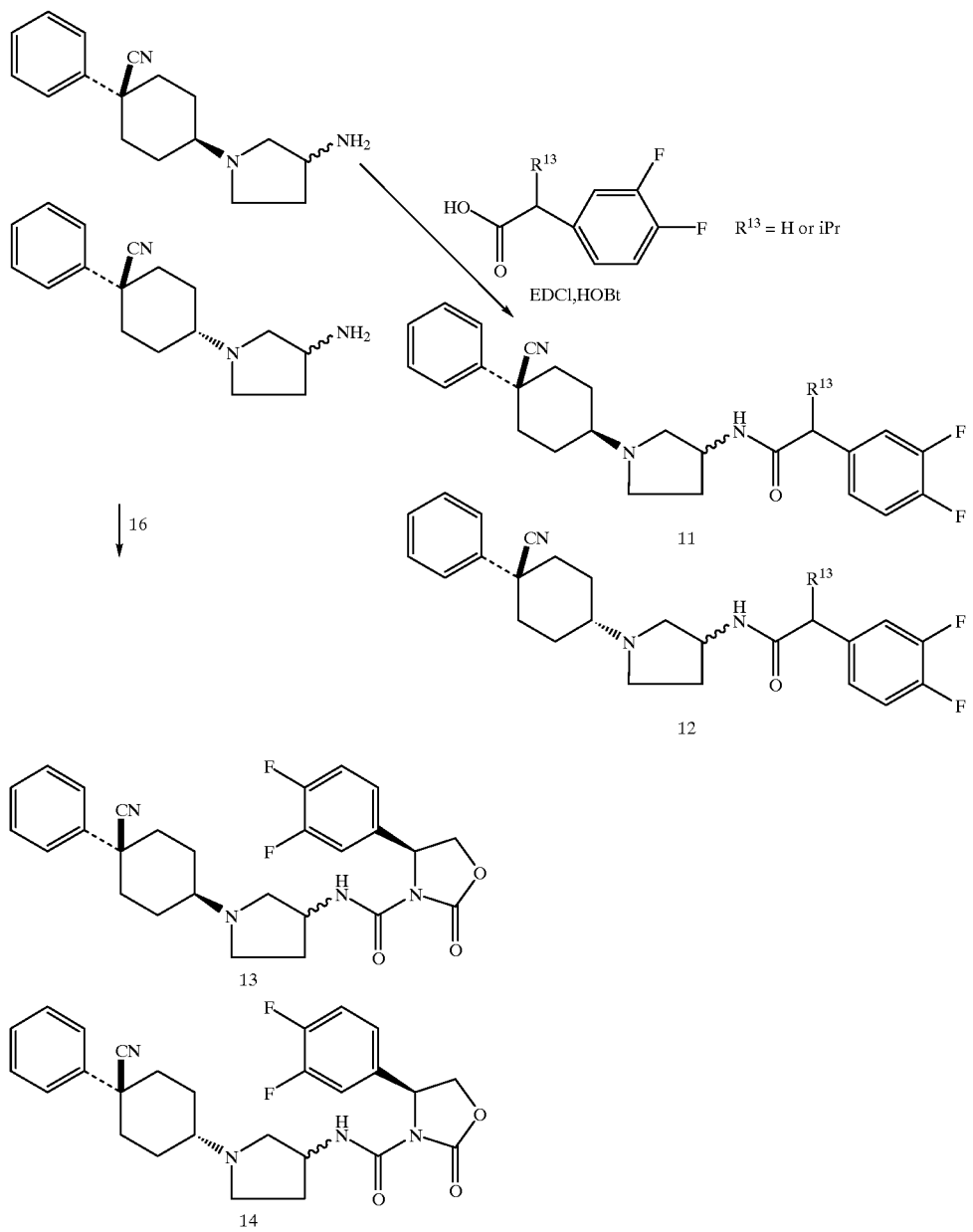
SCHEME 5
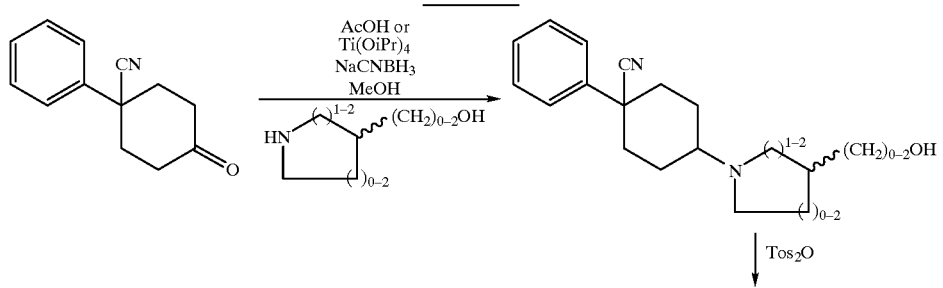

-continued
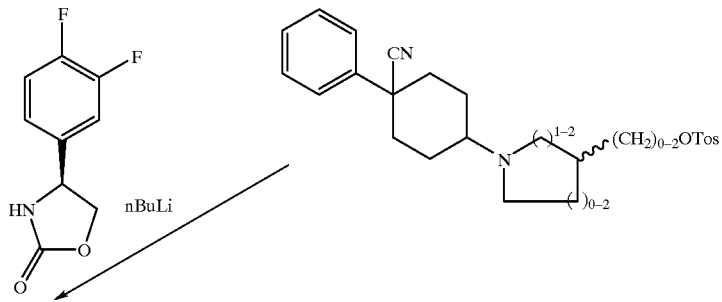
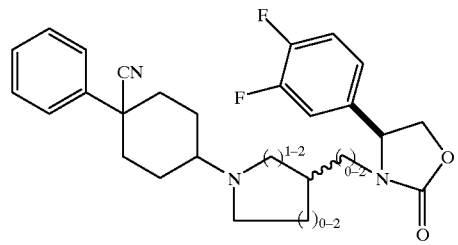
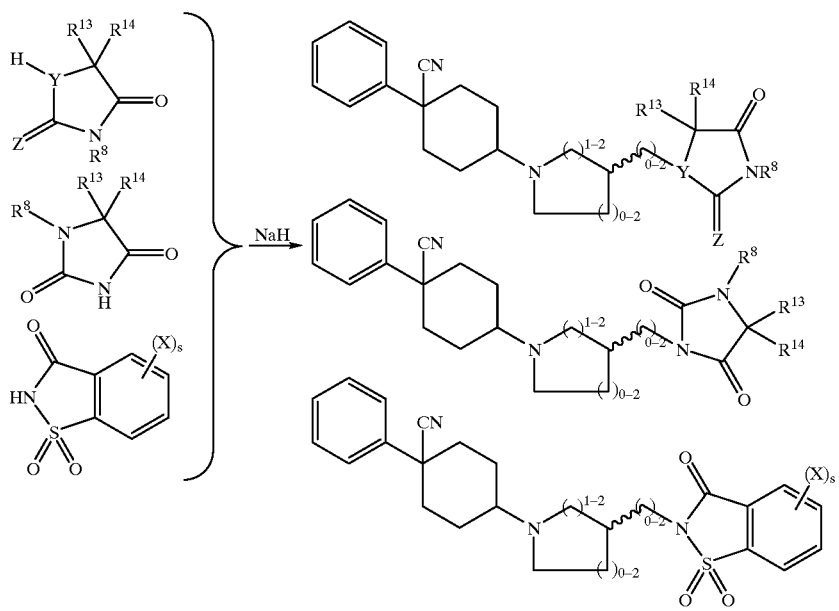
SCHEME 6
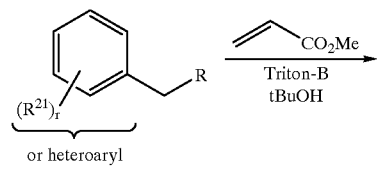
R = CN, SO₂alk, others
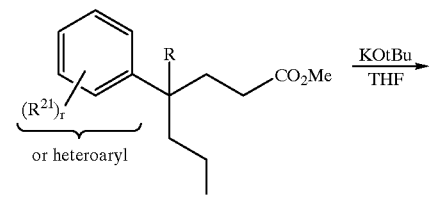
-continued
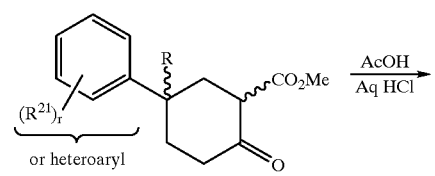

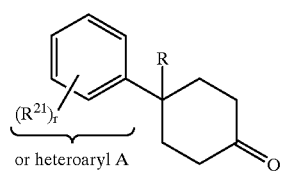
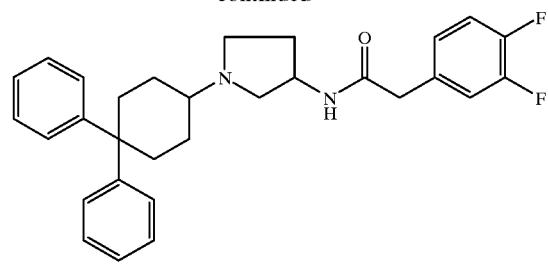
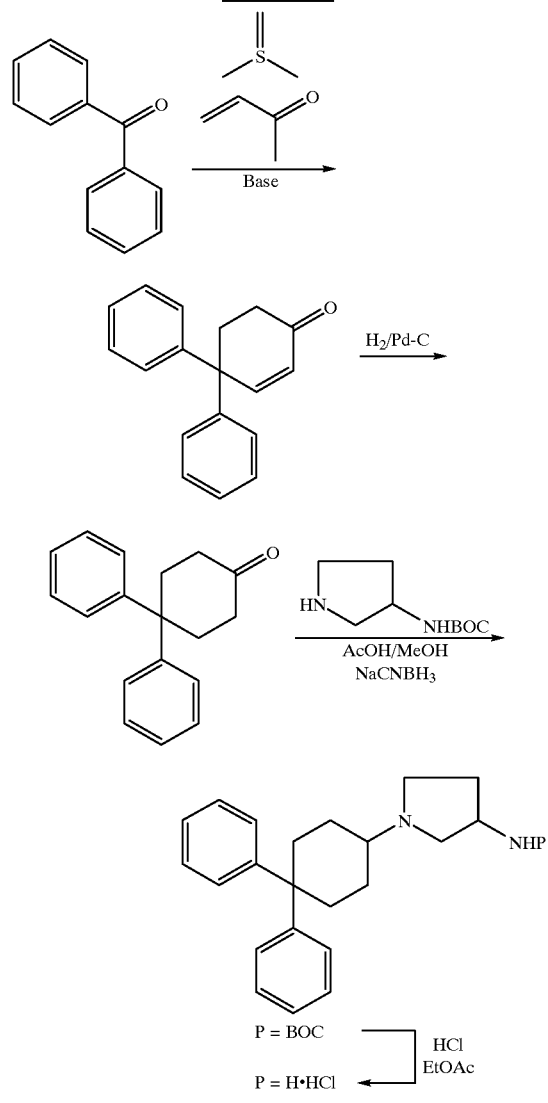
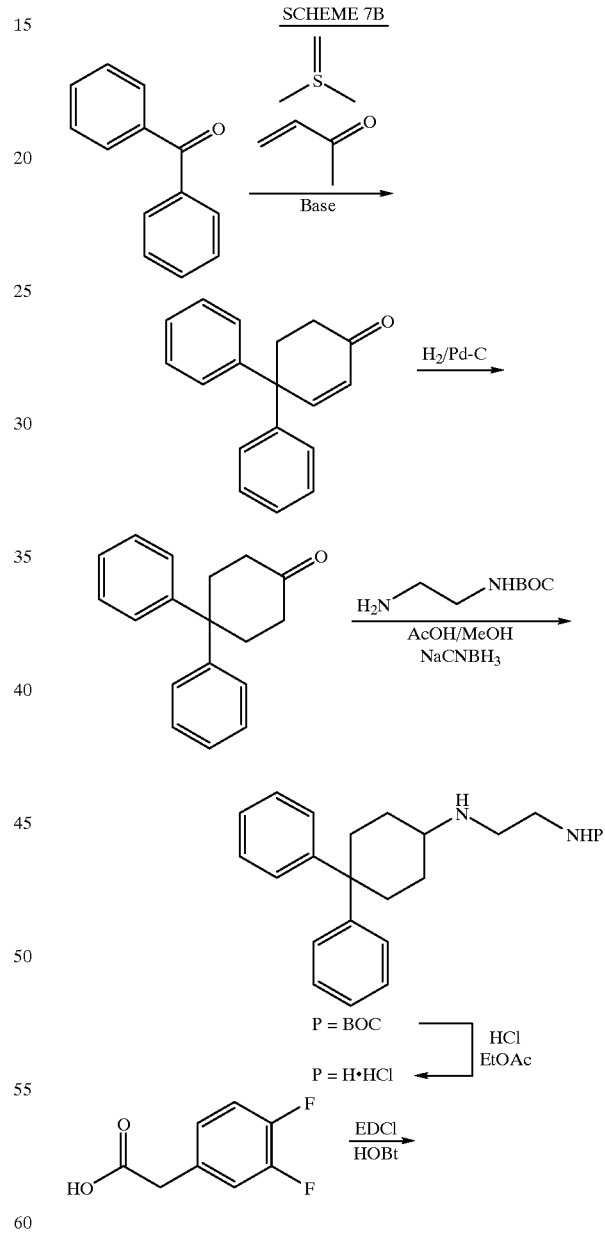

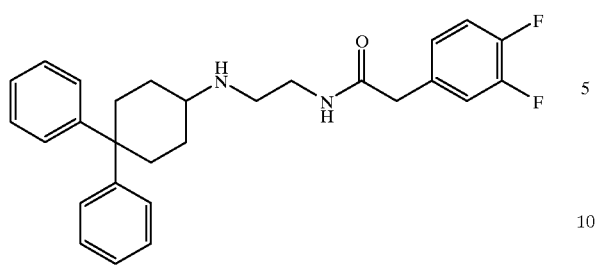
Scheme 8
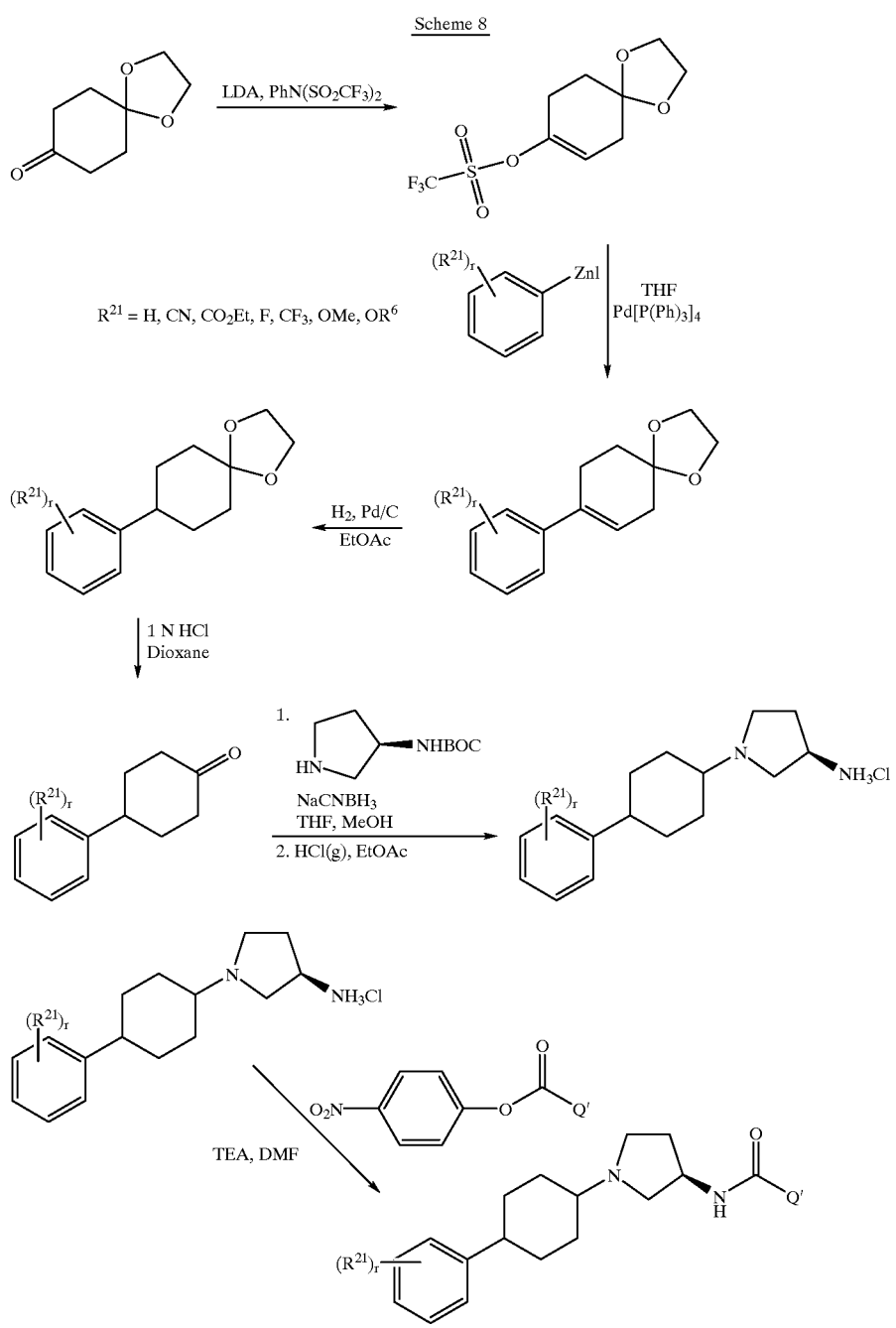

Q' = 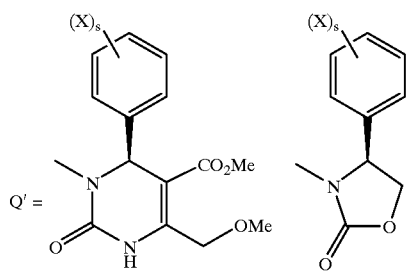
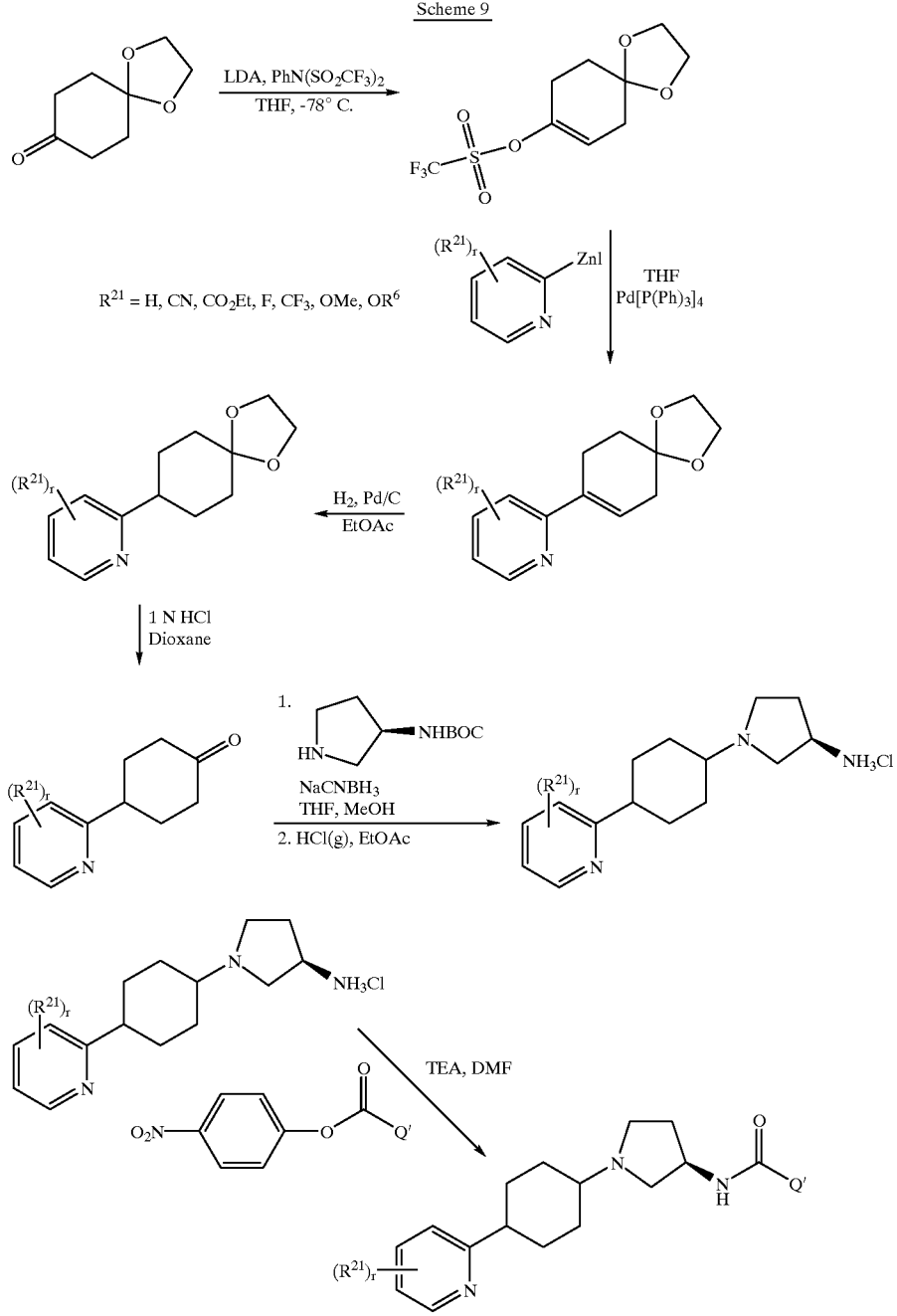
Scheme 9

-continued
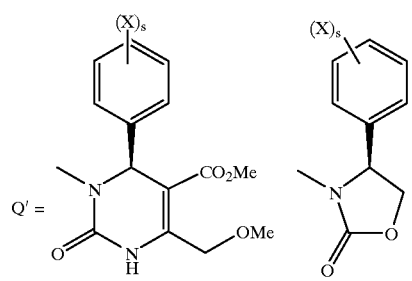
Q' =
Scheme 10
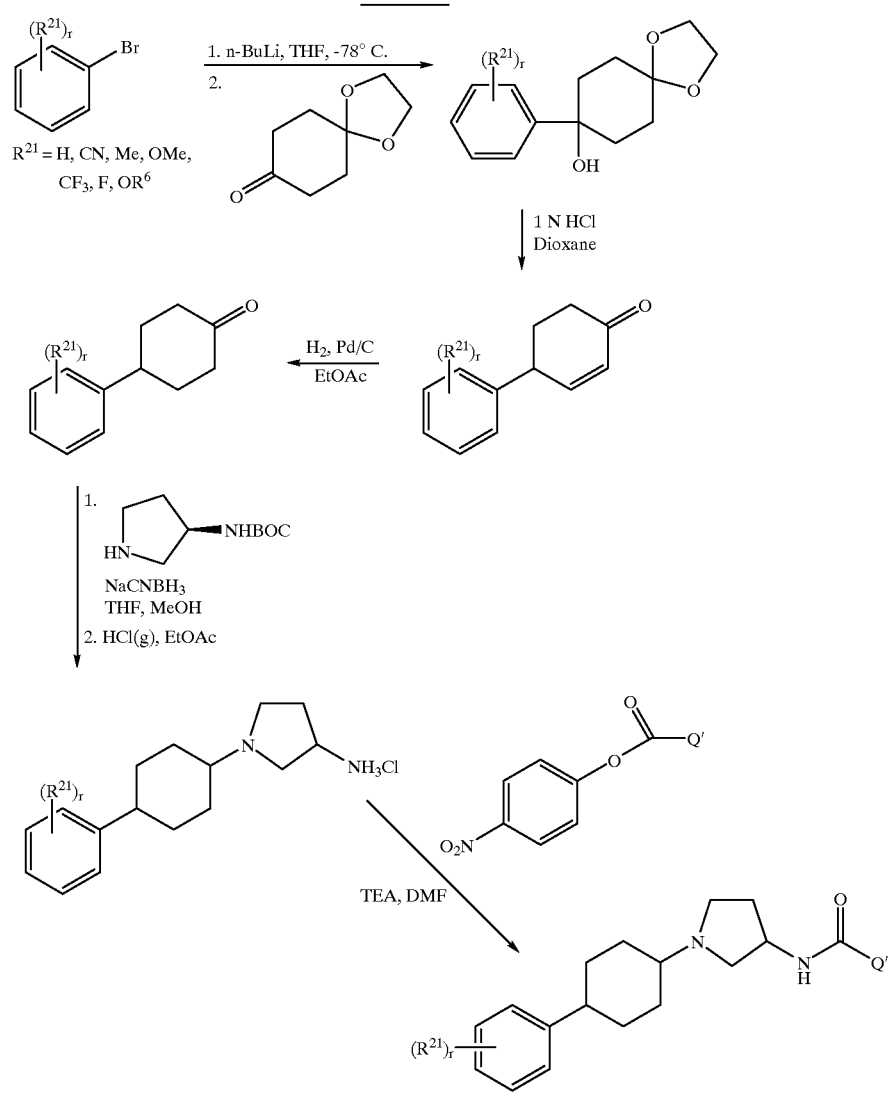

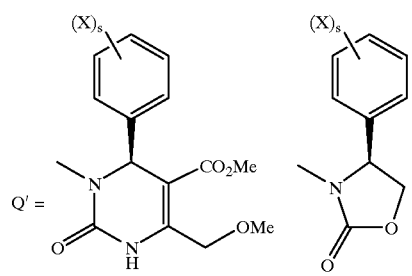
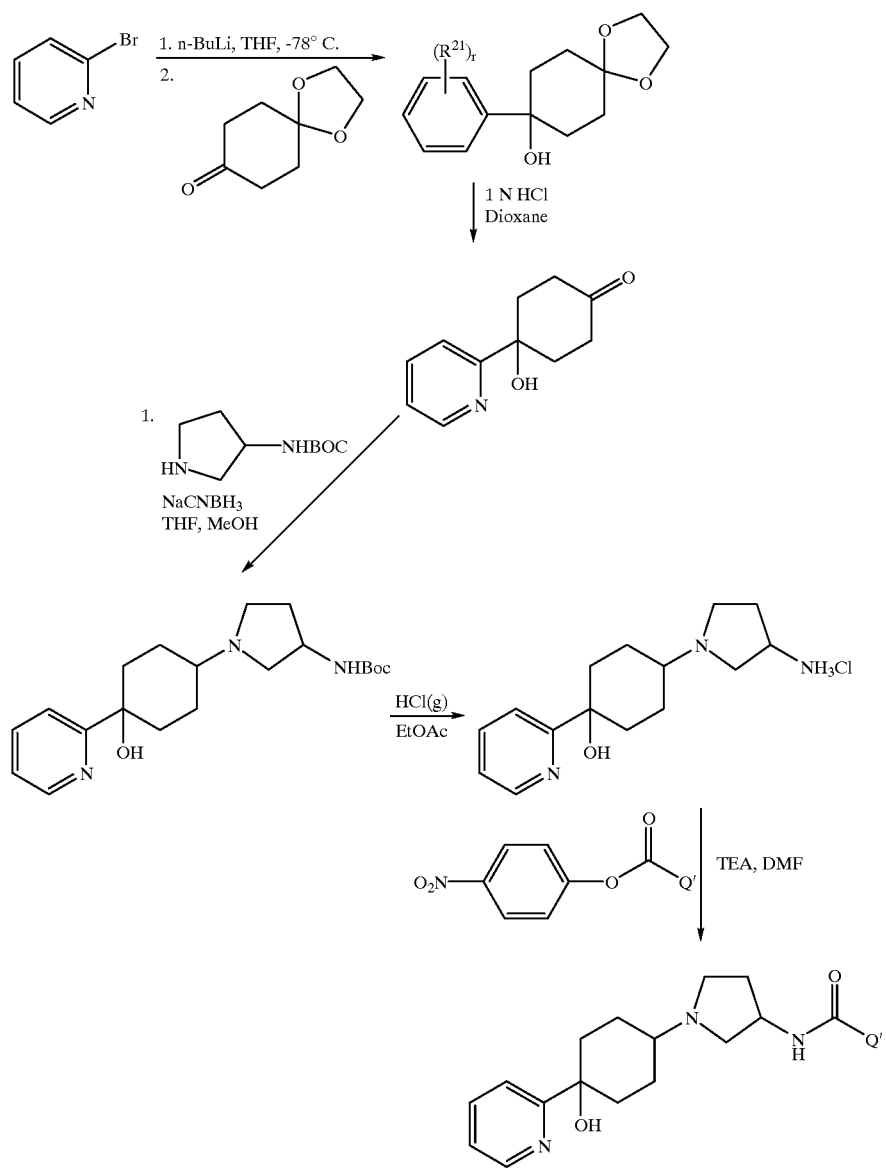

-continued
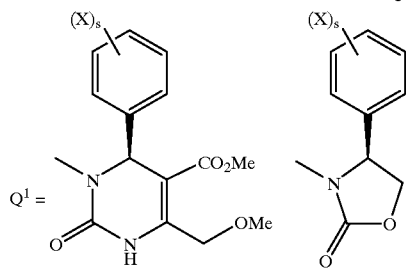
$Q^1 =$
Scheme 12
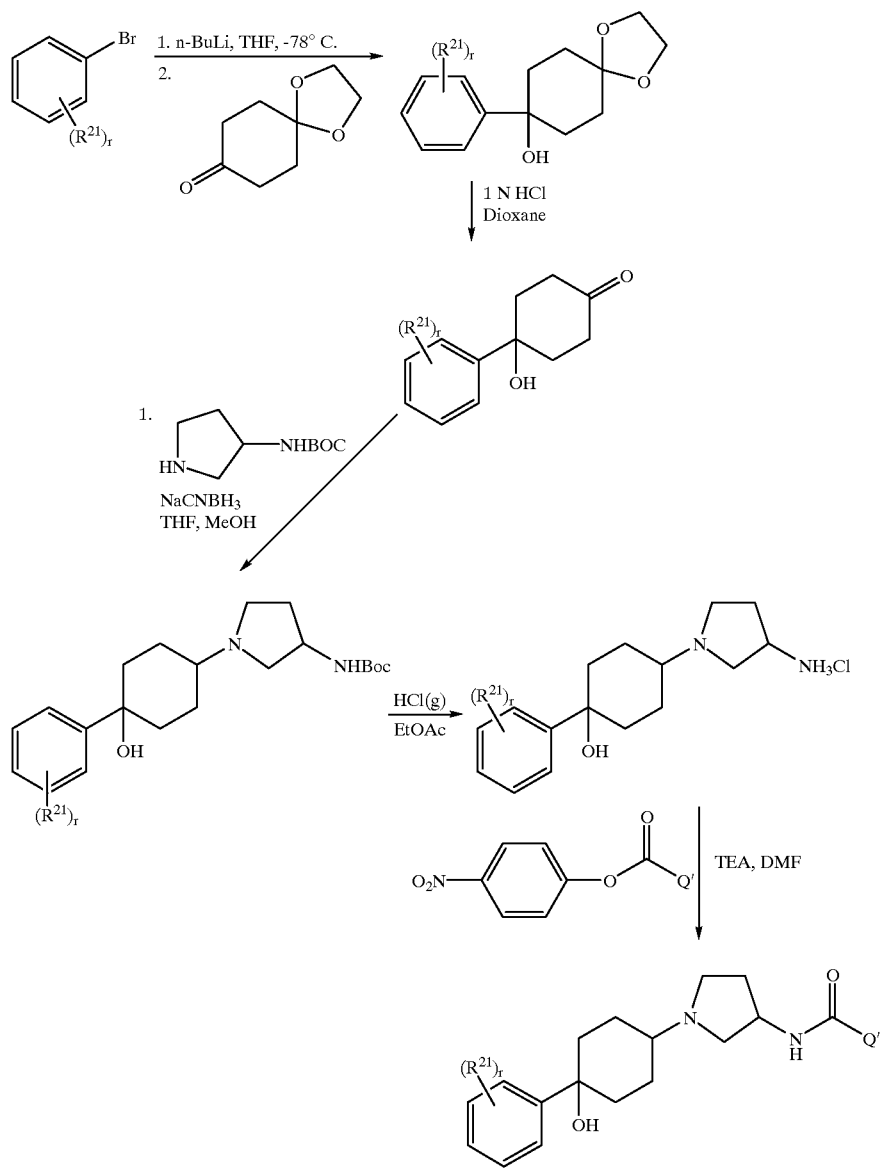

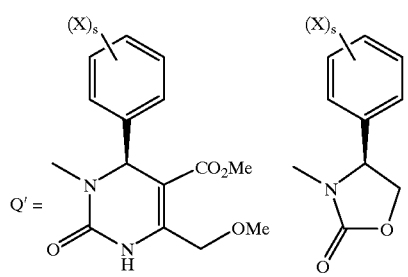
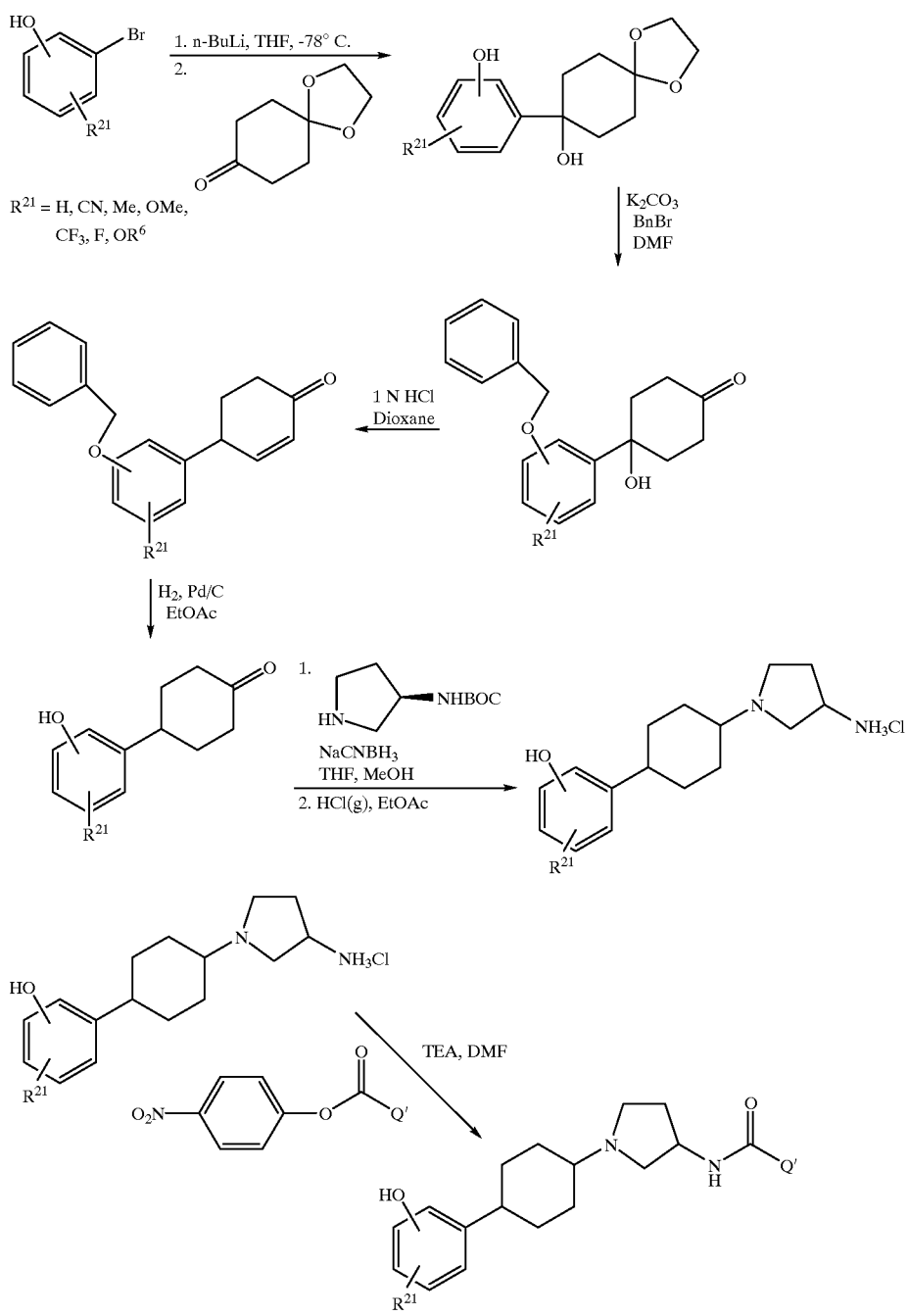
Scheme 13

-continued
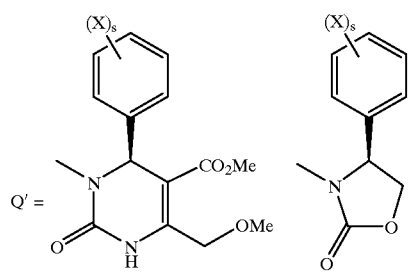
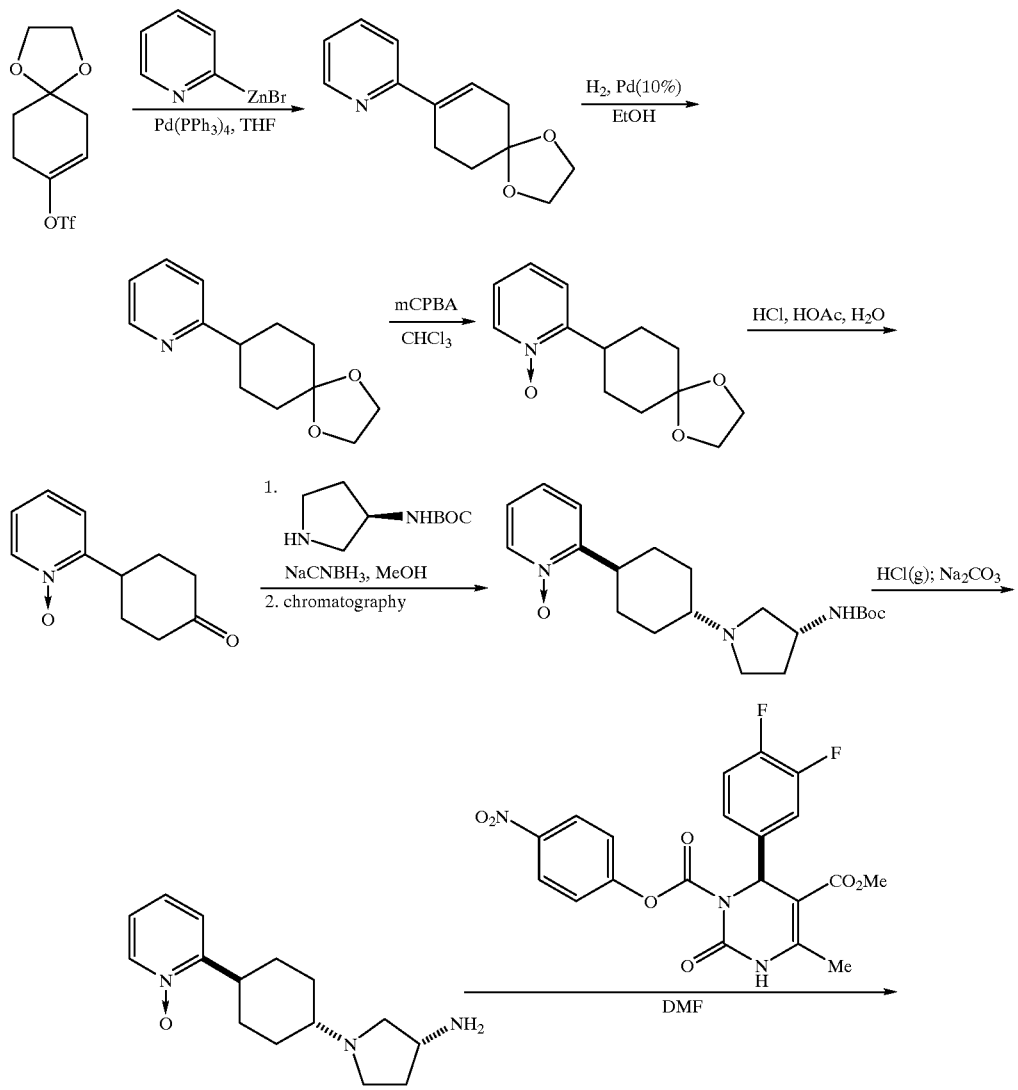
Scheme 14

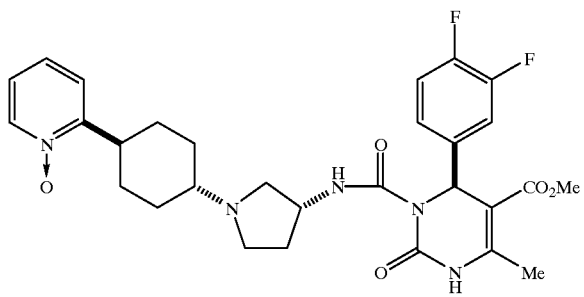
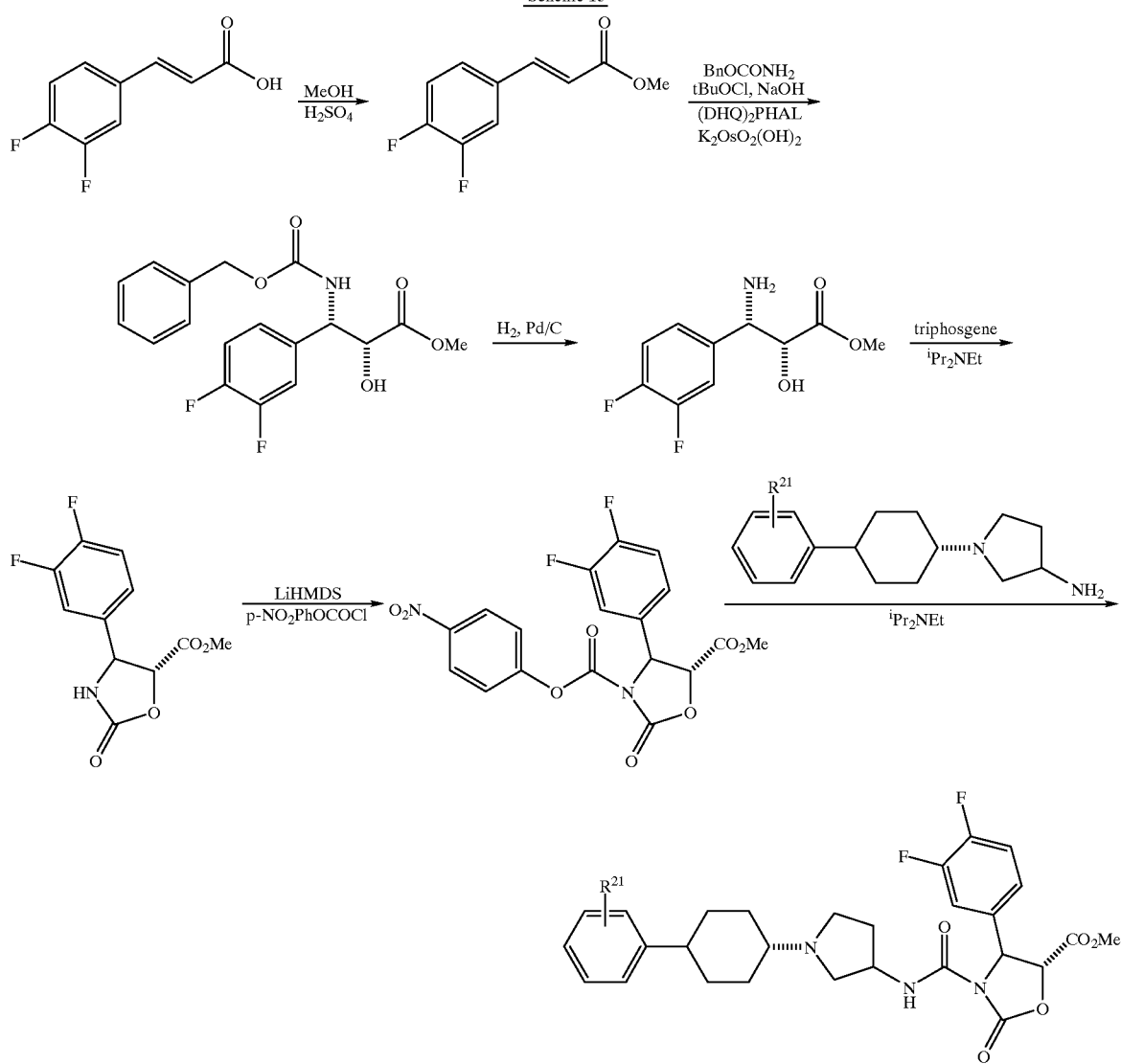

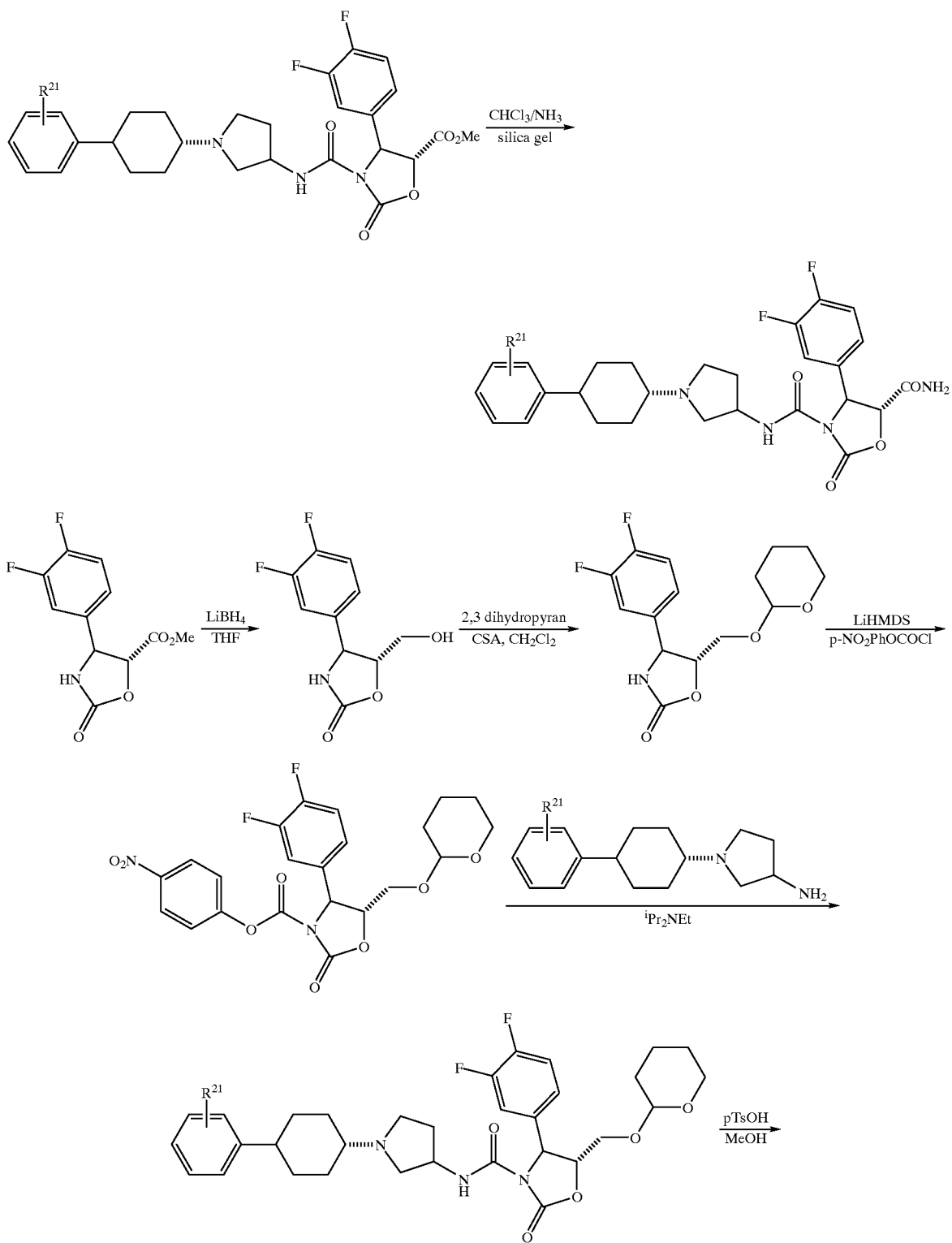

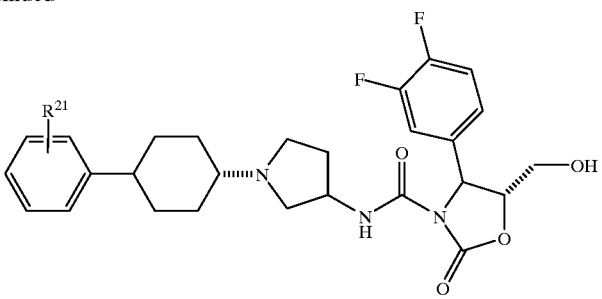
SCHEME 16
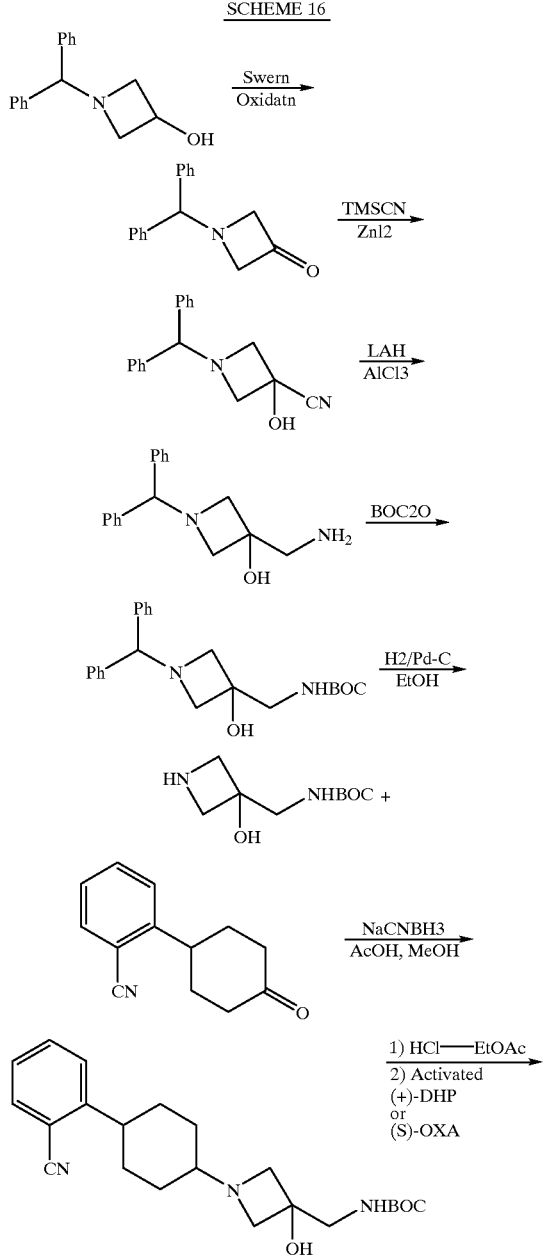
SCHEME 17
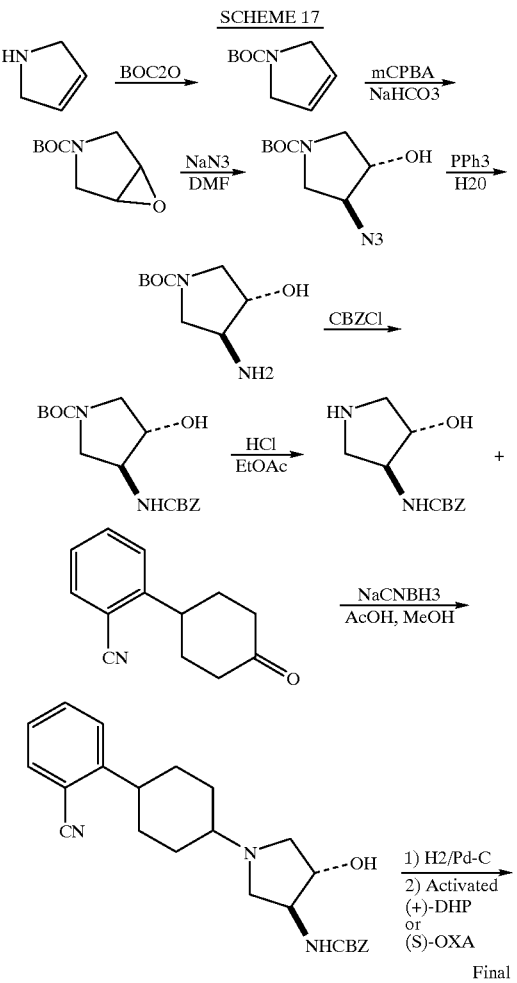
Final Products
The following examples are provided to further define the invention without, however, limiting the invention to the particulars of these examples.
Examples 1–12 were prepared according to Schemes 8 and 9.

EXAMPLE 1

(4S)-3-(1-[4-(2-Cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester hydrochloride

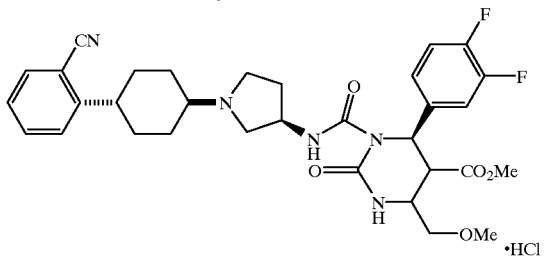

Step A: Trifluoromethanesulfonic acid 1,4-dioxa-spiro[4.5]dec-7-en-8yl ester

To a solution of diisopropylamine (7.6 mL, 54.3 mmol) in 200 mL THF cooled to −78° C. was added n-butyllithium (21.8 mL 2.5 M in hexane, 54.3 mmol) under argon. The solution was stirred for 10 minutes, then a solution of 1,4-cyclohexanedione monoethylene ketal (8.5 g, 54.3 mmol) in 75 mL THF was added slowly. The solution was stirred for 10 min, then a solution of N-phenyltrifluoromethane sulfonamide (19.5 g, 54.3 mmol) in 150 mL THF was added slowly. The reaction solution was warmed to r.t., poured onto saturated sodium bicarbonate, and extracted with ethyl acetate. The combined organic layers were washed with saturated sodium chloride, dried with magnesium sulfate, and concentrated in vacuo. The crude material was passed through silica (3% methanol, dichloromethane) to give the product as an oil.

$^1$H NMR $\delta_H$ (CDCl$_3$) 5.7–5.6 (m, 1H), 4.1–4.0 (m, 4H), 2.6–2.5 (m, 2H), 2.5–2.4 (m, 2H), 1.9 (t, 2H, J 6.6).

Step B: 2-(1,4-Dioxaspiro[4.5]dec-7-en-8-yl)benzonitrile

To a solution of trifluoromethanesulfonic acid 1,4-dioxaspiro[4.5]dec-7-en-8-yl ester (12.5 g, 45.2 mmol) in THF (100 mL) at room temperature was added a solution of iodozinc benzonitrile (100 mL of a 0.5 N solution in THF, 50 mmol) and palladium tetrakistriphenylphophine (1 g, 0.8 mmol). The reaction was heated to 80° C. for 1 hour. The reaction was cooled to room temperature and poured into saturated sodium bicarbonate (1L), and extracted with ethyl acetate. The combined organic layers were washed with saturated sodium chloride, dried with magnesium sulfate, and concentrated in vacuo. The crude material was chromatographed over silica gel eluting with 25% ethylacetate/hexane to give the product as a pale yellow oil.

$^1$H NMR $\delta_H$ (CDCl$_3$) 7.7–7.6 (m, 1H), 7.52 (dt, 1H, J=2, 7 Hz),7.4–7.26 (m, 2H), 5.95–5.88 (m, 1H), 4.05–4.0 (m, 4H), 2.7–2.6 (m, 2H), 2.55–2.48 (m, 2H), 1.95 (t, 2H, J=6.6 Hz).

Step C: 2-(1,4-Dioxaspiro[4.5]dec -8-yl)benzonitrile

To a suspension of 10% palladium on carbon (1.5 g) in ethyl acetate (200 mL) at room temperature under argon was added a solutioin of 2-(1,4-Dioxaspiro[4.5]dec-7-en-8-yl)benzonitrile (8.9 g, 36.7 mmol) in ethyl acetate (50 mL). Hydrogen gas was then bubbled into the reaction mixture until all the starting material was consumed. The reaction was filtered through celite to remove the catalyst and the solution concentrated to give the product as a colorless oil.

$^1$H NMR $\delta_H$ (CDCl$_3$) 7.65–7.6 (m, 1H), 7.54 (dt, 1H, J=2, 7 Hz),7.46 (br d, 2H, J=7 Hz), 7.28 (dt, 1H, J=2, 7 Hz), 4.05–4.0 (m, 4H), 3.1–3.0 (m, 1H), 2.0–1.7 (m, 8H)

Step D: 2-(4-Oxocyclohexyl)benzonitrile

To a stirring solution of 2-(1,4-Dioxaspiro[4.5]dec -8-yl)benzonitrile (8.7 g, 35.7 mmol) in dioxane (200 mL) was added 1N HCl (200 mL) and the reaction heated to 80° C. for 2 hours. The reaction was cooled to room temperature and poured into water (1 L) the mixture was extracted with ethyl acetate (3×250 mL). The combined organics were washed with brine (200 mL) and then dried over anhydrous magnesium sulfate, filtered and concentrated at reduced pressure to give the product.

$^1$H NMR $\delta_H$ (CDCl$_3$) 7.65–7.6 (br d, 1H, J=7 Hz), 7.59 (br t, 1H, J=7 Hz),7.40–7.30 (m, 2H), 3.5 (tt, 1H, J=3, 10 Hz), 2.7–2.5 (m, 4H), 2.35–2.2 (m, 2H), ), 2.05–1.90 (m, 2H)

Step E: cis and trans 2-[4-(3R-3-Amino-pyrrolidini-1-yl)-cyclohexyl]-benzonitrile dihydrochloride To a solution of 2-(4-Oxocyclohexyl)benzoritrile (0.921 g, 4.63 mmol) and acetic acid (1.0 mL 17.5 mmol) in 30 mL methanol was added (3R)-(+)-3-(tert-butoxycarbonylamino)-pyrrolidine (1.29 g, 6.95 mmol) under argon. The solution was stirred for 2 h, then sodium cyanoborohydride (6.95 mL 1M in THF, 6.95 mmol) was added dropwise. The solution was poured onto saturated sodium bicarbonate, and extracted with ethylacetate. The combined organic layers were washed with saturated sodium chloride, dried with magnesium sulfate, and concentrated in vacuo. The crude material was passed through silica (5% methanol, ethylactate) to give 2:1 trans:cis 2-[4-(3-tertbutoxycarbonylamino-pyrrolidin-1-yl)-cyclohexyl]-benzonitrile. The trans-2-[4-(3-tertbutoxycarbonylamino-pyrrolidin-1-yl)-cyclohexyl]-benzonitrile (1.1 g, 2.98 mmol) was dissolved in 100 mL ethylacetate, and HCl gas was bubbled through the solution for 30 min. The solution was concentrated in vacuo to give the trans product.

$^1$H NMR $\delta_H$ (CDCl$_3$) 7.75–7.60 (m, 2H), 7.55–7.45 (m, 1H), 7.40–7.35 (m, 1H), 4.20–3.20 (m, 7H), 3.15–3.00 (m, 2H), 2.80–2.50 (m, 1H), 2.40–2.00 (m, 5H), 1.90–1.60 (m, 4H).

The cis-2-[4-(3-tert-butoxycarbonylamino-pyrrolidin-1-yl)-cyclohexyl]-benzonitrile (0.60 g, 1.6 mmol) was dissolved in 100 mL ethylacetate, and HCl gas was bubbled through the solution for 30 min. The solution was concentrated in vacuo, swished with hot ethyl acetate, and filtered to give the cis product $^1$H NMR $\delta_H$ (CDCl$_3$) 8.00–7.90 (m, 1H), 7.70–7.60 (m, 2H), 3.40–3.30 (m, 1H), 4.30–3.80 (m, 6H), 3.70–3.10 (m, 3H), 2.85–2.70 (m, 1H), 2.55–1.75 (m, 9H).

Step F: 3-{1-[4-(2-Cyano-phenyl)-cyclohexyl]-3R-pyrrolidin-3-ylcarbamoyl]-4-(3,4-difluoro-phenyl)-6-methoxymethyl-2-oxo-1,2,3,4-tetrahydropyrimidine-5-carboxylic acid methyl ester hydrochloride To a solution of trans-2-[4-(3R-3-Amino-pyrrolidin-1-yl)-cyclohexyl]-benzonitrile dihydrochloride (300 mg, 0.880 mmol) and triethylamine (0.37 mL, 2.64 mmol) in 3.0 mL DMF was added (+)-3-(4-nitrophenoxycarbonyl)-4-(3,4-difluorophenyl)-6-methoxymethyl-2-oxo-1,2,3,4-tetrahydropyrimidine-5-carboxylic acid methyl ester (462 mg, 0.968 mmol) under argon. The solution was stirred for 2 hour, poured onto saturated sodium bicarbonate, and extracted with ethylacetate. The combined organic layers were washed with saturated sodium chloride, dried with magnesium sulfate, and concentrated in vacuo. The crude material was passed through silica (3% methanol, dichloromethane) and washed with sodium carbonate. To a solution of the free base in ethylacetate was added excess hydrogen chloride (1M in diethylether). This solution was concentrated in vacuo to give the product.

Anal. Calcd. for $C_{32}H_{35}F_2N_5O_5 \cdot HCl$: C, 69.67; H, 5.63; N, 10.87. Found: C, 60.10; H, 5.13; N, 11.16%.

The following compounds were prepared by procedures substantially as described above for step F from either the cis or trans product of step E. In the case of Examples 3 and 4, the (+)-(S)-3-(4-nitrophenoxycarbonyl)-4-(3,4-difluorophenyl)-oxazolidin-2-one was substituted for the (+)-3-(4-nitrophenoxycarbonyl)-4-(3,4-difluorophenyl)-6- methoxymethyl-2-oxo-1,2,3,4-tetrahydropyrimidine-5-carboxylic acid methyl ester.

EXAMPLE 2

(4S)-cis-3-{1-[4-(2-Cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester hydrochloride

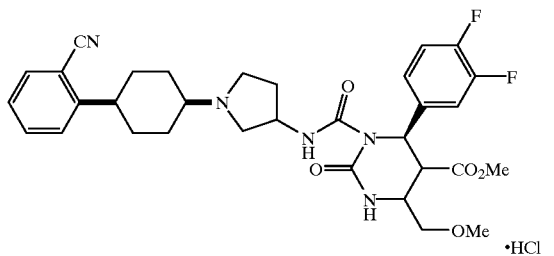

Analysis: Calcd. for $C_{32}H_{35}F_2N_5O_5 \cdot HCl \cdot 0.4\ H_2O$ C, 59.01; H, 5.70; N,10.75; Found: C, 59.04; H, 5.65; N,10.47.

EXAMPLE 3 trans-4S-4-(3,4-Difluorophenyl)-2-oxooxazolidine-3-carboxylic acid-{1-[4-(2-Cyano-phenyl)-cyclohexyl]-3R-pyrrolidin-3-yl}amide hydrochloride

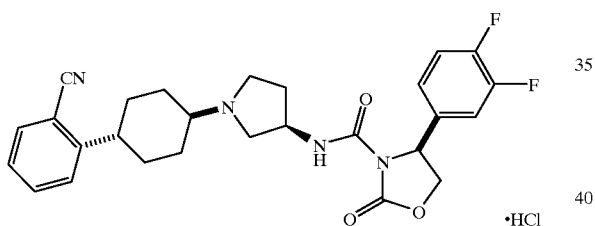

Analysis: Calcd. for $C_{27\ 28}F_2N_4O_3 \cdot HCl \cdot 0.2\ H_2O \cdot 0.25$ EtOAc; C, 60.41; H, 5.69; N,10.07; Found: C, 60.42; H, 5.62; N,10.10.

EXAMPLE 4

(4S)-cis-4-(3,4-Difluorophenyl)-2-oxooxazolidine-3-carboxylic acid-{1-[4-(2-Cyano-phenyl)-cyclohexyl]-(3R)-pyrrolidin-3-yl}amide hydrochloride

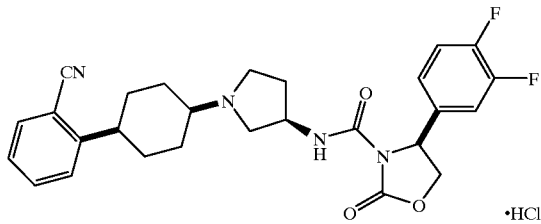

Analysis: Calcd. for $C_{27\ 28}F_2N_4O_3 \cdot HCl \cdot 0.1\ H_2O \cdot 0.95$ EtOAc; C, 60.00; H, 6.02; N,9.09; Found: C, 60.02; H, 5.75; N,9.06.

The following Examples were prepared by procedures substantialy as described above for Examples 1–4 except substituting the appropriate halozinc reagent (purchased from RIEKE Chemical) in step B.

EXAMPLE 5

(4S)-trans-4-(3,4-Difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester hydrochloride

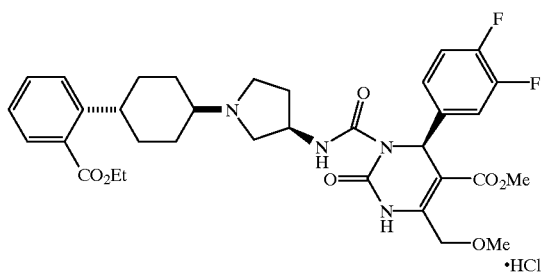

Analysis: Calcd. for $C_{34}H_{40}F_2N_4O_5 \cdot HCl \cdot 0.75\ H_2O \cdot 0.05$ EtOAc; C, 58.01; H, 5.96; N,7.91; Found: C, 57.89; H, 5.99; N,8.31.

EXAMPLE 6

(4S)-cis-4-(3,4-Difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester hydrochloride

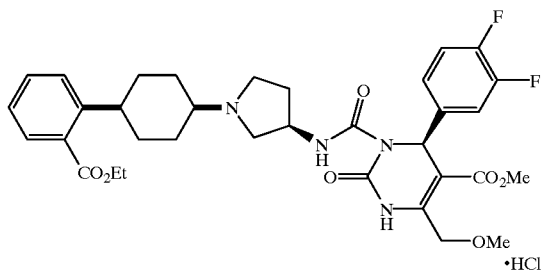

Analysis: Calcd. for $C_{34}H_{40}F_2N_4O_5 \cdot HCl \cdot 0.75\ H_2O \cdot 0.05$ EtOAc; C, 57.20; H, 6.16; N,7.80; Found: C, 57.21; H, 6.00; N,8.46.

EXAMPLE 7

(4S)-trans-4-(3,4-Difluorophenyl)-2-oxo-oxazolidine-3-carboxylic acid-{1-[4-(2-ethoxycarbonylphenyl)-cyclohexyl]-(3R)-pyrrolidin-3-yl}amide hydrochloride

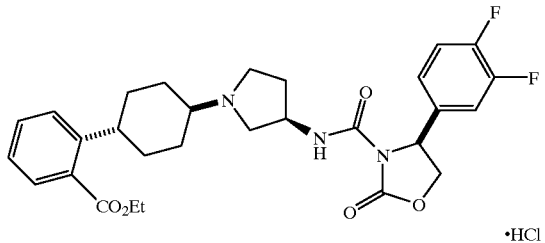

Analysis: Calcd. for $C_{29}H_{33}F_2N_3O_5 \cdot HCl \cdot 0.15\ H_2O \cdot 0.05$ EtOAc; C, 59.93; H, 5.98; N, 7.18; Found: C, 59.94; H, 5.78; N, 7.52.

EXAMPLE 8

(4S)-cis-4-(3,4-Difluorophenyl)-2-oxooxazolidine-3-carboxylic acid-{1-[4-(2-ethoxycarbonylphenyl)-cyclohexyl]-(3R)-pyrrolidin-3-yl}amide hydrochloride

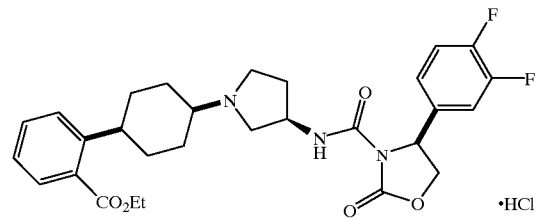

Analysis: Calcd. for $C_{29}H_{33}F_2N_3O_5 \cdot HCl \cdot 0.85\ H_2O \cdot 0.05$ EtOAc; C, 58.67; H, 6.09; N, 7.03; Found: C, 58.63; H, 5.86; N, 7.05.

EXAMPLE 9

(4S)-trans-4-(3,4-Difluorophenyl)-3-[1-(4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester

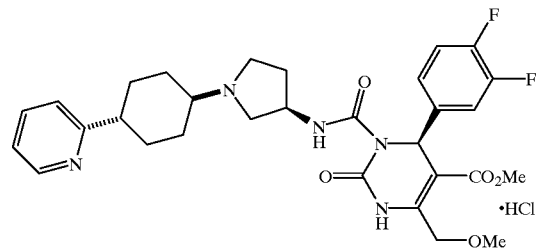

Analysis: Calcd. for $C_{30}H_{35}F_2N_5O_5 \cdot HCl \cdot 0.45\ H_2O \cdot 0.2$ EtOAc; C, 57.28; H, 6.01; N, 10.84; Found: C, 57.25; H, 5.73; N, 10.85.

EXAMPLE 10

(4S)-cis-4-(3,4-Difluorophenyl)-3-[1-(4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester

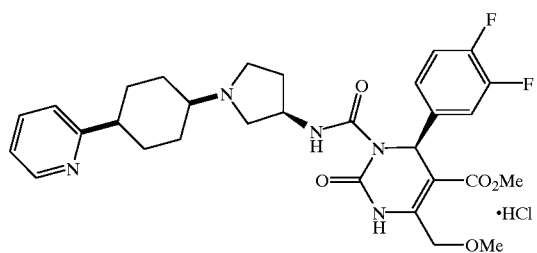

Analysis: Calcd. for $C_{30}H_{35}F_2N_5O_5 \cdot HCl \cdot 0.35$ EtOAc; C, 57.93; H, 6.01; N, 10.76; Found: C, 58.17; H, 5.80; N, 10.73.

EXAMPLE 11

(4S)-trans-4-(3,4-Difluorophenyl)-2-oxo-oxazolidine-3-carboxylic acid-[1-(4-pyridin-2-yl-cyclohexyl)-(3R)-pyrrolidin-3-yl]amide hydrochloride

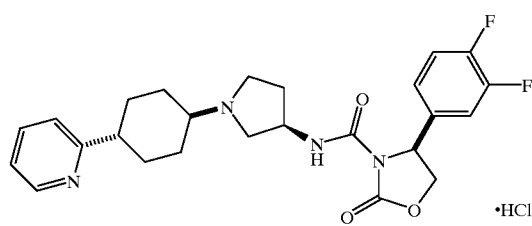

Analysis: Calcd. for $C_{25}H_{28}F_2N_4O_3 \cdot HCl \cdot 2.5\ H_2O \cdot 0.05$ EtOAc; C, 51.05; H, 6.02; N, 9.45; Found: C, 50.90; H, 5.30; N, 9.40.

EXAMPLE 12

(4S)-cis-4-(3,4-Difluorophenyl)-2-oxooxazolidine-3-carboxylic acid-[1-(4-pyridin-2-yl-cyclohexyl)-(3R)-pyrrolidin-3-yl]amide hydrochloride

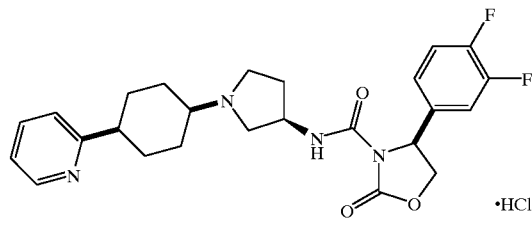

Analysis: Calcd. for $C_{25}H_{28}F_2N_4O_3 \cdot HCl \cdot 1.65\ H_2O \cdot 0.1$ EtOAc; C, 55.92; H, 6.12; N, 10.27; Found: C, 55.92; H, 5.85; N, 10.22.

Examples 13–17 were prepared according to Scheme 10.

EXAMPLE 13

(4S)-trans-4-(3,4-Difluorophenyl)-6-methoxymethyl-3-{1-[4-(2-methoxyl-phenyl)-cyclohexyl]-(3R)-pyrrolidin-3-ylcarbamoyl}-2-oxo-1,2,3,4-tetrahydro-pyrimidine-5-carboxylic acid methyl ester hydrochloride

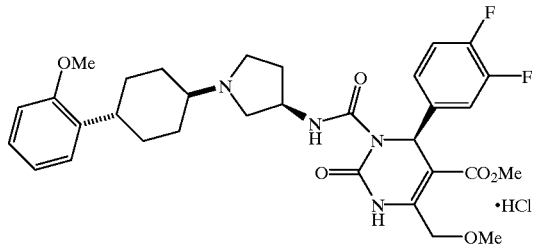

Step A: 8-(2-Methoxy-phenyl)-1,4-dioxa-spiro[4.5]decan-8-ol

To a solution of 2-Bromoanisole (1.87 g, 10.0 mmol) in 10 mL THF under Argon was added n-butyllithium (4.0 mL 2.5M in hexane, 10.0 mmol) cooled to −78° C. The solution was stirred 10 min. at −78° C., and a solution of 1,4-Cyclohexanedione mono-ethylene ketal (1.56 g, 10.0 mmol) in 10 mL THF was added slowly. The solution was warmed to r.t. and stirred for 60 min., then poured onto saturated sodium bicarbonate and extracted with ethylacetate. The combined organic layers were washed with saturated sodium chloride, dried with magnesium sulfate, and concentrated in vacuo. The crude solid was crystallized with hexane/diethylether 2:1 to give 8-(2-Methoxy-phenyl)-1,4-dioxaspiro[4.5]decan-8-ol as a white solid.

$^1$H NMR $\delta_H$ (CDCl$_3$) 7.4–7.2 (m, 2H), 7.0–6.9 (m, 2H), 4.1–3.9 (m, 4H), 3.9 (s, 3H), 2.3–2.0 (m, 6H), 1.7–1.6 (m, 2H).

Step B: 4-(2-Methoxy-phenyl)-cyclohex-3-enone and 4-(2-Methoxy-phenyl)-cyclohex-2-enone To a solution of 8-(2-Methoxy-phenyl)-1,4-dioxaspiro [4.5]decan-8-ol (100 mg, 0.379 mmol) in 10 mL THF was added HCl (1.4 mL 6M, 8.4 mmol). The solution was heated to 80° C. for 45 min, then poured onto saturated sodium bicarbonate and extracted with ethylacetate. The combined organic layers were washed with saturated sodium chloride, dried with magnesium sulfate, and concentrated in vacuo. The crude material was passed through silica (dichloromethane/3% methanol as eluent) to give 4-(2-Methoxy-phenyl)-cyclohex-3-enone $^1$H NMR $\delta_H$ (CDCl$_3$) 7.3–7.1 (m, 2H), 7.0–6.9 (m, 2H), 5.9–5.8 (m, 1H), 3.9–3.8 (s, 3H), 3.1–3.0 (m, 2H), 2.9–2.8 (m, 2H), 2.7–2.5 (m, 2H) and 4-(2-Methoxy-phenyl)-cyclohex-2-enone.

$^1$H NMR $\delta_H$ (CDCl$_3$) 7.3–7.2 (m, 1H), 7.2–7.1 (m, 1H), 7.0–6.9 (m, 3H), 6.2–6.1 (m, 1H), 4.2–4.1 (m, 1H), 3.8 (s, 3H), 2.6–2.4 (m, 2H), 2.4–2.2 (m, 1H), 2.1–1.9 (m, 1H).

Step C: 4-(2-Methoxy-phenyl)-cyclohexanone

To a suspension of palladium on carbon (3.75 g, 25% wt) in 200 mL ethylacetate was added a 1:2 mixture of 4-(2-Melhoxy-phenyl)-cyclohex-3-enone and 4-(2-Methoxy-phenyl)-cyclohex-2-enone (15 g, 75.0 mmol) under argon. The suspension was stirred under a hydrogen at 1 atm. for 6.5 h, filtered through celite,concentrated in vacuo, and crystallized from ethylacetate to give 4-(2-Methoxy-phenyl)-cyclohexanone.

$^1$H NMR $\delta_H$ (CDCl$_3$) 7.3–7.1 (m, 2H), 7.0–6.9 (m, 2H), 3.88 (s, 1H), 3.6–3.4(m, 1H), 2.6–2.4 (m, 4H), 2.3–2.2 (m, 2H), 2.0–1.8 (m, 2H).

The title compound of Example 13 was prepared from the product of step C by procedures identical to that described above for EXAMPLE 1 Steps E+F.

trans-4-(3,4-Difluoro-phenyl)-6-methoxymethyl-3-{1-[4-(2-methoxyl-phenyl)-cyclohexyl]-3R-pyrrolidin-3-ylcarbamoyl}-2-oxo-1,2,3,4-tetrahydro-pyrimidine-5-carboxylic acid methyl ester hydrochloride Analysis Calcd. for $C_{32}H_{38}F_2N_4O_6 \cdot HCl \cdot 0.45\ H_2O$; C, 58.56; H, 5.98; N, 8.54; Found: C, 58.55; H, 6.59; N, 8.15.

The following Examples were prepared from the product of step C above by procedures substantially as described above for Example 1 steps E+F.

EXAMPLE 14

(4S)-cis-4-(3,4-Difluoro-phenyl)-6-methoxymethyl-3-{1-[4-(2-methoxyl-phenyl)-cyclohexyl]-(3R)-pyrrolidin-3-ylcarbamoyl}-2-oxo-1,2,3,4-tetrahydro-pyrimidine-5-carboxylic acid methyl ester hydrochloride

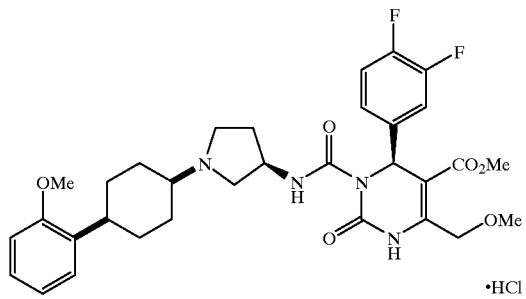

Analysis: Calcd. for $C_{32}H_{38}F_2N_4O_6 \cdot HCl \cdot 0.7\ H_2O$; C, 57.96; H, 6.25; N, 8.19; Found: C, 58.66; H, 6.05; N, 8.19.

EXAMPLE 15

(4S)-trans-4-(3,4-Difluorophenyl)-2-oxooxazolidine-3-carboxylic acid-{1-[4-(2-methoxyphenyl)-cyclohexyl]-(3R)-pyrrolidin-3-yl}amide hydrochloride

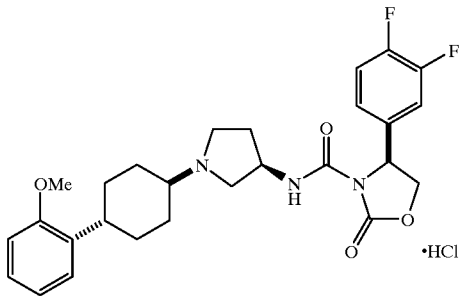

Analysis: Calcd. for $C_{32}H_{38}F_2N_4O_6 \cdot HCl \cdot 0.7\ H_2O \cdot 0.25$ EtOAc; C, 60.42; H, 5.69; N,10.07; Found: C, 60.42; H, 5.62; N,10.10.

EXAMPLE 16

(4S)-cis-4-(3,4-Difluorophenyl)-2-oxooxazolidine-3-carboxylic acid-{1-[4-(2-methoxyphenyl)-cyclohexyl]-(3R)-pyrrolidin-3-yl}amicLe hydrochloride

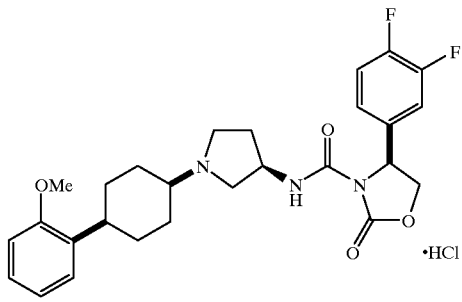

Analysis: Calcd. for C₃₂H₃₈F₂N₄O₆•HCl•0.1 H₂O•0.95 EtOAc; C, 60.00; H, 6.02; N,9.09; Found: C, 60.02; H, 5.75; N,9.06.

Examples 17–20 prepared according to Scheme 11.

EXAMPLE 17

(4S)-cis-4-(3,4-Difluoro-phenyl)-3-[1-(4-hydroxy-4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester hydrochloride

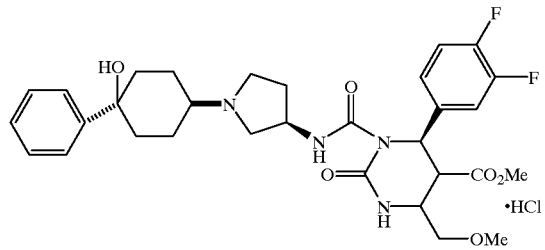

Step A: 8-(2-Pyridyl)-1,4-dioxaspiro[4,5]decan-8-ol

To a solution of 2-bromo-pyridine (10 g, 63.3 mmol) in tetrahydrofuran (200 mL) at −78° C. under an argon atmosphere was added a solution of n-butyllithium (26 mL of 2.5N solution, 65 mmol). The solution was stirred at −78° C. for 10 minutes and then a solution of cyclohexanedione monoethylene ketal (10 g, 64 mmol) in tetrahydrofuran(50 mL) was added. The reaction was allowed to warm to room temperature and poured into a saturated solution of sodium bicarbonate (mL) the mixture was extracted with ethyl acetate. The combined ethyl acetate fractions were dried over anhydrous sodium sulfate, filtered, and concentrated at reduced pressure. The residue was chromatographed over silica gel eluting with 25% to 50% ethyl acetate/hexane to give the product.

¹H NMR (CDCl₃, 300 MHz) δ 8.5 (m, 1H), 7.69 (dt, J=2, 7.5 Hz, 1H), 7.40 (dt, J=7.5, 1 Hz, 1H), 7.2 (ddd, J=1.5, 4.5, 7 Hz, 1H), 5.25 (s, 1H ex), 4.0 (m, 4H), 2.3–2.0 (m, 4H), 1.8–1.65 (m, 4H).

Step B: 4-Hydroxy-4-(2-pyridyl)-cyclohexanone

A solution of the product of step A (8-(2-pyridyl)-1,4-dioxaspiro[4,5]decan-8-ol)(8.3 g, 35.5 mmol) in dioxane (150 mL) was treated with 6 N HCl (60 mL) and stirred at room temperature for 0.5 hr. The reaction was carefully poured into cold saturated sodium bicarbonate (1 L). The mixture was extracted with ethyl acetate (3×200 mL) and the combined extracts were dried over anhydrous sodium sulfate, filtered, and concentrated at reduced pressure to give 5.3 g of the product.

¹H NMR (CDCl₃, 300 MHz) δ 8.6 (br d, 1H), 7.8–7.7 (m, 1H), 7.35 (d, J=5 Hz, 1H), 7.3–7.25 (m, 1H), 5.52 (s, 1H ex), 3.2–2.95 (m, 2H), 2.48–2.35 (m, 2H). 2.35–2.20 (m, 2H). 2.1–2.0 (m, 2H).

The title compound of Example 17 was prepared from the product of step B by procedures identical to those described above for EXAMPLE 1 Steps E+F Analysis Calcd. for C₃₀H₃₅F₂N₅O₆•HCl•0.1 H₂O; C, 58.94; H, 5.99; N,11.46; Found: C, 58.59; H, 5.59; N,11.24.

The following Examples were prepared from the product of step B above by procedures substantially as described above for Example 1 steps E+F.

EXAMPLE 18

(4S)-trans-4-(3,4-Difluoro-phenyl)-3-[1-(4-hydroxy-4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester hydrochloride

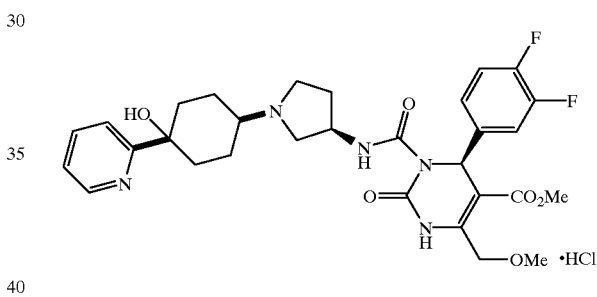

Analysis: Calcd. for C₃₀H₃₅F₂N₅O₆•HCl•0.55 H₂O•0.1CH₂Cl₂; C, 58.87; H, 5.83; N,11.39; Found: C, 58.88; H, 5.68; N,11.25.

EXAMPLE 19

(4S)-cis-4-(3,4-Difluorophenyl)-2-oxooxazolidine-3-carboxylic acid-[1-(4-hydroxy-4-pyridin-2-yl-cyclohexyl)-(3R)-pyrrolidin-3-yl]amide hydrochloride

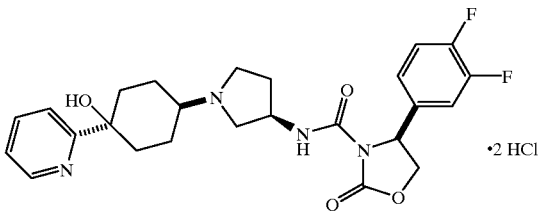

Analysis: Calcd. for C₂₅ ₂₈F₂N₅O₄•2 HCl•0.05 H₂O•0.25 EtOAc; C, 53.62; H, 5.56; N,9.62; Found: C, 54.30; H, 5.66; N,9.60.

EXAMPLE 20

(4S)-trans-4-(3,4-Difluorophenyl)-2-oxooxazolidine-3-carboxylic acid-[1-(4-hydroxy-4-pyridin-2-yl-cyclohexyl)-(3R)-pyrrolidin-3-yl]amide hydrochloride

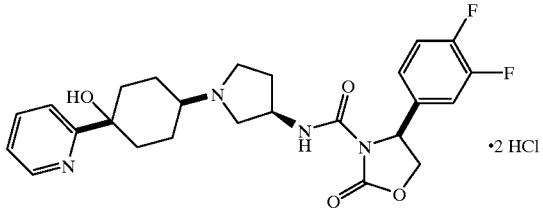

Analysis: Calcd. for $C_{25\ 28}F_2N_5O_4 \cdot 2$ HCl$\cdot$0.3 $H_2O \cdot$0.25 EtOAc; C, 53.21; H, 5.60; N,9.55; Found: C, 54.18; H, 5.57; N,9.29.

Examples 21–24 were prepared according to Scheme 13.

EXAMPLE 21

(4S)-4-(3,4-Difluoro-phenyl)-3-(1-[4-(2-hydroxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester

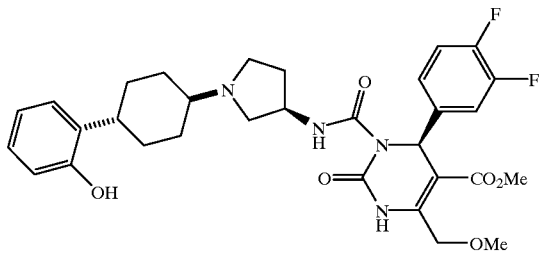

Step A: 8-(2-Benxyloxy-phenyl)-1,4-dioxa-spiro[4.5]decan-8-ol

To a solution of 8-(2-Hydroxy-phenyl)-1,4-dioxa-spiro [4.5]decan-8-ol (2.0 g, 7.9 mmol) in 10 mL DMF was added potassium carbonate (3.91 g, 28.3 mmol) and benzyl bromide (1.35 g, 1.9 mmol) under argon. The suspension was stirred for 1.6 h, poured onto 10% potassium hydrogen sulfate, and extracted with ethylacetate. The combined organic layers were washed with saturated sodium chloride, dried with magnesium sulfate, and concentrated in vaciio to give the product (2.76 g, 100%).

$^1$H NMR $\delta_H$ (CDCl$_3$) 8.02 (bs,1H), 7.45–7.35 (m, 2H), 7.25–7.20 (m, 2H), 7.05–6.95 (m, 1H), 5.18 (s, 2H), 4.00–3.90 (m, 4H), 2.20–2.10 (m, 4H), 1.70–1.60 (m, 4H).

Step B: 4-(2-Benzyloxy-phenyl)-4-hydroxy-cyclohexanone

To a solution of of 8-(2-Hydroxy-phenyl)-1,4-dioxa-spiro [4.5]decan-8-ol (2.76 g, 8.12 mmol) in 70 mL 1,4-dioxane was added aqueous hydrogen chloride (40.6 mL 1M, 40.6 mmol). The solution was stirred for 30 min., poured onto saturated sodium bicarbonate, and extracted with ethylacetate. The combined organic layers were washed with saturated sodium chloride, dried with magnesium sulfate, and concentrated in vacuo to give the product (1.96 g, 82%).

$^1$H NMR$\delta_H$ (CDCl$_3$) 7.35–7.25 (M, 2H), 7.10–7.00 (m, 2H), 5.20 (s, 2H), 4.44 (s, 1H), 3.00–2.85 (m, 2H), 2.55–2.40 (m, 2H) 2.35–2.15 (m, 4H).

Step C: 4-(2-Benzyloxy-phenyl)-cyclohex-3-enone and 4-(2-Benzyloxy-phenyl)-cyclohex-2-enone To a solution of 4-(2-Benzyloxy-phenyl)-4-hydroxy-cyclohexanone (1.9 g, 6.42 mmol) in 70 mL benzene was added p-toluenesulfonic acid monohydrate (0.070 g, 0.368 mmol). The solution was warmed to 60° C., stirred for 1 h, then poured onto saturated sodium bicarbonate, and extracted with ethylacetate. The combined organic layers were washed with saturated sodium chloride, dried with magnesium sulfate, and concentrated in vacuo to give a mixture of enone products (1.7 g, 100%).

$^1$H NMR $\delta_H$ (CDCl$_3$) 7.45–7.20 (m, 7H), 7.00–6.90 (m, 2H), 5.83 (s, 1H), 5.13 (s, 2H), 3.03 (bs, 2H), 2.83 (bt, 2H, J 6.35 Hz), 2.52 (bt, 2H, J 6.83).

Step D: 4-(2-Hydroxy-phenyl)-cyclohexanone

To a solution of a mixture of 4-(2-Benzyloxy-phenyl)-cyclohex-3-enone and 4-(2-Benzyloxy-phenyl)-cyclohex-2-enone (1.7 g, 6.12 mmol) in 25 mL ethylacetate under argon was added 10% palladium on carbon (0.425 g, 25 wt. %). The suspension was stirred under hydrogen at 1 atm. for 24 h, filtered through celite, and concentrated in vacuo to give the product (1.13 g, 97%).

$^1$H NMR $\delta_H$ (CDCl$_3$) 7.20–7.05 (m, 2H), 6.92 t, 1H, J 7.56 Hz), 6.75 (d, 1H, J 8.06 Hz), 3.35–3.45 (m, 1H), 2.65–2.45 (m, 4H), 2.30–2.20 (m, 2H), 2.0–1.85 (m, 2H).

The title compound of Example 21 was prepared from the product of step D by procedures identical to that described in EXAMPLE 1 Steps E+F.

Analysis Calcd. for $C_{31}H_{36}F_2N_5O_6 \cdot$0.9 $H_2O \cdot$0.4 $CH_2Cl_2$; C, 58.12; H, 6.00; N, 8.64; Found: C, 58.21; H, 5.72; N, 8.66.

The following examples were prepared from the product of step D above by procedures substantially as described above for Example 1 steps E+F.

EXAMPLE 22

(4S)-cis-4-(3,4-Difluoro-phenyl)-6-methoxymethyl-3-{1-[4-(2-hydroxy-phenyl)-cyclohexyl]-(3R)-pyrrolidin-3-ylcarbamoyl}-2-oxo-1,2,3,4-tetrahydro-pyrimidine-5-carboxylic acid methyl ester

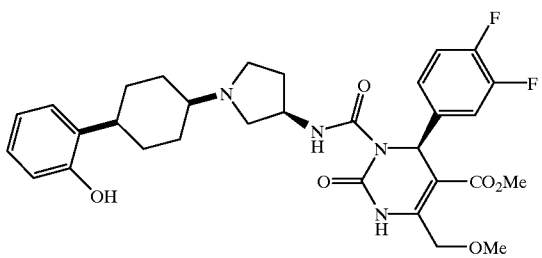

Analysis: Calcd. for $C_{31}H_{36}F_2N_5O_6 \cdot$0.4 $H_2O \cdot$0.1 $CH_2Cl_2$; C, 61.00; H, 5.76; N, 9.15; Found: C, 61.01; H, 5.77; N, 8.91.

EXAMPLE 23

(4S)-trans-4-(3,4-Difluorophenyl)-2-oxooxazolidine-3-carboxylic acid-{1-[4-(2-hydroxyphenyl)-cyclohexyl]-(3R)-pyrrolidin-3-yl}amide

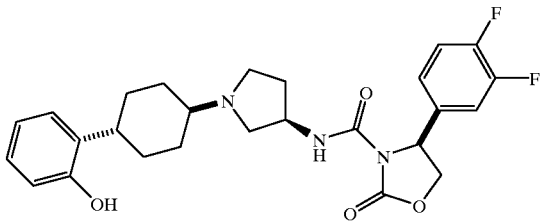

Analysis: Calcd. for $C_{26\ 29}F_2N_3O_4 \cdot 0.5\ H_2O \cdot 0.2\ CH_2Cl_2$; C, 61.50; H, 5.99; N, 8.22; Found: C, 61.42; H, 5.76; N, 8.32.

EXAMPLE 24

(4S)-cis-4-(3,4-Difluorophenyl)-2-oxooxazolidine-3-carboxylic acid-{1-[4-(2-hydroxyphenyl)-cyclohexyl]-(3R)-pyrrolidin-3-yl}amide

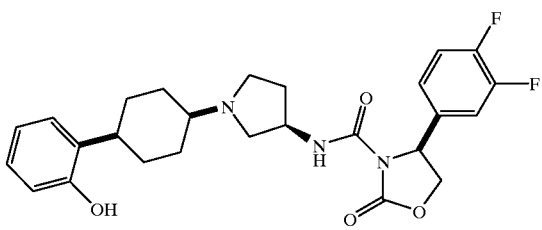

Analysis: Calcd. for $C_{26\ 29}F_2N_3O_4 \cdot 0.3\ H_2O \cdot 0.15\ CH_2Cl_2$; C, 62.35; H, 5.98; N, 8.34; Found: C, 62.73; H, 5.81; N, 8.30.

Utilizing the methodology described in detail herein, the following additional compounds shown in Tables 1–3 were prepared.

EXAMPLE 25

(4S)-trans-4-(3-,4-Difluorophenyl)-3-{1-[4-(2-fluorophenyl)-cyclohexyl]-(3R)-pyrrolidin-3-ylcarbamoyl}-6-methoxymethyl-1,2,3,4-tetrahydro-pyrimidine-5-carboxylic acid methyl ester hydrochloride

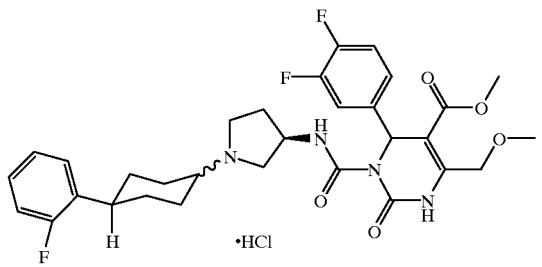

Step A: 8-(2-Fluorophenyl)-1,4-dioxa-spiro[4.5]decan-8-ol

To a solution of 2-fluoro-1-Iodobenzene (11.1 g, 50.0 mmol) in 50 mL THF, cooled to −78° C. under argon, was added n-butyllithium (20.0 mL 2.5M in hexane, 50.0 mmol). The solution was stirred 10 min. at −78° C., and a solution of 1,4-cyclohexanedione mono-ethylene ketal (7.81 g, 50.0 mmol) in 50 mL THF was added slowly. The solution was warmed to r.t. and stirred for 60 min., then poured onto saturated sodium bicarbonate and extracted with ethylacetate. The combined organic layers were washed with saturated sodium chloride, dried with magnesium sulfate, and concentrated in vacuo. The crude solid was crystallized from dichloromethane/hexane to give 8-(2-Fluoro-phenyl)-1,4-dioxa-spiro-[4.5]decan-8-ol (3.8 g, 30%).

$^1$H NMR δ (CDCl$_3$) 7.54–7.47 (m, 1H), 7.28–7.20 (m, 1H), 7.15–7.00 (m, 2H) 4.01 (s, 4H), 2.39–2.28 (m, 2H), 2.18–2.07 (m, 2H), 1.95 –1.85 (m, 2H), 1.75–1.60 (m, 2H).

Step B: 4-(2-Fluorophenyl)-4-hydroxy-cyclohexanone

To a solution of 8-(2-fluorophenyl)-1,4-dioxa-spiro[4.5] decan-8-ol (5.8 g, 23 mmol) in dioxane (100 mL), cooled to 0° C. was added hydrogen chloride (1M in water, 75 ml, 75 mmol). The reaction mixture was stirred for 2 hour at room temperature, extracted with ethyl ether (2×200 mL) and washed with saturated bicarbonate solution, water and brine. Drying and solvent evaporation gave 4-(2-Fluorophenyl)-4-hydroxy-cyclohexanone in quantitative yield.

$^1$H NMR (CDCl3) 1H NMR d (CDCl3) 7.60–7.50 (m, 1H), 7.40–7.00 (m, 3H), 3.0–2.8 (m, 2H), 2.6–2.3 (m, 4H), 2.3–2.2 (m, 2H).

Step C: 4-(2-Fluorophenyl)-cyclohexanone:

4-(2-Fluorophenyl)-4-hydroxy-cyclohexanone from Step B was added to trifluoroacetic acid at 0° C. and the reaction was stirred for 30 minutes and then poured onto saturated sodium bicarbonate and extracted with ethylacetate. The combined organic layers were washed with saturated sodium chloride, dried with magnesium sulfate, and concentrated in vacuo. to give the mixture of olefins, 4-(2-Fluorophenyl)-cyclohex-3-enone and 4-(2-Fluorophenyl)-cyclohex-2-enone (5.2 g).

To a suspension of palladium on carbon (1.1 g) in 100 mL ethylacetate was added the mixture of 4-(2-Fluoro-phenyl)-cyclohex-3-enone and 4-(2-Fluorophenyl)-cyclohex-2-enone (5.1 g) under argon. The suspension was placed under 50 psi hydrogen for 36 h, filtered through celite, concentrated in vacuo, and passed through silica (10% ethylacetate, hexane) to give 4-(2-fluorophenyl)-cyclohexanone (3.5 g).

$^1$H NMR δ$_H$ (CDCl$_3$) 7.29–7.20 (m, 2H), 7.15–7.04 (m, 2H), 3.44–3.34 (m, 1H), 2.64–2.41 (m, 4H), 2.26–2.21 (m, 2H), 2.06–2.01 (m, 2H).

Step D: cis and trans-1-[4-(2-Fluorophenyl)-cyclohexyl]-pyrrolidin-3-ylamine dihydrochloride To a solution of 4-(2-Fluorophenyl)-cyclohexanone (1.2 g, 6.25 mmol) and acetic acid (1.3 mL 22.75 mmol) in 30 mL methanol was added (3R)-(+)-3-(tert-butoxycarbonylamino)-pyrrolidine (1.74 g, 9.38 mmol) under argon. The solution was stirred for 2 h, then sodium cyanoborohydride (9.36 mL 1M in THF, 9.38 mmol) was added dropwise. The solution was poured onto saturated sodium bicarbonate, and extracted with ethylacetate. The combined organic layers were washed with saturated sodium chloride, dried with magnesium sulfate, and concentrated in vacuo. The crude material was passed through silica (3% methanol, ethylactate) to give 2:1 trans:cis 1-tertbutoxycarbonyl-[4-(2-fluoro-phenyl)-cyclohexyl] pyrrolidin-3-ylamine (2.3 g, 100%). The trans-1-tertbutoxycarbonyl-[4-(2-fluoro-phenyl)-cyclohexyl] pyrrolidin-3-ylamine (1.53 g, 4.23 mmol) was dissolved in 100 mL ethylacetate, and HCl gas was bubbled through the solution for 20 min. The solution was concentrated in vacuo to give trans-1-[4-(2-Fluorophenyl)-cyclohexyl]-pyrrolidin-3-ylamine dihydrochloride (1.4 g, 100%).

¹H NMR δ_H (CD₃OD) 7.31–7.26 (m, 2H), 7.29–7.03 (m, 2H), 4.15 (m, 1H), 3.90–3.45 (m, 2H), 3.42–3.25 (m, 2H), 3.0–2.85 (m, 1H), 2.70–2.45 (m, 1H), 2.40–2.20 (m, 2H), 2.05–2.02 (d, 2H, J=9.5 Hz), 1.79–1.67 (m, 4H

Step E: trans-4-(3-,4-Difluorophenyl)-3-{1-[4-(2-fluorophenyl)-cyclohexyl]-pyrrolidin-3-ylcarbamoyl}-6-methoxymethyl-1,2,3,4-tetrahydro-pyrimidine-5-carboxylic acid methyl ester hydrochloride To a solution of trans-1-[4-(2-fluoro-phenyl)-cyclohexyl]-pyrrolidin-3-ylamine dihydrochloride (100 mg, 0.299 mmol) and triethylamine (0.125 mL, 0.897 mmol) in 3.0 mL DMF was added (+)-3-(4-nitrophenoxycarbonyl)-4-(3,4-difluorophenyl)-6-methoxymethyl-2-oxo-1,2,3,4-tetrahydropyrimidine-5-carboxylic acid methyl ester (477 mg, 0.329 mmol) under argon. The solution was stirred for 2 h, poured onto saturated sodium bicarbonate, and extracted with ethylacetate. The combined organic layers were washed with saturated sodium chloride, dried with magnesium sulfate, and concentrated in vacuo. The crude material was passed through silica (3% methanol, dichloromethane) and washed with sodium carbonate. To a solution of the free base in ethylacetate was added excess hydrogen chloride (1M in diethylether). This solution was concentrated in vacuo to give the product (133 mg, 67%).

Analysis: Calcd. for $C_{31}H_{35}F_3N_4O_5$•HCl•0.55 $H_2O$; C, 57.54; H, 5.78; N, 8.66. Found: C, 57.58; H, 5.91; N, 8.79.

The compounds set forth in Examples 26–42 below were prepared by procedures substantially the same as described above in Example 25. Additional preparative details are provided in certain Examples as deemed appropriate.

EXAMPLE 26

(4S)-trans-4-(3,4-Difluoro-phenyl)-2-oxo-oxazolidine-3-carboxylic acid-{1-[4-(2-fluoro-phenyl)-cyclohexyl]-(3R)-pyrrolidin-3-yl}-amide hydrochloride

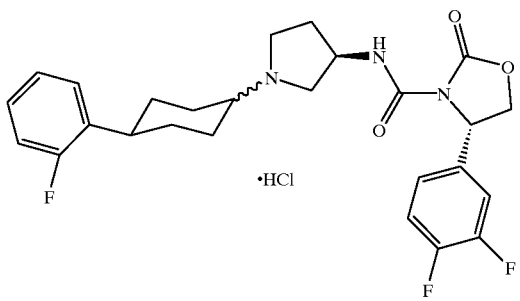

Analysis: Calcd. for $C_{31}H_{35}F_3N_4O_5$•HCl•0.35 EtOAc; C, 58.74; H, 5.76; N, 7.67; Found: C, 58.74; H, 5.82; N, 7.50.

EXAMPLE 27

(4S)-trans-4-(3,4-Difluoro-phenyl)-3-{1-[4-(4-fluoro-2-methoxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester hydrochloride

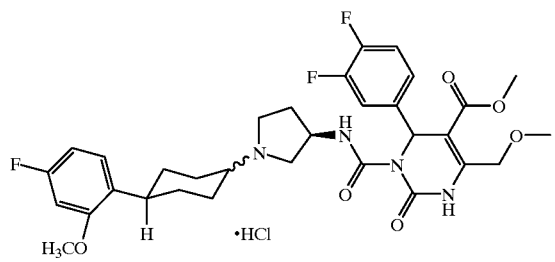

Analysis: Calcd. for $C_{32}H_{37}F_3N_4O_6$•HCl•1.35 $H_2O$•0.20 EtOAc; C,57.00; H, 6.32; N, 8.11; Found: C, 57.03; H, 5.95; N, 7.88.

EXAMPLE 28

(4S)-trans-4-(3,4-Difluoro-phenyl)-2-oxo-oxazolidine-3-carboxylic acid {1-[4-(4-fluoro-2-methoxy-phenyl)-cyclohexyl]-(3R)-pyrrolidin-3-yl}-amide hydrochloride

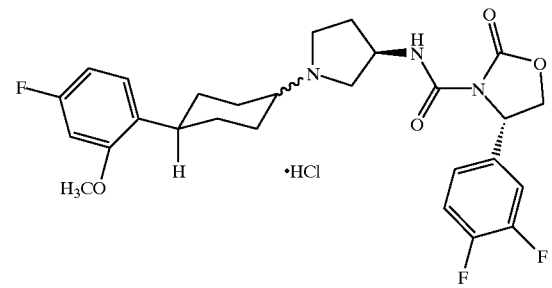

Analysis: Calcd. for $C_{27}H_{30}F_3N_3O_4$•HCl•0.40 $H_2O$•0.45 EtOAc; C,57.56; H, 5.94; N, 6.99; Found: C, 57.56; H, 5.68; N, 7.00.

EXAMPLE 29

(4S)- 4-(3,4-Difluoro-phenyl)-3-{1-[4-(2-fluoro-phenyl)-4-hydroxy-cyclohexyl]-(3R)-pyrrolidin-3-ylcarbamoyl}-6-methoxymethyl-1,2,3,4-tetrahydro-pyrimidine-5-carboxylic acid methyl ester hydrochloride Prepared from the product of Example 25, Step B by procedures similar to those described for Steps D and E of Example 25.

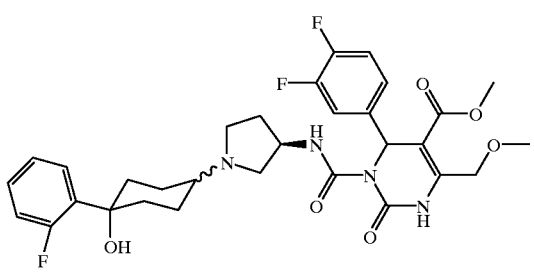

Analysis: Calcd. for $C_{31}H_{35}F_3N_4O_6 \cdot HCl \cdot 1.00\ H_2O \cdot 0.05$ ether; C,55.53; H,5.75; N, 8.30; Found: C, 55.53; H, 5.60; N, 8.34.

EXAMPLE 30

(4S)-4-(3,4-Difluoro-phenyl)-2-oxo-oxazolidine-3-carboxylic acid-(1-[4-(2-fluoro-phenyl)-4-hydroxy-cyclohexyl]-(3R)-pyrrolidin-3-yl}-amide hydrochloride

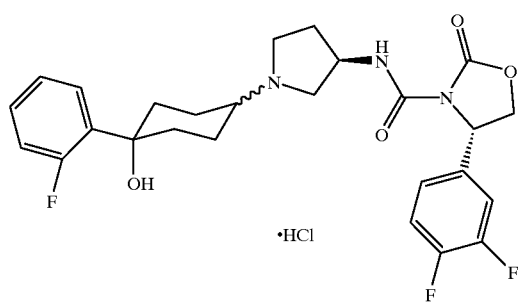

Analysis: Calcd. for $C_{26\ 28}F_3N_3O_4 \cdot HCl \cdot 0.40\ H_2O$; C,57.07; H, 5.49; N,7.68; Found: C,57.03; H, 5.32; N, 7.42.

EXAMPLE 31

(4S)-4-(3,4-Difluorophenyl)-2-oxo-oxazolidine-3-carboxylic acid {1-[4-hydroxy-4-(2-trifluoromethylphenyl)-cyclohexyl]-(3R)-pyrrolidin-3-yl} amide

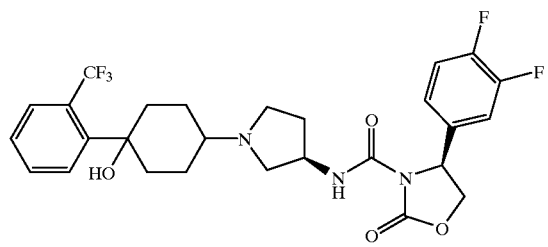

Analysis: Calculated for $C_{27\ 28}N_3O_4F_5 \cdot 0.15$ EtOAc: C, 58.49; H, 5.19; N, 7.41; Found: C, 58.50; H, 4.98; N, 7.13.

EXAMPLE 32

(4S)-4-(3,4-Difluorophenyl)-3-{1-[4-hydroxy-4-(2-trifluoromethylphenyl)-cyclohexyl]-(3R)-pyrrolidin-3-ylcarbamoyl}-6-methoxym ethyl-2-oxo-1,2,3,4-tetrahydropyrimidine-5-carboxylic acid methyl ester

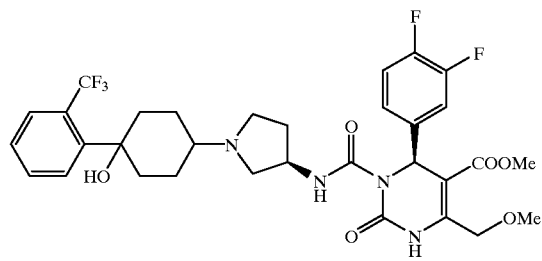

Analysis: Calculated for $C_{32}H_{35}N_4O_6F_5 \cdot 0.30$ EtOAc: C, 57.53; H, 5.44; N, 8.08; Found: C, 57.92; H, 5.43; N, 7.82.

EXAMPLE 33

(4S)-4-(3,4-Difluorophenyl)-2-oxo-oxazolidine-3-carboxylic acid {1-[4-(2-trifluoromethylphenyl)-cyclohexyl]-(3R)-pyrrolidin-3-yl} amide

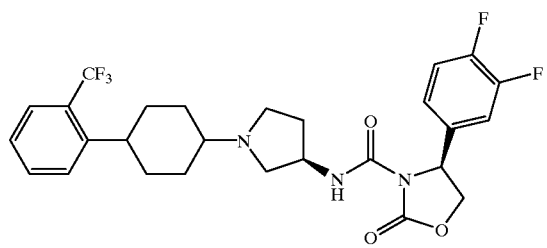

Analysis: Calculated for $C_{27\ 28}N_3O_3F_5$: C, 60.32; H, 5.26; N, 7.82 Found C, 60.36; H, 5.29; N, 7.50

EXAMPLE 34

(4S)-4-(3,4-Difluorophenyl)-6-methoxymethyl-2-oxo-3-{1-[4-(2-trifluoromethylphenyl)-cyclohexyl]-(3R)-pyrrolidin-3-ylcarbamoyl}-1,2,3,4-tetrahydropyrimidine-5-carboxylic acid methyl ester

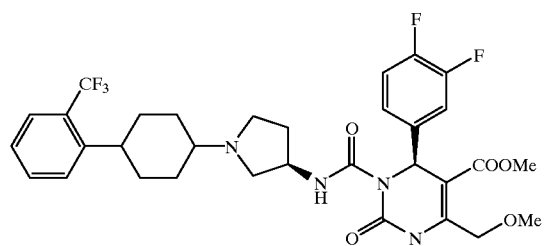

Analysis: Calculated for $C_{32}H_{35}N_4O_5F_5 \cdot 0.15\ CHCl_3$: C, 57.75; H, 5.30; N, 8.38; Found: C, 57.53; H, 5.30; N, 8.51.

EXAMPLE 35

(4S)-4-(3,4-Difluorophenyl)-3-{1-[4-(4-fluorophenyl)-4-hydroxy-cyclohexyl]-(3R)-pyrrolidin-3-ylcarbamoyl}-6-methoxymethyl-2-oxo-1,2,3,4-tetrahydropyrimidine-5-carboxylic acid methyl ester hydrochloride

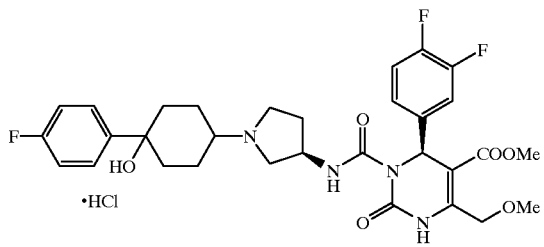

Step A.: 8-(4-Fluorophenyl)-1,4-dioxa-spiro[4.5]decan-8-ol

To a solution of 1,4-cyclohexanedione mono-ethylene ketal (25 g, 0.16 mol) in diethylether (750 ml), cooled to −78° C. was added 4-fluorophenyl magnesium bromide (1 M in tetrahydrofuran, 190 ml, 0.19 mol) dropwise. The reaction mixture was warmed to room temperature, quenched with water and extracted twice with ethyl acetate. Washing with brine, drying and solvent evaporation gave 8-(4-fluorophenyl)-1,4-dioxa-spiro[4.5]decan-8-ol (38 g, 95%).

$^1$H NMR (CDCl$_3$) δ 7.55–7.40 (m, 2H) 7.05–6.95 (m, 2H), 3.95 (m, 4H), 2.20–1.90 (m, 4H), 1.90–1.60 (m, 4H), 1.50 (s, 1H).

Step B: 4-(4-Fluorophenyl)-4-hydroxy-cyclohexanone

To a solution of 8-(4-fluorophenyl)-1,4-dioxa-spirc[4.5]decan-8-ol (38 g, 0.15 mol) in dioxane (900 ml), cooled to 0° C. was added hydrogen chloride (1M in water, 1.5 L, 1.5 mol). The reaction mixture was stirred for 2 hour at RT and extracted twice with ethyl acetate. The ethyl acetate layer was washed with saturated sodium bicarbonate solution, water and brine. Drying and solvent evaporation gave 4-(4-fluorophenyl)-4-hydroxy-cyclohexanone (24.8 g, 79%); $^1$H NMR (CDCl$_3$) δ 7.55–7.45 (m, 2H) 7.16–7.0 (m, 2H), 3.0–2.85 (m, 2H), 2.18–2.38 (m, 6H), 1.85 (s, 1H)

Step C: 4-(3-(3R)-tert-Butoxycarbonylamino-pyrrolidin-1-yl)-1-(4-fluorophenyl)-cyclohexanol

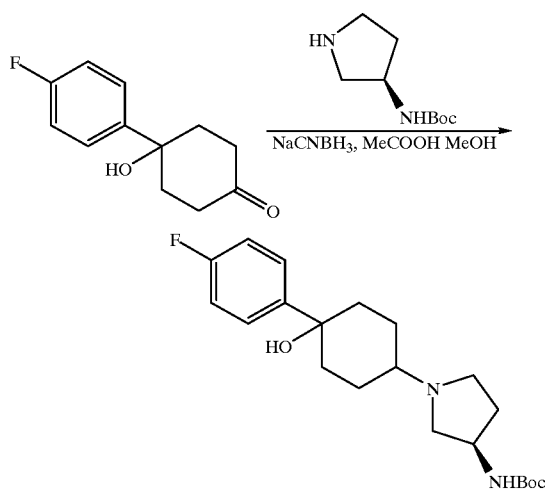

To a solution of 4-(4-Fluorophenyl)-4-hydroxy-cyclohexanone (2.0 g, 9.6 mmol) and acetic acid (2.6 ml, 48 mmol) in methanol (60 Ml) was added (3R)-(+)-3-(tert-butoxycarbonyl amino) pyrrolidine (2.6 g, 14.4 mmol). After stirring for 2 hours at room temperature, sodium cyanoborohydride (1M in tetrahydrofuran, 14.4 ml, 14.4 mmol) was added dropwise. The reaction mixture was stirred for 45 minutes, concentrated, diluted with 10% potassium hydrogen sulfate and extracted twice with ether. The aqueous solution was sasified with 1N sodium hydroxide and extracted with ethyl acetate three times. Washing with brine, drying and solvent evaporation gave an oil. Flash chromatography (silica gel, 2-propanol-ethyl acetate, 4:96 increasing to 8:92) gave 4-(3-(3R)-tert-Butoxycarbonylamino-pyrrolidin-1-yl)-1-(4-fluorophenyl)-cyclohexanol (2.0 g, 56%); $^1$H NMR (CDCl$_{13)}$ δ 7.46(m, 2H), 7.02 (m, 2H), 4.89 (m, 1H), 4.18 (m, 1H), 2.94 (m, 1H), 2.71 (m, 2H), 2.42 (m, 1H), 2.26 (m, 1H), 2.13 (m, 1H), 1.83 (m, 9H), 1.63 (m, 1H), 1.44 (s, 9H), A less polar isomer was also isolated.

Step D: 4-[(3R)-3-Aminopyrrolidin-1-yl]-1-(4-fluorophenyl)-cyclohexanol dihydrochloride

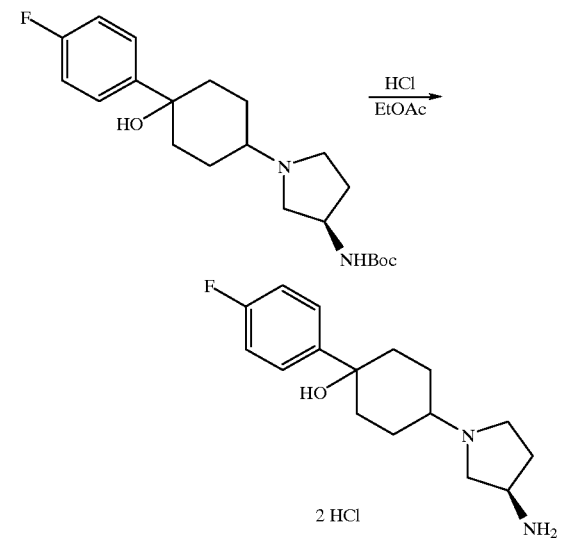

To a solution of 4-((3R)-3-tert-Butoxycarbonylamino-pyrrolidin-1-yl)-1-(4-fluorophenyl) cyclohexanol (1.05 g, 2.8 mmol) in ethyl acetate (50 ml), cooled to 0° C. was added hydrogen chloride gas, bubbled in gently for 5–10 minutes. The reaction mixture was stirred for 20 minutes at 0° C. and the above procedure was repeated twice. Concentration and flushing with ethyl acetate three times gave 4-((3R)-3-aminopyrrolidin-1-yl)-1-(4-fluorophenyl) cyclohexanol dihydrochloride (0.87 g, 89%); $^1$H NMR (DMSO) δ 11.33 (bd, 1H)), 8.60 (bd, 3H), 7.52 (m, 2H), 7.14 (m,2H), 5.12 (bs, 1H), 3.35–4.04 (m, 6H), 1.76–2.27 (m, 10H).

Step E: 4-(3,4-Difluorophenyl)-3-{1-[4-(4-fluorophenyl)-4-hydroxy-cyclohexyl]-(3R)-pyrrolidin-3-ylcarbamoyl}-6-methoxymethyl-1,2,3,4-tetrahydro-pyrimidine-5-carboxylic acid methyl ester hydrochloride was prepared by a procedure substantially as described above for the preparation of Example 25

Mass Spectrum: 617.4 (M+1), FAB

EXAMPLE 36

(4S)-4-(3,4-Difluorophenyl)-2-oxo-oxazolidine-3-carboxylic acid{1-[4-(4-fluorophenyl)-4-hydroxy-cyclohexyl]-(3R)-pyrrolidin-3-yl}amide

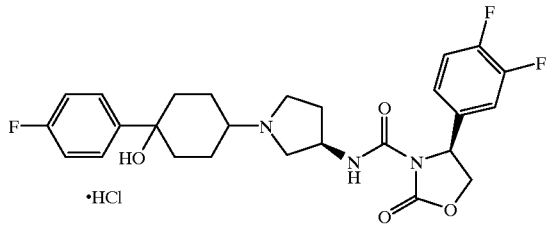

Mass Spectrum: 504.3 (M+1), FAB.

EXAMPLE 37

(4S)-4-(3,4-Difluorophenyl)-3-{1-[4-(4-fluorophenyl)-4-hydroxy-cyclohexyl]-(3R)-pyrrolidin-3-ylcarbamoyll-6-methy-2-oxo-1,2,3,4-tetrahydropyrimidine-5-carboxylic acid methyl ester hydrochloride

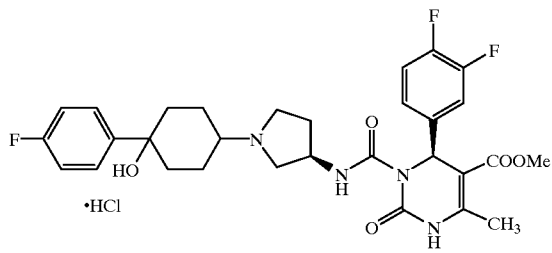

Analysis: Calculated for $C_{30}H_{33}N_4O_5F_3 \cdot HCl \cdot 1.5 H_2O$: C, 55.43; H, 5.74; N, 8.62; Found: C, 55.43; H, 5.48; N, 8.56.

EXAMPLE 38

(4S)-4-(3,4-Difluorophenyl)-3-{1-[4-(4-fluorophenyl)-cyclohexyl]-(3R)-pyrrolidin-3-ylcarbamoyl}-6-methyl-2-oxo-1,2,3,4-tetrahydropyrimidine-5-carboxylic acid methyl ester hydrochloride

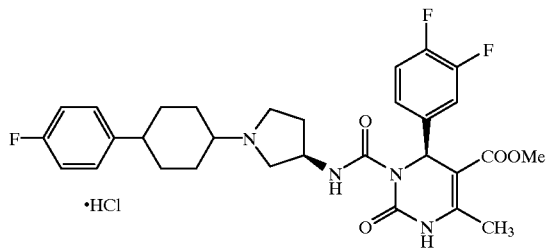

Analysis: Calculated for $C_{30}H_{33}N_4O_4F_3 \cdot HCl \cdot 0.75 H_2O$: C, 58.06; H, 5.77; N, 9.03; Found: C, 58.09; H, 5.90; N, 8.86.

EXAMPLE 39

(4S)-4-(3,4-Difluorophenyl)-3-{1-[4-(4-fluorophenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester hydrochloride

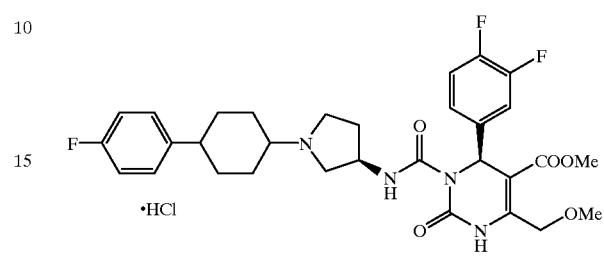

Analysis: Calculated for $C_{31}H_{35}N_4O_5F_3 \cdot HCl \cdot 0.45 H_2O$: C, 57.70; H, 5.76; N, 8.68 Found: C, 57.77; H, 5.75; N, 8.29

EXAMPLE 40

(4S)-4-(3,4-Difluorophenyl)-2-oxo-oxazolidine-3-carboxylic acid{1-[4-(4-fluorophenyl)-cyclohexyl]-(3R)-pyrrolidin-3-yl}amide

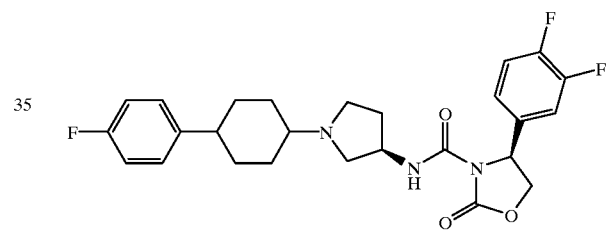

Analysis: Calculated for $C_{26}H^{28}N_3O_3F_3$: C, 64.04; H, 5.80; N, 8.62; Found: C, 63.93; H, 5.79; N, 8.58.

EXAMPLE 41

(4S)-4-(3,4-Difluorophenyl)-3-{1-[4-(4-fluorophenyl)-4-hydroxy-cyclohexyl]-(3R)-pyrrolidin-3-ylcarbamoyl}-2-oxo-1,2,3,4-tetrahydropyrimidine-5-carboxylic acid methyl ester

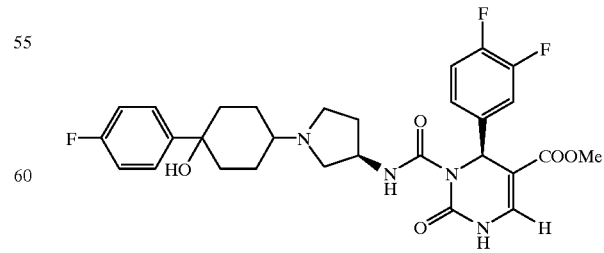

Analysis: Calculated for $C_{29}H_{31}N_4O_5F_3 \cdot 0.30$ $CHCl_3$: C, 57.84; H, 5.19; N, 9.21; Found: C, 57.95; H, 5.54; N, 8.92.

EXAMPLE 42

(4S)-3-{1-[4-(4-Cyanophenyl)-4-hydroxycyclohexyl]-(3R)-pyrrolidin-3-ylcarbamoyl}-4-(3,4-difluorophenyl)-6-methoxymethyl-2-oxo-1,2,3,4-tetrahydropyrimidine-5-carboxylic acid methyl ester hydrochloride

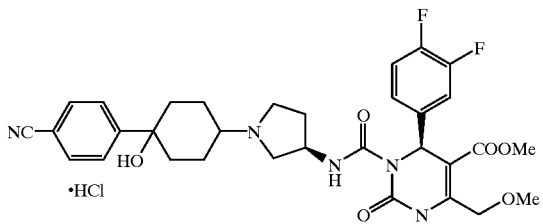

Analysis: Calculated for $C_{32}H_{35}N_5O_6F_2 \cdot HCl \cdot 0.75\ H_2O$: C, 57.05; H, 5.61; N, 10.40; Found: C, 56.75; H, 5.68; N, 10.79.

EXAMPLE 43

5-Cyclopropyl-4-(3,4-difluorophenyl)-2-oxo-oxazolidine-3-carboxylic acid {1-[4-(2-fluorophenyl)-cyclohexyl]-(3R)-pyrrolidin-3-yl-amide

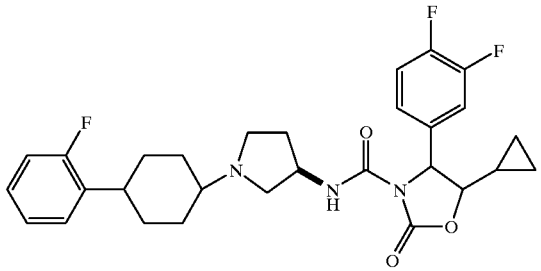

Step A 2-(3,4-difluorophenyl)-3-cyclopropyl-3-hydroxy-propionic acid

A solution of 3,4-difluorophenylacetic acid (2.9 g, 16.8 mmol) in 80 mL dry THF was cooled to −78° C. and treated with LDA (2.0 M heptane/THF/ethylbenzene, 42 mmol, 21 mL) for 15 minutes. Then cyclopropylcarboxaldehyde (17 mmol, 1.27 mL, 1.19 g) was added via syringe and the reaction warmed slowly to room temperature over 1 hr. The reaction mixture was diluted with 5% aqueous potassium hydrogen sulfate (50 mL), and extracted with ethyl acetate (2×150 mL). The combined extracts were dried (Na$_2$SO$_4$), filtered and concentrated in vacuo. The lower rf material crystallized to give 1.4 g of solid. $^1$H NMR (CDCl$_3$, 300 MHz) δ 7.40–7.00 (m, 3H, Ar—H), 3.75–3.60 (br m, 1H), 3.50–3.40 (m, 1H), 0.95–0.70 (m, 1H), 0.5–0.20 (m, 4H).

Step B 4-(3,4-difluorophenyl)-5-cyclopropyl-oxazolidin-2-one

The resulting hydroxy acids (7.95 g, 32 mmole) without further purification, were dissolved in dry degassed DMF (100 mL) and treated with solid NaHCO$_3$ (14.0 g) and diphenylphosphorylazide (DPPA, 9.9 g, 36 mmol, 7.74 mL) at room temperature for 1 hr. The reaction was then heated on a steam bath for 15 min. Signs of nitrogen evolution were immediately apparent. The reaction mixture was poured into saturated isodium bicarbonate and extracted with ethyl acetate. The organics were dried over anhydrous magnesium sulfate, filtered and concentrated in vacuo and purified by chromatography (SiO$_2$, 8 mm, 0–50% EtOAc/hexanes) affording the (±)-trans diastereomer (4.9 g) followed by the (±)-cis diastereomer (1.5 g). The trans isomer was resolved by HPLC on a Chiralcel OD eluting with 10% ethanol hexanes containing 1% diethylamine.

For the cis isomer.

$^1$H NMR (CDCl$_3$, 300 MHz) δ 7.35–7.20 (m, 2H, Ar—H), 7.10–7.05 (br m, 1H, Ar—H), 5.70 (br s, 1H, NH), 4.95 (d, 1H, J=7.5 Hz, CH(Ar)), 4.10 (t, 1H, J=7.5 Hz, CHcycpr), 0.6–0.50 (m, 1H), 0.5–0.4 (m, 1H), 0.4–0.3 (m, 1H), 0.2–0.1 (m, 1H).

For the trans isomer:

$^1$H NMR (CDCl$_3$, 300 MHz) δ 7.30–7.15 (m, 2H, Ar—H), 7.15–7.08 (br m, 1H, Ar—H), 5.85 (br s, 1H, NH), 4.75 (d, 1H, J=7.2 Hz, CH(Ar)), 3.65 (t, 1H, J=7.2 Hz, CHcycpr), 1.3–1.15 (m, 1H), 0.75–0.6 (m, 1H), 0.5–0.4 (m, 1H), 0.22–0.14 (m, 1H).

Step C 4-(3,4-Difluorophenyl)-5-cyclopropyl-2-oxo-oxazolidine-3-carboxylic acid-4-nitro-phenyl ester To a solution of 4-(3,4-difluorophenyl)-5-cyclopropyl-oxazolidin-2-one (2 g, 8.3 mmol) in 100 mL THF was added a solution of n-butyllithium in hexane (9.1 mmol) dropwise via a syringe under an argon atmosphere at −78° C. The resulting yellow solution was stirred at −78° C. for 10 min. To this solution was then added dropwise via syringe 4-nitrophenylchloroformate (1.03 g, 5.1 mmol) in 20 mL of THF. The reaction was stirred at −78° for 10 min. The reaction mixture was poured into saturated sodium bicarbonate and extracted with ethyl acetate (2×200 mL). The organic extracts were washed with brine, and the organic layer was dried over Na$_2$SO$_4$. The solvent was removed after filtration, and the residue was purified by column chromatography on silica gel 30% ethyl acetate hexane. The material was rechromatographed on silica gel eluting with 2% acetone/methylene chloride ti) give 1.2 g the product as a thick syrup which solidified upon standing.

$^1$H NMR (CDCl$_3$, 300 MHz) δ 8.22 (d, J=9.0 Hz, 2 H), 7.34 (d, J=9.0 Hz, 2 H), 7.35–7.05 (m, 3 H), 5.19 (d, J=5.0 Hz, 1 H),3.80 (dd, J=5.0,8.6 Hz, 1 H), 1.35–1.15 (m, 1H), 0.85–0.7 (m, 1H), 0.6–0.5 (m, 1H), 0.35–0.2 (m, 1H).

Step D.

5-cyclopropyl-4-(3,4-difluorophenyl)-2-oxo-oxazolidine-3-carboxylic acid {1-[4-(2-fluorophenyl)-cyclohexyl]-pyrrolidin-3-yl-amide The title compound was prepared from the reaction of the product of Step C above and trans-1-[4-(2-fluoro-phenyl)-cyclohexyl]-pyrrolidin-3-ylamine dihydrochloride

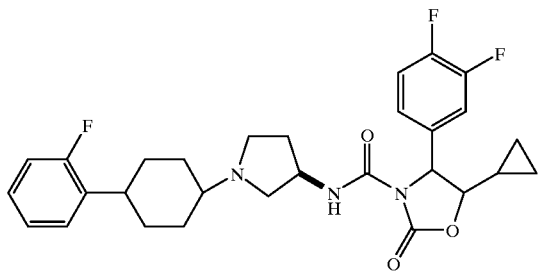

Calcd. for $C_{29}H_{32}N_3O_3F_3 \cdot 0.3\ H_2O$; 65.35 6.17 7.88; Found 65.38 6.02 8.05.

The compounds set forth in Examples 44 and 45 below were prepared by procedures substantially as described above for Example 43.

EXAMPLE 44

(4S, 5S)-5-Cyclopropyl-4-(3,4-difluorophenyl)-2-oxo-oxazolidine-3-carboxylic acid{1-[4-(4-fluorophenyl)-4-hydroxy-cyclohexyl]-(3R)-pyrrolidin-3-yl}amide hydrochloride This compound was prepared from the product of Example 35, Step D and the product of Example 43, Step C by a procedure similar to that described in Example 25, Step E.

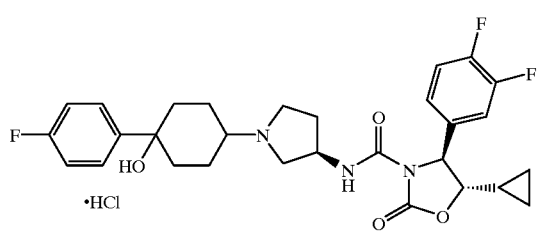

Analysis: Calculated for $C_{29}H_{32}N_3O_4F_3 \cdot HCl$: C, 60.04; H, 5.74; N, 7.24; Found: C, 59.74; H, 5.76; N, 7.45.

Mass Spectrum: 544.3 (M+1), FAB.

EXAMPLE 45

(4S, 5S)-5-Cyclopropyl-4-(3,4-difluorophenyl)-2-oxo-oxazolidine-3-carboxylic acid{1-[4-(4-cyanophenyl)-cyclohexyl]-(3R)-pyrrolidin-3-yl}amide

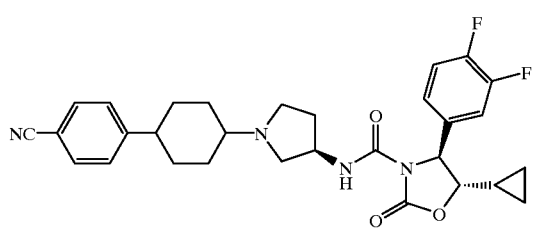

Analysis: Calculated for $C_{30}H_{32}N_4O_3F_2 \cdot 0.15\ CHCl_3$: C, 65.54; H, 5.87; N, 10.14; Found: C, 65.85; H, 5.80; N, 10.10.

The compounds set forth in Examples 46–64 below were prepared using procedures substantially the same as described in the preceding Examples.

EXAMPLE 46

(4S)-4-(3,4-difluorophenyl)-2-oxo-oxazolidine-3-carboxylic acid{1-[4-(4-cyanophenyl)-4-hydroxy-cyclohexyl]-(3R)-pyrrolidin-3-yl}amide hydrochloride

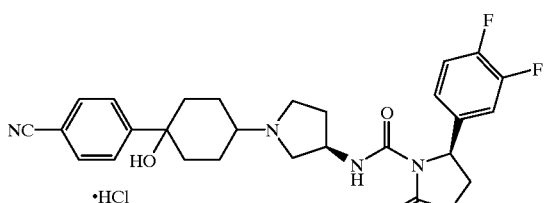

Analysis: Calculated for $C_{27\ 28}N_4O_4F_2 \cdot HCl \cdot 0.75\ H_2O$: C, 57.85; H, 5.48; N, 10.00; Found: C, 57.88; H, 5.79; N, 9.97.

EXAMPLE 47

(4S)-3-{1-[4-(4-Cyanophenyl)-cyclohexyl]-(3R)-pyrrolidin-3-ylcarbamoyl}-4-(3,4-difluorophenyl)-6-methyl-2-oxo-1,2,3,4-tetrahydropyrimidine-5-carboxylic acid methyl ester

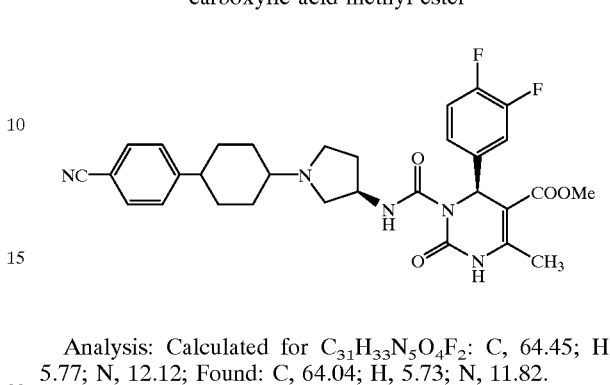

Analysis: Calculated for $C_{31}H_{33}N_5O_4F_2$: C, 64.45; H, 5.77; N, 12.12; Found: C, 64.04; H, 5.73; N, 11.82.

EXAMPLE 48

(4S)-trans-4-(3,4-Difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester

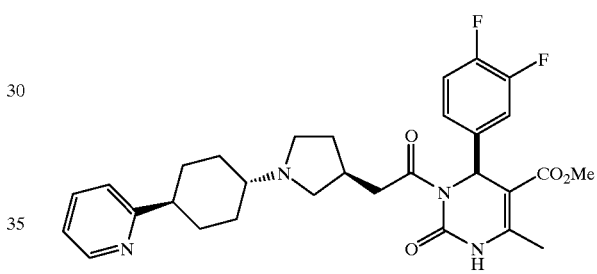

To a solution of dry acetonitrile (20 mL) containing 666 mg.(1.141 mmole) of trans-4-(3,4-difluorophenyl)-3-[1-(4-pyridin-2-yl-cyclo-hexyl)-3R-pyrrolidin-3-ylcarbamoyl]-6-methoxymethyl-2-oxo-1,2,3,4-tetrahydro-pyrimidine-5-carboxylic acid methyl ester (the preparation of which is described in Example 9) was added 0.676 ml (5.33 mmol) of chlorotrimethylsilane and 0.8 g (5.33 mmole) of sodium iodide. The reaction vessel was fitted with an efficient reflux condenser and the reaction mixture was heated to 65° C. for 30 minutes. The reaction mixture was subsequently heated to reflux for 30 minutes more. After one hour, an additional 5.33 mmole each of chlorotrimethylsilane and sodium iodide were added and then the same amount, once more, after three hours. The reaction was terminated after six hours. All volatiles were removed under reduced pressure and the residue was partitioned between ethyl acetate (200 mL) and water. The organic phase was washed with water and brine, then dried (sodium sulfate) and concentrated to yield an amorphous solid. The crude product was purified via preparative centrifugal chromatography (4 mm plate thickness, 2–20% methanol/chloroform gradient); repurification via preparative thick layer chromatography (1 mm plate thickness, 88:12:1.2 chloroform/methanol/conc. ammonium hydroxide elution, v/v) yielded 212 mg (34%) of the title compound in analytically pure form. This material was converted to its salt form with HCl (gas) in ethyl acetate:

HPLC=>99% pure at 215 nm & 255 nm. NMR(CDCl₃, 400 MHz): Consistent with structure assignment and con-

EXAMPLE 49

(4S)-3-{1-[4-(2-Cyano-phenyl)-cyclohexyl]-(3R)-pyrrolidin-3-ylcarbamoyl}-4-(3,4-difluoro-phenyl)-6-methyl-2-oxo-1,2,3,4-tetrahydro-pyrimidine-5-carboxylic acid methyl ester Hydrochloride

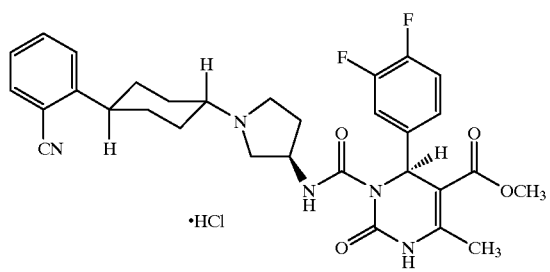

Analysis: Calcd. for $C_{31}H_{33}F_2N_5O_4 \cdot HCl \cdot 0.75\ H_2O$; C, 59.32; H, 5.70; N, 11.16; Found: C, 59.08; H, 5.89; N, 10.87.

EXAMPLE 50

(4S)-3-{1-[4-(2-Cyano-4-fluoro-phenyl)-cyclohexyl]-(3R)-pyrrolidin-3-ylcarbamoyl}-4-(3,4-difluoro-phenyl)-6-methoxymethyl-2-oxo-1,2,3,4-tetrahydro-pyrimidine-5-carboxylic acid methyl ester Hydrochloride

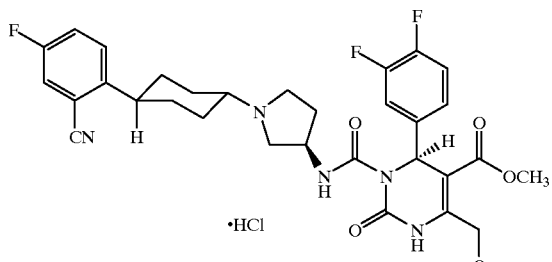

Analysis: Calcd. for $C_{32}H_{34}F_3N_5O_5 \cdot HCl \cdot 1.5\ H_2O$; C, 55.77; H, 5.56; N, 10.16; Found: C, 55.52; H, 5.63; N, 10.02.

firms presence of solvent. FAB MS: 554 (M⁺+1). Analysis for $C_{29}H_{33}F_2N_5O_4 \cdot 2HCl \cdot 0.7\ H_2O$: Calculated: C, 54.49; H, 5.74; N, 10.96. Found: C, 54.46; H, 5.73; N, 10.64.

EXAMPLE 51

(4S)-4-(3,4-Difluoro-phenyl)-3-{1-[4-(4-fluoro-2-hydroxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester Hydrochloride

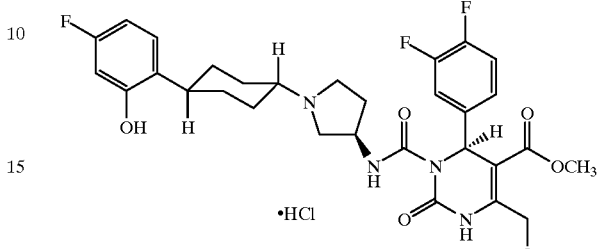

Analysis: Calcd. for $C_{31}H_{35}F_3N_4O_6 \cdot HCl \cdot 0.85\ H_2O \cdot 0.25\ C_4H_{10}O$; C, 55.95; H, 5.90; N, 8.16; Found: C, 56.17; H, 5.51; N, 7.81.

EXAMPLE 52

(4S)-4-(3,4-Difluoro-phenyl)-2-oxo-oxazolidine-3-carboxylic acid (1-[4-(4-fluoro-2-hydroxy-phenyl)-cyclohexyl]-(3R)-pyrrolidin-3-yl)-amide Hydrochloride

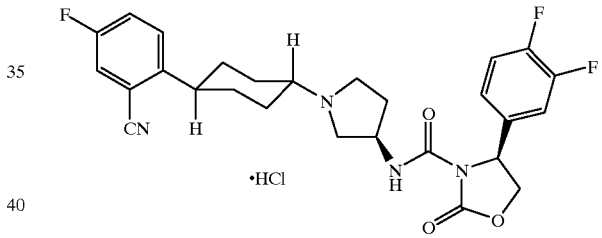

Analysis: Calcd. for $C_{26}H_{28}F_3N_3O_4 \cdot HCl \cdot 0.10\ H_2O$; C, 57.64; H, 5.43; N, 7.76; Found: C, 57.42; H, 5.22; N, 7.88.

EXAMPLE 53

(4S)-4-(3,4-Difluoro-phenyl)-2-oxo-oxazolidine-3-carboxylic acid {1-[4-(2-cyano-4-fluoro-phenyl)-cyclohexyl]-(3R)-pyrrolidin-3-yl}-amide

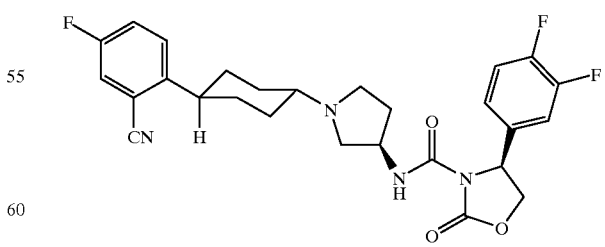

Analysis: Calcd. for $C_{27}H_{27}F_3N_4O_3 \cdot 0.35\ H_2O$; C, 62.50; H, 5.38; N, 10.80; Found: C, 62.87; H, 5.53; N, 10.42.

EXAMPLE 54

(4S)-4-(3,4-Difluoro-phenyl)-2-oxo-oxazolidine-3-carboxylic acid {1-[4-(2-cyano-4-fluoro-phenyl)-cyclohexyl]-(3R)-pyrrolidin-3-yl}-amide Hydrochloride

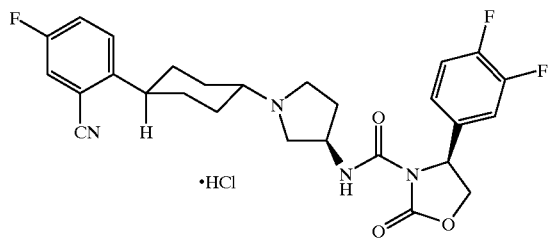

Analysis: Calcd. for $C_{27}H_{27}F_3N_4O_3$•HCl; C, 59.07; H, 5.14; N, 10.21; Found: C, 59.38; H, 5.42; N, 9.87.

EXAMPLE 55

(4S,5S)-4-(3,4-Difluoro-phenyl)-5-methyl-2-oxo-oxazolidine-3-carboxylic acid {1-[4-(2-cyano-4-fluoro-phenyl)-cyclohexyl]-(3R)-pyrrolidin-3-yl}-amide Hydrochloride

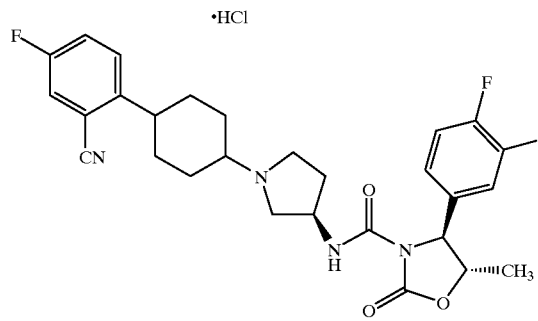

Analysis: Calcd. for $C_{28}H_{29}F_3N_4O_3$•HCl•1.25 $H_2O$; C, 57.43; H, 5.59; N, 9.57; Found: C, 57.19; H, 5.68; N, 9.79.

EXAMPLE 56

(4S,5S)-5-Cyclopropyl-4-(3,4-difluoro-phenyl)-2-oxo-oxazolidine-3-carboxylic acid (1-[4-(2-cyano-4-fluoro-phenyl)-cyclohexyl]-(3R)-pyrrolidin-3yl}-amide Hydrochloride

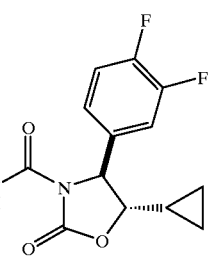

Analysis: Calcd. for $C_{30}H_{31}F_3N_4O_3$•HCl•0.55 $H_2O$; C, 60.15; H, 5.57; N, 9.35; Found: C, 59.85; H, 5.77; N, 9.14.

EXAMPLE 57

(4S)-4-(3,4-Difluoro-phenyl)-3-{1-[4-(2-fluoro-phenyl)-4-hydroxy-cyclohex-1-yl]-(3R)-pyrrolidin-3-ylcarbamoyl}-6-methyl-2-oxo-1,2,3,4-tetrahydro-pyrimidine-5-carboxylic acid methyl ester hydrochloride

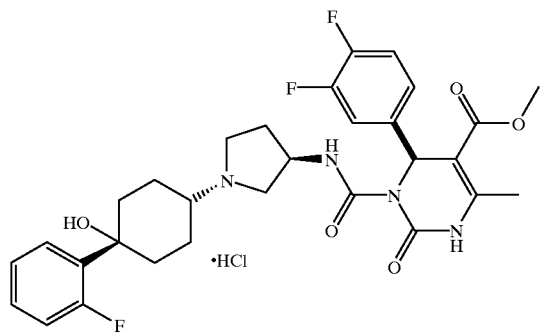

Analysis: Calcd. for $C_{30}H_{33}F_3N_4O_5$•HCl•0.60 $H_2O$•0.35 EtOAc; C,56.73; H,5.76; N, 8.43; Found: C, 56.73; H,5.83; N, 8.45.

EXAMPLE 58

(4S)-trans-4-(3,4-Difluoro-phenyl)-3-{1-[4-(2-fluoro-phenyl)-cyclohexyl]-(3R)-pyrrolidin-3-ylcarbamoyl}-6-methyl-2-oxo-1,2,3,4-tetrahydro-pyrimidine-5-carboxylic acid methyl ester hydrochloride

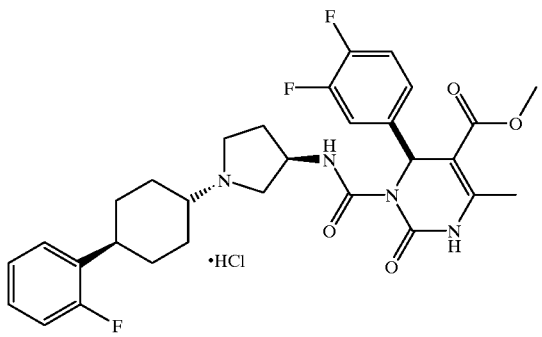

Analysis: Calcd. for $C_{30}H_{32}F_3N_4O_4 \cdot HCl \cdot 0.85\ H_2O \cdot 0.10$ EtOAc; C, 57.94; H, 5.68; N, 8.89; Found: C, 57.93; H, 5.91; N, 8.94.

EXAMPLE 59

(4S)-cis-4-(3,4-Difluoro-phenyl)-3-[1-(4-hydroxy-4-pyridin-2-yl-cyclohexyl)-(3R)-pyrrolidin-3-ylcarbamoyl]-2-oxo-1,2,3,4-tetrahydro-pyrimidine-5-carboxylic acid methyl ester hydrochloride

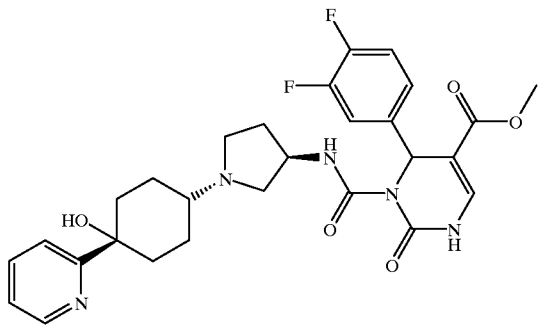

Analysis: Calcd. for $C_{28}H_{31}F_2N_5O_5 \cdot 2HCl \cdot 1.15\ H_2O$; C,51.80; H,5.4; N,10.79; Found: C, 51.79; H,5.60; N, 10.86.

EXAMPLE 60

(4S)-trans-4-(3,4-Difluorophenyl)-3-[1-(4-pyridin-2-yl-cyclohexyl)-(3R)-pyrrolidin-3-ylcarbamoyl]-2-oxo-1,2,3,4-tetrahydro-pyrimidine-5-carboxylic acid methyl ester

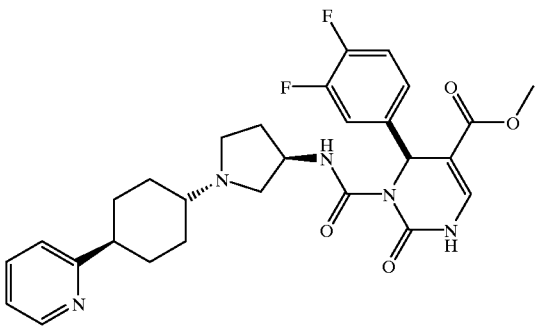

Analysis: Calcd. for $C_{28}H_{31}F_2N_5O_4 \cdot 0.75\ H_2O$; C,60.80; H,5.92; N,12.66; Found: C, 60.74; H,5.72; N,13.05.

EXAMPLE 61

(4S)-trans-3{1-[4-(2-Cyano-phenyl)-piperidin-1-yl]-(3R)-pyrrolidin-3-ylcarbamoly}-4-(3,4-difluoro-phenyl)-2-oxo-1,2,3,4-tetrahydro-pyrimidine-5-carboxylic acid methyl ester

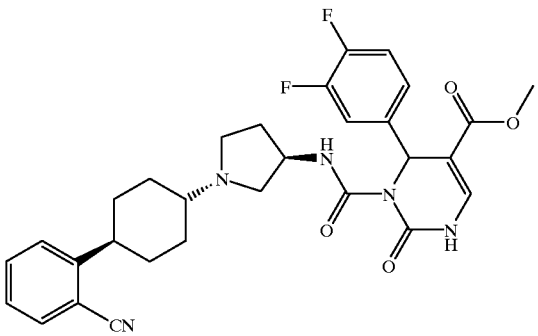

Analysis: Calcd. for $C_{30}H_{31}F_2N_5O_4 \cdot 0.75\ H_2O$; C, 62.43; H, 5.68; N, 12.14; Found: C, 62.43; H, 5.45; N, 12.27.

EXAMPLE 62

(4S,5S)-trans-5-Cyclopropyl-4-(3,4-difluorophenyl)-2-oxo-oxazolidine-3-carboxylic acid {1-[4-(4-fluorophenyl)-cyclohexyl]-(3R)-pyrrolidin-3-yl-amide

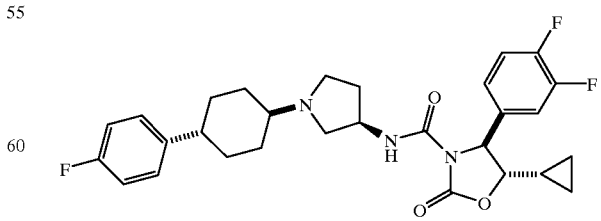

Calcd. for $C_{29}H_{32}N_3O_3F_3 \cdot 0.35\ H_2O \cdot 0.1\ CH_2Cl_2$; C, 64.44; H, 6.11; N, 7.75; Found C, 64.39; H, 5.97; N, 7.77.

EXAMPLE 63

(4S)-4-(3,4-Difluoro-phenyl)-3-[1-(4-hydroxy-4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester hydrochloride

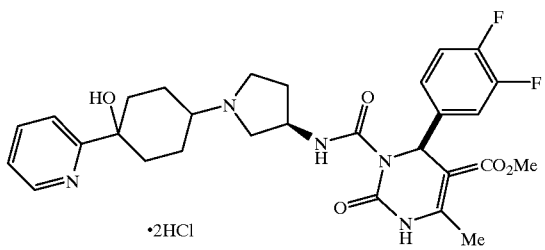

Analysis: Calcd. for $C_{29}H_{33}F_2N_5O_5 \cdot 2$ HCl; C, 50.26; H, 5.91; N,10.11; Found: C, 50.24; H, 5.72; N, 9.82.

EXAMPLE 64

(4S)-trans-4-(3,4-Difluorophenyl)-5-methyl-2-oxooxazolidine-3-carboxylic acid-[1-(4-pyridin-2-yl-cyclohexyl)-(3R)-pyrrolidin-3-yl]amide hydrochloride

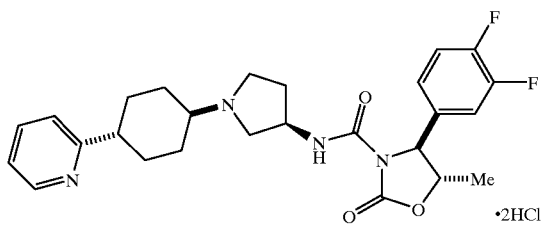

Mass Spectrum (FAB) Calcd. for $C_{26\ 27}F_2N_4O_3$; Found: 485 (M+1).

EXAMPLE 65 trans-4S-(3,4-Difluorophenyl)-6-methyl-2-oxo-3-{1-[4-(1-oxopyridin-2-yl)-cyclohexyl]-3R-pyrrolidin-3-ylcarbamoyl}-1,2,3,4-tetrahydropyrimidine-5-carboxylic acid methyl ester hydrochloride

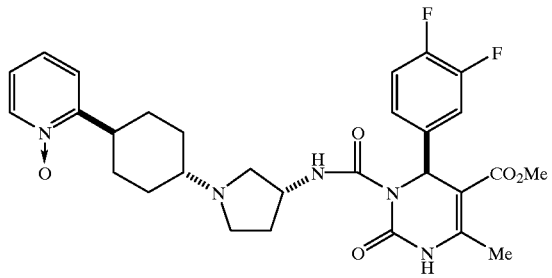

Step A: 2-(1,4-Dioxaspiro[4.5]dec-7-en-8-yl)pyridine
To a solution of trifluoromethanesulfonic acid 1,4-dioxaspiro[4.5]dec-7-en-8-yl ester (25.41 g, 88.15 mmol) in THF (266 mL) at room temperature was added palladium tetrakistripherlylphosphine (5.08 g, 4.4 mmol) under an inert atmosphere. To this mixture was added a solution of 2-pyridyl zinc bromide (264.4 mL of a 0.5 N solution in THF, 132.2 mmol) resulting in a slight exotherm. The resulting reaction mixture was then stirred 15 minutes. The reaction was quenched with the addition of 200 mL of saturated sodium bicarbonate solution. After stirring 5 minutes more, the phases were separated and the aqueous layer was extracted with ethyl acetate The combined organic extracts were washed with saturated sodium chloride, dried with sodium sulfate, and concentrated in vacuo. The crude material was chromatographed over silica gel eluting with 25% ethyl acetate/hexane to give 14.6 (76%) of homogeneous product.

Step B: 2-(1,4-Dioxaspiro[4.5]dec-8-yl)pyridine
To a solution of 14.6 g (67.19 mmol) of 2-(1,4-dioxaspiro[4.5]dec-7-en-8-yl)pyridine in ethyl acetate (400 mL) was added 4.6 g of 10% palladium on carbon catalyst. The resulting suspension was then hydrogenated at ambient temperature and atmospheric pressure until all the starting material was consumed (10.5 hr). The reaction mixture was filtered through celite and the filtrate was concentrated to give the product as an oily solid.

Step C: 2-(1,4-Dioxaspiro[4.5]dec-8-yl)pyridine N-oxide
To an ice cold solution of 3 g (13.68 mmol) of 2-(1,4-dioxaspiro[4.5]dec-8-yl)pyridine in chloroform (46 mL) was added 4.51 g (14.36 mmol) of meta-chloroperoxybenzoic acid (50–60%). The reaction mixture was stirred and allowed to come to room temperature over a four hour period. The volume of the reaction mixture was reduced by approximately 75% under reduced pressure and the residual material was partitioned between ethyl acetate and 1 N aqueous sodium hydroxide solution. The organic phase was separated and washed with water and brine, then dried (sodium sulfate) and concentrated to yield 3 g of the product as an oil.

Step D: 2-(4-Oxocyclohexyl)pyridine N-oxide
2-(1,4-Dioxaspiro[4.5]dec-8-yl)pyridine N-oxide (3 g, 12.75 mmol) was combined with glacial acetic acid (20 mL), concentrated hydrochloric acid (10 mL), and water (10 mL). The resulting mixture was heated to 45° C. for 24 hours. The reaction was cooled to 0° C. and the pH was adjusted to 6 with 20% sodium hydroxide solution. The phases were separated and the aqueous layer was extracted with ethyl acetate (3×100 mL). The combined organic extracts were washed with water and brine, then dried (sodium sulfate), and concentrated under reduced pressure to yield 1.8 g of the product as an oil.

Step E: 2-[trans-4-(3R-3-Aminopyrrolidin-1-yl)-cyclohexyl]pyridine N-oxide
To a solution of 17.8 mL of methanol containing 2-(4-oxocyclohexyl)pyridine N-oxide (1.8 g, 9.41 mmol) and 1.75 g (9.41 mmol) of (3R)-(+)-3-(tert-butoxycarbonylamino)-pyrrolidine was added 3.23 mL (56.4 mmol) of glacial acetic acid under an inert atmosphere. The resulting solution was stirred at ambient temperature for 20 minutes, cooled to 0° C., and treated with four equal portions of solid sodium cyanoborohyride (total: 296 mg, 4.71 mmol). The reaction mixture was stirred at 0° C. for 20 minutes more. All volatiles were removed under reduced pressure and the residue was taken up in 200 mL of ethyl acetate. The organic layer was washed with 10% sodium carbonate solution and brine, then dried (sodium sulfate) and concentrated to yield 2.86 g of the crude product as an oil. The desired trans-2-[4-(3-tert-butoxycarbonylaminopyrrolidin-1-yl)-cyclohexyl]-pyridine N-oxide was obtained via preparative centrifugal chromatography on silica gel (chloroform-methanol gradient elution). A portion of this material (544 mg, 1.505 mmol) was dissolved in 300 mL ethyl acetate at 0° C., and HCl gas was bubbled through the solution for 10 min. The reaction mixture was allowed to come to room temperature over a 1 hour period. All volatiles were rotoevaporated under reduced pressure to give a white solid. This material was resuspended in 200 mL of ethyl acetate and treated with 10 ml of 10% sodium carbonate solution. After 10 minutes the phases were separated and the organic layer was dried (sodium sulfate). The aqueous layer was concentrated to dryness and the residue was stirred with a chloroform-methanol mixture (4:1, v/v). The suspension was filtered and the filtrate was combined with the ethyl acetate extracts. The combined organic extracts were then concentrated and azeotropically dried with toluene to give 400 mg of the title compound as a tan powder.

Step F: trans-4S-(3,4-Difluorophenyl)-6-methyl-2-oxo-3-{1-[4-(1-oxopyridin-2-yl)-cyclohexyl]-3R-pyrrolidin-3-ylcarbamoyl}-1,2,3,4-tetrahydropyrimidine-5-carboxylic Acid Methyl Ester Hydrochloride 2-[trans-4-(3R-3-Aminopyrrolidin-1-yl)-cyclohexyl]pyridine N-oxide (300 mg, 1.148 mmol) and (+)-3-(4-nitrophenoxycirbonyl)-4S-(3,4-difluorophenyl)-6-methyl-2-oxo-1,2,3,4-tetrahydropyrimicline-5-carboxylic acid methyl ester (514 mg, 1.148 mmol) were combined in 20 mL of dry tetrahydrofuran at room temperature under nitrogen. The solution was stirred for 10 minutes, an additional 50 mg of (+)-3-(4-nitrophenoxycarbonyl)-4S-(3,4-difluorophenyl)-6-methyl-2-oxo-1,2,3,4-tetrahydropyrimidine-5-carboxylic acid methyl ester was added, and stirring was continued for 1 hour. The reaction mixture was concentrated in vacuo and the residue was purified directly via preparative centrifugal chromatography on silica gel (first ethyl acetate and then chloroform-methanol gradient elution: $CHCl_3$/MeOH, 100%/0% to 85%/15%) to give the title compound as the free base. The hydrochloride salt was prepared by dissolving the chromatographed product in ice cold ethyl acetate and treating this solution with a solution of ethyl acetate saturated with HCl gas. In this way, the title compound was obtained analytically pure as an off-white solid: m.p. 195–200° C.

Anal. Calcd. for $C_{29}H_{33}F_2N_5O_5 \cdot HCl \cdot 2.2\ H_2O$: C, 53.78; H, 5.60; N, 10.59. Found: C, 53.94; H, 5.60; N, 10.59%.

EXAMPLE 66 trans-2-(3,4-Difluorophenyl)-1-[1-(4-pyridin-2-yl-cyclohexyl)-3R-pyrrolidin-3-ylcarbamoyl]-6-methoxymethyl-2-oxo-1,2,3,4-tetrahydro-pyrimidine

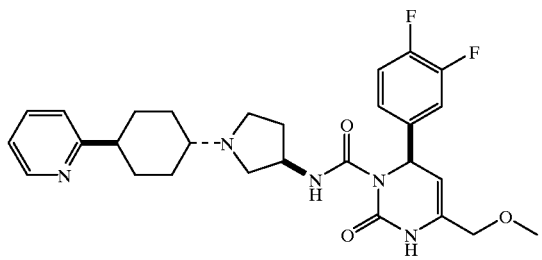

The title compound was prepared in accordance with the following scheme:

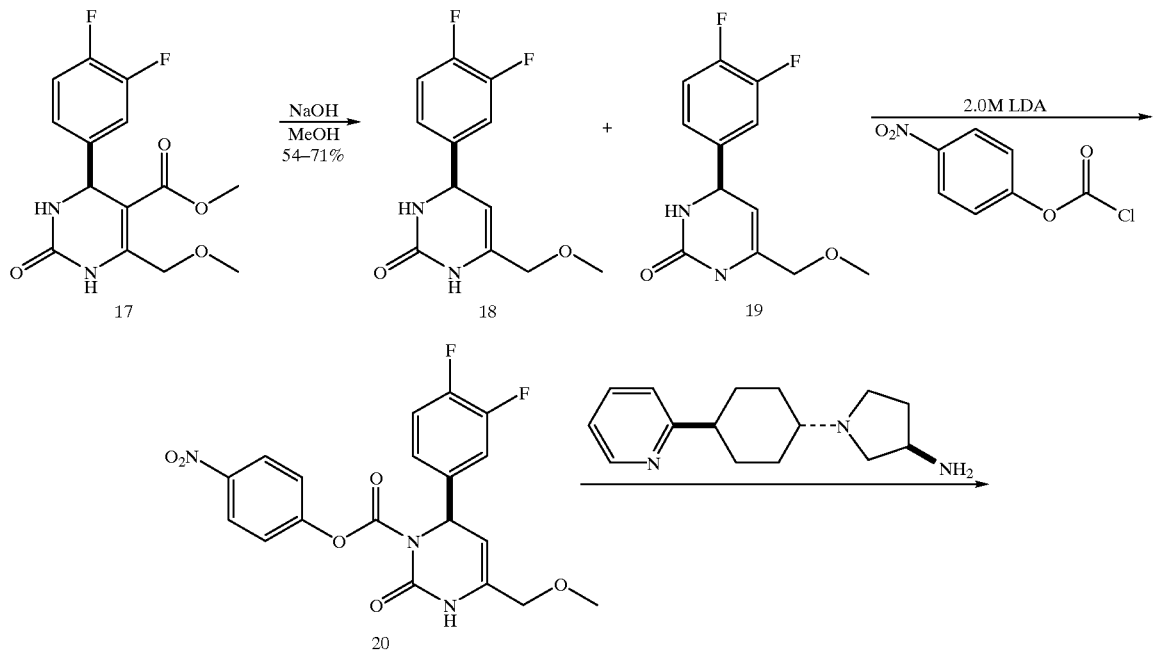

-continued

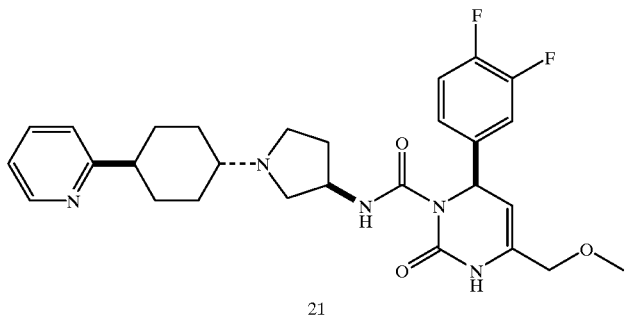

21

Step A: To a solution of (+)-DHP 17 (4.63 g, 14.7 mmol) in a methanol (100 ml) was added sodium hydroxide (2.94 g, 73.6 mmol). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $NaSO_4$, concentrated, and purified by PCTLC (7% MeOH in $CHCl_3$ with 2% $NH_4OH$) to afford a 2.65 g mixture of 18 and 19 (71% yield). The $^1H$ NMR was consistent with the assigned structure.

MS (FAB) 255 (M+1).

Step B (alternative to Step A): To a solution of (+)-DHP 17 (5.36 g, 17.0 mmol) in a methanol (150 ml) was added 1N NaOH (10 ml). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.35 g mixture of 18 and 19 (54% yield). The $^1H$ NMR is consistent with the assigned structure.

MS (FAB) 255 (M+1).

Step C: The title compound was prepared by reacting a mixture of 18 and 19 (1.93 g, 7.59 mmol) with 4-nitrophenoxycarbonyl chloride (1.5 equivalents) in LDA (1.1 equivalents) at −78° C. until the reaction was completed as determined by GLC. 0.488 g (15% yield) of 2 was obtained. The $^1H$ NMR was consistent with the assigned structure.

Step D: The title compound was obtained from 20 (0.119 g, 0.284 mmol) using the procedure described for step F in Example 1. The $^1H$ NMR was consistent with the assigned structure. $C_{28}H_{33}F_2N_5O_3$ MS (FAB) 526 (M+H).

EXAMPLE 67

(4S,5R)-trans-4-(3,4-Difluorophenyl-3-{1-[4-(4-fluoro-2-methoxycarbonylphenyl)-cyclohexyl]-(3R)-pyrrolidin-3-ylcarbamoyl}-2-oxo-oxazolidine-5-carboxylic acid methyl ester

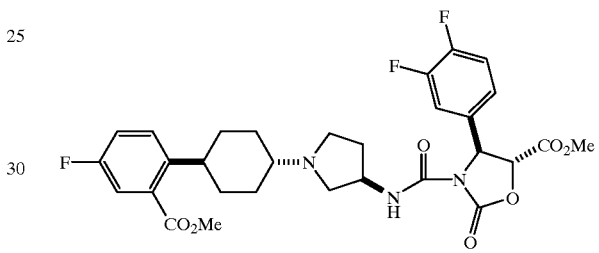

Step A: trans-3,4-Difluorocinnamic acid methyl ester

To a solution of trans-3,4-difluorocinnamic acid (10 g, 54 mmol) in 300 mL methanol was added concentrated sulfuric acid (2 mL). The solution was stirred 48 h at ambient temperature and then concentrated in vacuo. The residue was taken up in ethyl acetate (500 mL) and washed with saturated sodium bicarbonate (2×100 mL), brine (1×100 mL), dried with magnesium sulfate, and concentrated in vacuo to provide trans-3,4-difluorocinnamic acid methyl ester (10.7 g, 54 mmol, 100%) as a white solid.

$^1H$ NMR $d_H$ (400 MHz, $CDCl_3$) 7.59 (d, 1H, J=15.9), 7.34 (m, 1H), 7.24 (m, 1H) 7.18 (dd, 1H, J=9.9, 2.0), 6.35 (d, 1H, J=16.1), 3.81 (s, 3H).

Step B: (2R, 3S)-N-Benzyloxycarbonyl-3-amino-3-(3,4-difluorophenyl)-2-hydroxypropionic acid methyl ester A solution of NaOH (4.1 g, 103 mmol) was prepared in 175 mL water. Potassium osmate dihydrate (491 mg, 1.3 mmol) was dissolved in 35 mL of this NaOH solution, resulting in a dark pink homogeneous mixture. To a 1000 mL round bottom flask is added the remaining NaOH solution prepared above, 135 mL n-propanol and benzyl cabamate (9.8 g, 110 mmol). The suspension was stirred at ambient temperature for 30 min wherein the mixture was nearly homogeneous. The reaction flask was placed in a room temperature water bath and the surrounding lights were turned off. Freshly prepared t-butylhypochlorite (11.2 mL, 103 mmol) was added dropwise with vigorous stirring, and the reaction stirred an additional 15 min. In a separate 250 mL round bottom flask was suspended trans-3,4-difluorocinnamic acid methyl ester (6.6 g, 33.3 mmol) and (DHQ)$_2$PHAL (1.3 g, 1.7 mmol) in 100 mL n-propanol. The suspension was added to the above reaction mixture and the residue rinsed into the reaction flask (2×10 mL). To the reaction was added the above prepared solution of potassium osmate dihydrate. The resulting green solution became amber/brown over 1 h. Sodium metabisulfite (66 g, 347 mmol) was added and the resulting suspension stirred 3 h when it was poured into a separatory fimnel containing ethyl acetate (200 mL) and the layers separated. The aqueous layer was extracted with ethyl acetate (150 mL) and the combined organics washed with brine (100 mL), dried with magnesium sulfate, and concentrated in vacuo to provide a pale yellow solid. The crude material was passed through silica (25% ethyl acetate/hexane) to give (2R, 3S)-N-benzyloxycarbonyl-3-amino-3-(3,4-difluorophenyl)-2-hydroxypropionic acid methyl ester contaminated with benzyl carbamate.

Step C: (2R, 3S)-3-Amino-3-(3,4-difluorophenyl)-2-hydroxypropionic acid methyl ester (2R, 3S)-N-benzyloxycarbonyl-3-amino-3-(3,4-difluroophenyl)-2-hydroxypropionic acid methyl ester (>12.2 g, 33.3 mmol maximum) was dissolved in 750 mL ethanol. The flask was purged and filled with argon three times. Palladium on carbon (2 g, 10% wt) was added under argon and the suspension was again purged and filled with argon three times. The suspension was then purged, filled with hydrogen, and stirred 16 h. The suspension was purged, filled with argon three times, filtered through celite and concentrated in vacuo to give (2R, 3S)-3-amino-3-(3,4-difluorophenyl)-2-hydroxypropionic acid methyl ester (5.8 g, 25 mmol, 75% from trans-3,4-difluorocinnamic acid methyl ester).

$^1$H NMR d$_H$ (400 MHz, CDCl$_3$) 7.26 (m, 1H), 7.15–7.08 (m, 2H), 4.28 (s, 2H), 3.82 (s, 3H), 2.48 (bs, 2H).

Step D: (4S,5R)-4-(3,4-Difluorophenyl)-2-oxo-oxazolidine-5-carboxylic acid methyl ester To a solution of (2R, 3S)-3-amino-3-(3,4-difluorophenyl)-2-hydroxypropionic acid methyl ester (5.8 g, 25 mmol) in 250 mL tetrahydrofuran at 0° C. was added N,N-diisopropylethylamine (8.75 mL, 50 mmol) and triphosgene (2.48 g, 8.4 mmol). The reaction was stirred at 0° C. for 30 min when it was poured over ethyl acetate (200 mL) and saturated sodium carbonate solution (100 mL). The layers were separated, the organic layer washed with saturated sodium carbonate solution (1×100 mL), dried with magnesium sulfate, and concentrated in vacuo to provide a pale yellow oil. The material was triturated with 25% ethyl acetate/hexane from dichloromethane to provide (4S,5R)-4-(3,4-difluorophenyl)-2-oxo-oxazolidine-5-carboxylic acid methyl ester. The recovered mother liqour was passed through silica (50% ethyl acetate/hexane) to give an additional 1.1 g (4.8 g total, 18 mmol, 75%)

$^1$H NMR d$_H$ (400 MHz, CDCl$_3$) 7.25–7.20 (m, 2H), 7.15 (m, 1H), 6.33 (bs, 1H), 4.98 (d, 1H, J=5.1), 4.72 (d, 1H, J=5.3), 3.89 (s, 3H).

FABMS M+H=258.

Step E: (4S,5R)-4-(3-,4-difluorophenyl)-2-oxo-oxazolidine-3,5-dicarboxylic acid methyl ester 3-(4-nitropheryl) ester To a solution of (4S,5R)-4-(3,4-difluorophenyl)-2-oxo-oxazolidine-5-carboxylic acid methyl ester (910 mg, 3.5 mmol) in anhydrous tetrahydrofuran (50 mL), cooled to –78° C. under argon, was added a THF solution of lithium bis(trimethylsilyl)amide (3.5 mL, 3.5 mmol) dropwise. The reaction mixture was warmed to 0° C. in an ice bath, stirred 30 minutes, then returned to –78° C. In a separate flask, p-nitrophenylchloroformate (714 mg, 3.54 mmol) was dissolved in anhydrous tetrahydrofuran (40 mL) under argon and cooled to –78° C. The above prepared anion solution was added via cannula to the chloroformate solution and the reaction mixture was stirred 1 h at –78° C. The reaction mixture was treated with ethyl acetate (150 mL) and the resulting solution was washed with water (1×150 ml), brine (1×150 ml) and dried over magnesium sulfate and filtered. The volitiles were removed under reduced pressure and the resulting oil was triturated with diethyl ether. Ether was twice decanted from the resulting pale yellow solid to give (4S,SR)-4-(3-,4-difluorophenyl)-2-oxo-oxazolidine-3,5-dicarboxylic acid methyl ester 3-(4-nitrophenyl) ester (1.3 g, 3.1 mmol, 87%).

FAB MS: m/z=423 (M+H).

Step F: (4S,5R)-trans-4-(3,4-Difluorophenyl)-3-[1-[4-(4-fluoro-2-methoxycarbonylphenyl)-cyclohexyl]-(3R)-pyrrolidin-3-ylcarbamoyl}-2-oxo-oxazolidine-5-carboxylic acid methyl ester To a solution of trans-2-[4-(3-amino-(3R)-pyrrolidin-1-yl)cyclohexyl]-5-fluorobenzoic acid methyl ester (145 mg, 0.37 mmol) in dry, degassed N,N-dimethylformamide (3 mL) was added N,N-diisopropylethylamine (130 mL, 0.74 mmol) followed (4S,5R)-4-(3-,4-difluorophenyl)-2-oxo-oxazolidine-3,5-dicarboxylic acid methyl ester 3-(4-nitrophenyl) ester (156 mg, 0.37 mmol). The reaction mixture was stirred at ambient temperature for 4 h. The volitiles were removed under reduced pressure and residue dissolved in ethyl acetate, washed with 10% aqueous sodium carbonate solution (8×100 ml), brine (1×100 ml), dried over magnesium sulfate and filtered. The volatiles were removed under reduced pressure and the resulting oil was purified by pressurized silica gel chromatography (2–5% methanol in ethyl acetate) to afford (4S,5R)-trans-4-(3,4-difluorophenyl)-3-{1-[4-(4-fluoro-2-methoxycarbonylphenyl)-cyclohexyl]-(3R)-pyrrolidin-3-ylcarbamoyl}-2-oxo-oxazolidine-5-carboxylic acid methyl ester as a white foamy solid. The hydrochloride salt was prepared according to standard procedures and isolated as a white solid (125 mg, 0.2 mmol, 56%).

$^1$H NMR d$_H$ (400 MHz, CD$_3$OD) 7.46 (m, 2H), 7.33 (m, 2H), 7.24 (m, 2H), 5.54 (dd, J=3.85, 1.83 Hz, 1H), 5.03 (dd, J=3.84, 2.01 Hz, 1H), 3.89 (s, 3H), 3.87 (s,3H), 3.82–3.20 (m, 8H), 2.57 (m, 1H), 2.30 (m, 3H), 1.65 (m, 4H).

Analysis: Calcd for C30 H32 N3 O7 F3•HCl•0.15 Et2O•0.85 H2O, C 55.14, H 5.47, N 6.31. Found: C 55.13, H 5.44, N 6.16; HPLC retention time=9.082 min, purity= 96%; FAB MS: m/z=604 (M+H);

The compounds in Examples 68–73 were prepared by procedures substantially as described above for Example 67, Step F.

EXAMPLE 68

(4S,5R)-trans-4-(3,4-Difluorophenyl)-3-(1-{4-[4-fluoro-2-(2,2,2-trifluoroethoxy)phenyl]cyclohexyl}-(3R)-pyrrolidin-3-ylcarbamoyl)-2-oxo-oxazolidine-5-carboxylic acid methyl ester

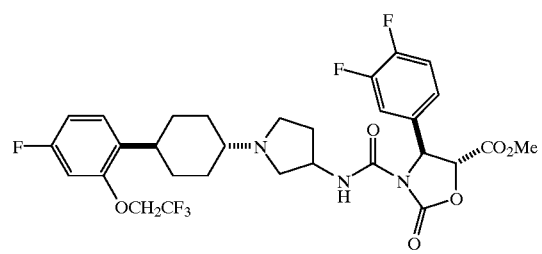

FAB MS: m/z=644 (M+H); Analysis: Calcd for C30H31N3O6F6•F3CCO2H, C 50.73, H 4.26, N 5.55. Found: C 50.34, H 4.13, N 5.50.

EXAMPLE 69

(4S,5R)-trans-4-(3,4-Difluorophenyl)-2-oxo-3-[1-(4-pyridin-2-ylcyclohexyl)-(3R)-pyrrolidin-3-ylcarbamoyl]-oxazolidine-5-carboxylic acid methyl ester

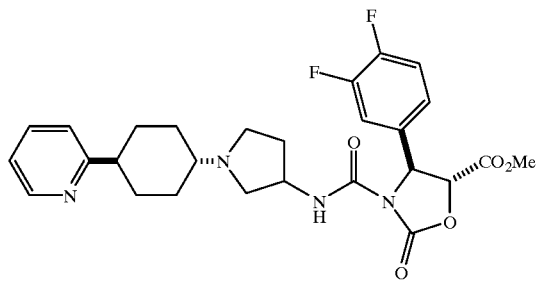

FAB MS: m/z=529 (M+H); Analysis: Calcd for C27H30N4O5F2•2 HCl•0.95 H2O•0.3 EtOAc; C 52.85, H 5.80, N 8.55; Found: C 52.86, H 5.45, N 8.55.

EXAMPLE 70

(4S,5R)-trans-4-(3,4-Difluorophenyl)-3-{1-[4-(4-fluoro-2-methoxyphenyl)cyclohexyl]-(3R)-pyrrolidin-3-ylcarbamoyl]-2-oxo-oxazolidine-5-carboxylic acid methyl ester

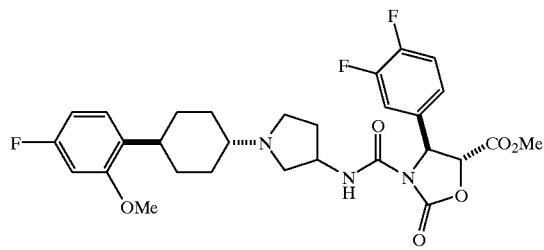

FAB MS: m/z=576 (M+H); Analysis: Calcd for C29H32N3O6F3•HCl•0.25 H2O; C 56.49, H 5.48, N 6.82. Found: C 56.52, H 5.50, N 7.03.

EXAMPLE 71

(4S,5R)-3-{1-[4-Cyano-4-(2-methoxyphenyl)cyclohexyl]-(3R)-pyrrolidin-3-ylcarbamoyl}-4-(3,4-difluorophenyl)-2-oxo-oxazolidine-5-carboxylic acid methyl ester

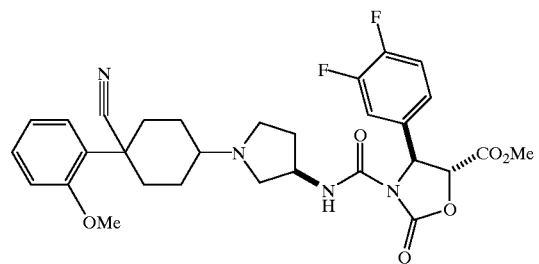

FAB MS: m/z=583 (M+H); Analysis: Calcd for C30H32N4O6F2•F3CCO2 H•0.6 CH2 Cl2; C 52.37, H 4.61, N 7.49. Found: C 52.32, H 4.37, N 7.24.

EXAMPLE 72

(4S,5R)-3-{1-[4-Cyano-4-(2-fluorophenyl)cyclohexyl]-(3R)-pyrrolidin-3-ylcarbamoyl}-4-(3,4-difluorophenyl)-2-oxo-oxazolidine-5-carboxylic acid methyl ester

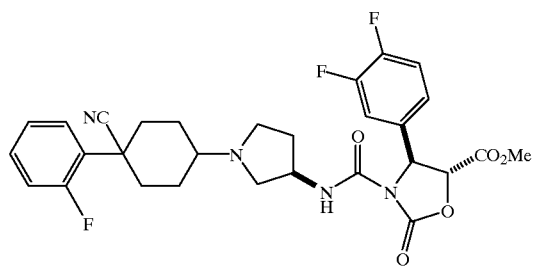

FAB MS: m/z=571 (M+H); Analysis: Calcd for C29H29N4O5F3•HCl•0.65 H2O; C 56.30, H 5.10, N 9.06. Found: C 56.33, H 5.22, N 8.83.

EXAMPLE 73

(4S,5R)-trans-3-{1-[4-(2-Cyanophenyl)cyclohexyl]-(3R)-pyrrolidin-3-ylcarbamoyl}-4-(3,4-difluorophenyl)-2-oxo-oxazolidine-5-carboxylic acid methyl ester

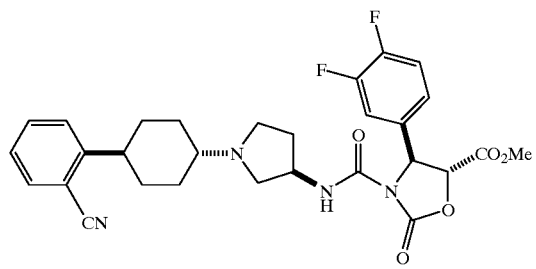

FAB MS: m/z=553 (M+H); Analysis: Calcd for C29H30N4O5F2•HCl•0.5 H2O; C 58.24, H 5.39, N 9.37. Found: C 58.23, H 5.42, N 9.07.

EXAMPLE 74

(4S,5R)-trans-4-(3,4-difluorophenyl)-5-hydroxymethyl-2-oxo-oxazolidine-3-carboxylic acid (1-[4-(4-fluorophenyl)cyclohexyl]-(3R)-pyrrolidin-3-yl} amide

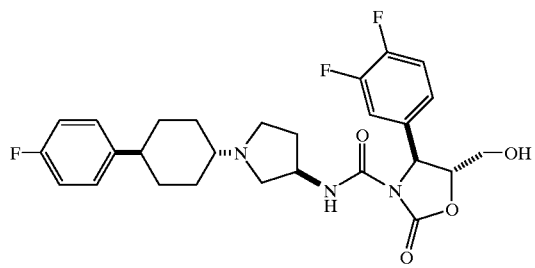

Step A: (4S,5R) 4-(3,4-Difluorophenyl)-5-hydroxymethyl-oxazolidin-2-one

To a solution of (4S,5R)-4-(3,4-difluorophenyl)-2-oxo-oxazolidine-5-carboxylic acid methyl ester [(200 mg, 0.8 mmol) product of Example 67, Step D] in tetrahydrofuran (10 mL) at 0° C. was added a 2 M solution of lithium borohydride in tetrahydrofuran (0.4 mL, 0.8 mmol). After stirring for 20 min at 0° C., saturated sodium bicarbonate (20 mL) was added and the mixture stirred at ambient temperature fcr 20 min. Ethyl acetate (50 mL) was added and the layers separated. The organic layer was washed with brine (1×10 mL), dried with magnesium sulfate, filtered and concentrated in vacuo to provide (4S,5R) 4-(3,4-difluorophenyl)-5-hydroxymethyl-oxazolidin-2-one as a white solid (180 mg, 0.8 mmol, 100%).

$^1$H NMR d$_H$ (400 MHz, CDCl$_3$) 7.23–7.15 (m, 2H), 7.10–7.07 (m, 1H), 6.48 (bs, 1H), 4.89 (d, 1H, J=6.8), 4.31 (dt, 1H, J=6.6, 2.9), 3.96 (dd, 1H, J=12.82, 2.75), 3.70 (bdd, 1H, J=12.1, 2.2), 3.53 (bs, 1H).

Step B: (4S,5R) 4-(3,4-Difluorophenyl)-5-(tetrahydropyran-2-yloxymethyl)-oxazolidin-2-one To a solution of (4S,5R) 4-(3,4-difluorophenyl)-5-hydroxymethyl-oxazolidin-2-one (695 mg, 3.0 mmol) in dry dichloromethane (30 mL) was added 2,3-dihydropyran (0.3 mL, 3.6 mmol) and cam phorsulfonic acid (70 mg, 0.3 mmol). The reaction mixture was stirred at ambient temperature for 3 h. The reaction mixture was diluted with dichloromethane (100 mL) and washed with saturated sodium bicarbonate solution (2×100 ml), brine (1×100 ml), dried over magnesium sulfate and filtered. The volatiles were removed under reduced pressure and the resulting solid was purified by pressurized silica gel chromatography (1:1 then 2:1 ethyl acetate:hexane) to afford (4S,5R)-4-(3,4-difluorophenyl)-5-(tetrahydropyran-2-yloxymethyl)-oxazolidin-2-one as a colorless oil (750 mg, 2.4 mmol, 80%).

FAB MS: m/z=314 (M+H$^+$)

Step C: (4S,5R)-4-(3,4-Difluorophenyl)-2-oxo-5-(tetrahydropyran-2-yloxymethyl)-oxazolidine-3-carboxylic acid 4-nitrophenyl ester To a solution of (4S,5R)-4-(3,4-difluorophenyl)-5-(tetrahydropyran-2-yloxymethyl)-oxazolidin-2-one (910 mg, 2.9 mmol) in anhydrous tetrahydrofuran (60 mL) cooled to −78° C. under argon, was added a THF solution of lithium bis(trimethylsilyl)amide (2.9 mL, 2.9 mmol) dropwise. The reaction mixture was warmed to 0° C. in an ice bath and stirred 45 min, and then returned to −78° C. Meanwhile, in a separate dried flask, the p-nitrophenylchloroformate (586 mg, 2.9 mmol) was dissolved in anhydrous tetrahydrofuran (50 mL) under argon and cooled to −78° C. Then the above prepared anion solution was added via cannula to the chloroformate solution and reaction mixture was stirred 1 h at −78° C. The reaction mixture was treated with ethyl acetate (150 mL). The resulting solution was washed with water (1×150 ml), brine (1×150 mL), dried over magnesium sulfate and filtered. The volatiles were removed under reduced pressure to give (4S,5R)-4-(3,4-diftuorophenyl)-2-oxo-5-(tetrahydropyran-2-yloxymethyl)-oxazolidine-3-carboxylic acid 4-nitrophenyl ester as a yellow foam (1.3 g, 2.8 mmol, 96%).

FAB MS: m/z=479 (M+H$^+$).

Step D: (4S,5R)-trans-4-(3,4-Difluorophenyl)-5-(tetrahydropyran-2-yloxymethyl-2-oxo-oxazolidine-3-carboxylic acid {1-[4-(4-fluorophenyl)cyclohexyl]-(3R)-pyrrolidin-3-yl} amide To a solution of trans-1-[4-(4-fluorophenyl)cyclohexyl]-(3R)-pyrrolidin-3-ylamine dihydrochloride (210 mg, 0.63 mmol) in dry tetrahydrofuran (4 mL) was added N,N-diisopropylethylamine (219 μL, 1.26 mmol) followed by (4S,5R)-4-(3,4-difluorophenyl)-2-oxo-5-(tetrahydropyran-2-yloxymethyl)-oxazolidine-3-carboxylic acid 4-nitrophenyl ester (300 mg, 0.63 mmol). The reaction mixture was stirred at ambient temperature for 18 h when the volatiles were removed under reduced pressure and residue dissolved in ethyl acetate (100 mL) and washed with 10% aqueous sodium carbonate solution (8×100 ml), brine (1×100 ml), dried over magnesium sulfate and filtered. The volatiles were removed under reduced pressure and the resulting oil was purified by pressurized silica gel chromatography (3:1 then 1:0 ethyl acetate:hexane to afford (4S, 5R)-trans-4-(3,4-difluorophenyl)-5-(tetrahydropyran-2-yloxymethyl-2-oxo-oxazolidine-3-carboxylic acid (1-[4-(4-fluorophenyl)cyclohexyl]-(3R)-pyrrolidin-3-yl} amide as a white foam (153 mg, 0.25 mmol, 40%).

Step E: (4S,5R)-trans-4-(3,4-Difluorophenyl)-5-hydroxymethyl-2-oxo-oxazolidine-3-carboxylic acid {1-[4-(4-fluorophenyl)cyclohexyl]-(3R)-pyrrolidin-3-yl} amide To a solution of (4S,5R)-trans-4-(3,4-difluorophenyl)-5-(tetrahydropyran-2-yloxymethyl)-2-oxo-oxazolidine-3-carb)xylic acid {1-[4-(4-fluorophenyl)cyclohexyl]-(3R)-pyrrolidin-3-yl} amide (153 mg, 0.26 mmol) was dissolved in methanol (5 mL) and p-toluenesulfonic acid (50 mg, 0.26 mmol) was added. The reaction mixture was stirred at ambient temperature for 17 h. The volatiles were removed under reduced pressure and the residue was taken up in ethlyl acetate (100 mL) and washed with saturated sodium carbonate solution (3×100 ml), brine (1×100 ml), dried over magnesium sulfate and filtered. The volatiles were removed under reduced pressure to afford an oil which was lyophilized at reduced pressure from acetonitrile and HCl (1N aqueous solution) to afford (4S,5R)-trans-4-(3,4-difluorophenyl)-5-hydroxymetliyl-2-oxo-oxazolidine-3-carboxylic acid {1-[4-(4-fluorophenyl)cyclohexyl]-(3R)-pyrrolidin-3-yl} amide.

HPLC: retention time=8.05 min, purity=94%; FAB MS: m/z=571 (M+H); Analysis: Calcd for C27 H30 N3 O4 F3•HCl•0.9 H$_2$O; C 56.87, H 5.80, N 7.37. Found: C 56.68, H 5.40, N 7.66.

The compound of Example 75 was prepared by procedures substantially as described above for Example 74, Steps E and F.

EXAMPLE 75

(4S,5R)-trans-4-(3,4-Difluorophenyl)-5-hydroxymethyl-2-oxo-oxazolidine-3-carboxylic acid {1-[4-(4-fluoro-2-methoxyphenyl)cyclohexyl]-(3R)-pyrrolidin-3-yl} amide

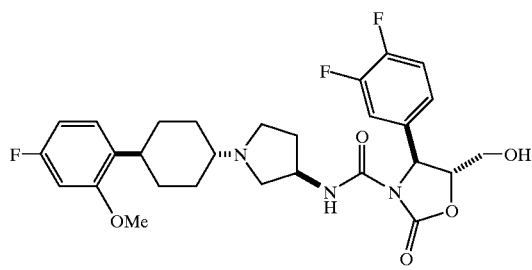

FAB MS: m/z=548 (M+H); Analysis: Calcd for C28H32N3O5F3•HCl•0.7 H2O; C 56.36, H 5.81, N 7.04. Found: C 56.35, H 5.82, N 6.76.

EXAMPLE 76

(4S,5R)-trans-4-(3,4-Difluorophenyl)-3-{1-[4-(4-fluoro-2-methoxyphenyl)cyclohexyl]-(3R)-pyrrolidin-3-ylcarbamoyl]-2-oxo-oxazolidine-5-carboxamide

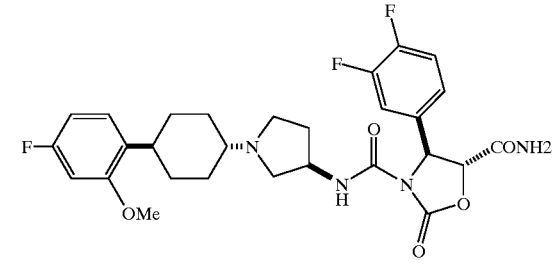

The title compound was prepared by the procedure described in Example 67, followed by pressurized silica gel chromatography using an elution system containing chloroform saturated with ammonia gas and methanol.

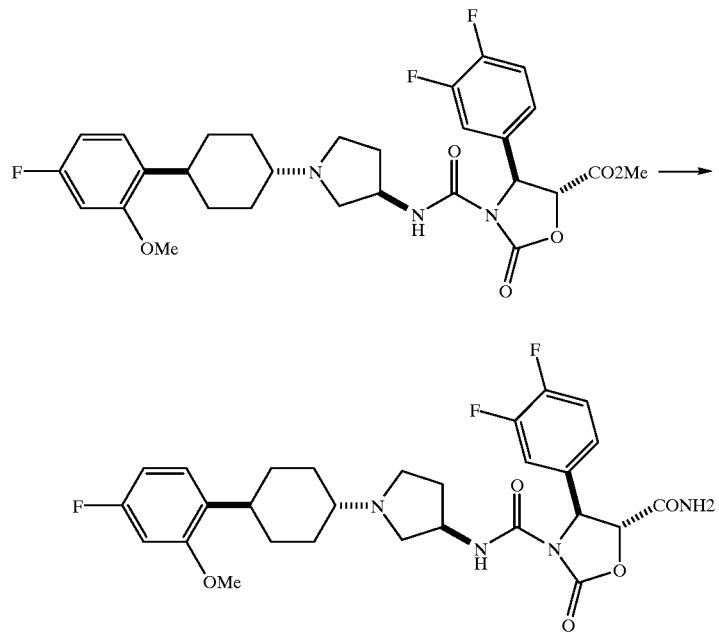

FAB MS: m/z=561 (M+H); Analysis: Calcd for C28H31N4O5F3; C 59.99, H 5.57, N 9.99. Found: C 59.84, H 5.47, N 9.85.

The compounds of Examples 77–79 were prepared using procedures substantially as described above for Example 76.

EXAMPLE 77

(4S,5R)-trans-4-(3,4-Difluorophenyl)-3-{1-[4-(4-fluorophenyl)cyclohexyl]-(3R)-pyrrolidin-3-ylcarbamoyl]-2-oxo-oxazolidine-5-carboxamide

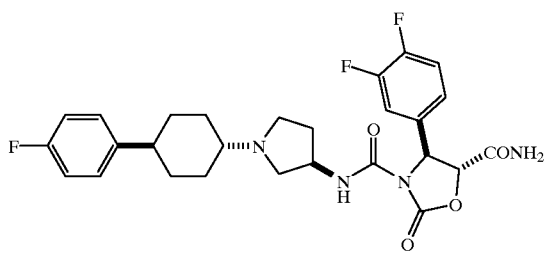

FAB MS: m/z=531 (M+H); Analysis: Calcd for C27H29N4O4F3•0.05 H2O; C 61.02, H 5.52, N 10.54. Found: C 61.07, H 5.47, N 10.51.

EXAMPLE 78

(4S,5R)-trans-4-(3,4-Difluorophenyl)-3-{1-[4-(2-fluorophenyl)cyclohexyl]-(3R)-pyrrolidin-3-ylcarbamoyl]-2-oxo-oxazolidine-5-carboxamide

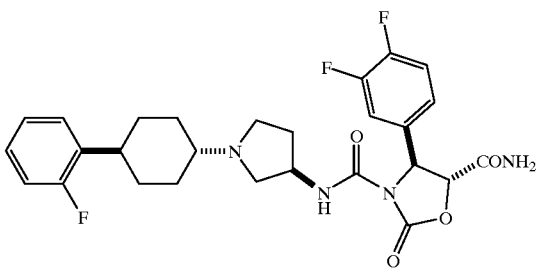

Analysis: Calcd for C27H29N4O4F3; C 61.12, H 5.51, N 10.56. Found: C 61.20, H 5.67, N 10.46.

EXAMPLE 79

(4S,5R)-trans-3-{1-[4-(2-Cyano-4-fluorophenyl)cyclohexyl]-(3R)-pyrrolidin-3-ylcarbamoyl}-4-(3,4-Difluorophenyl)-2-oxo-oxazolidine-5-carboxamide

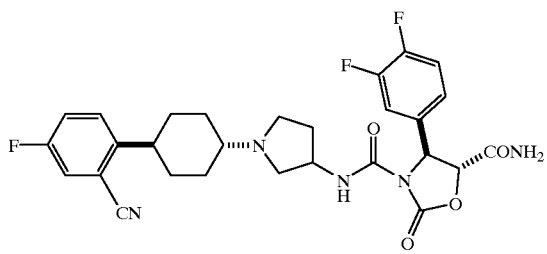

FAB MS: m/z=556 (M+H); Analysis: Calcd for C28H28N5O4F3•HCl•0.85 H2O•0.35 EtOAc; C 55.33, H 5.29, N 10.98. Found: C 55.33, H 4.90, N 10.65.

EXAMPLE 80

Mixture of 4S-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

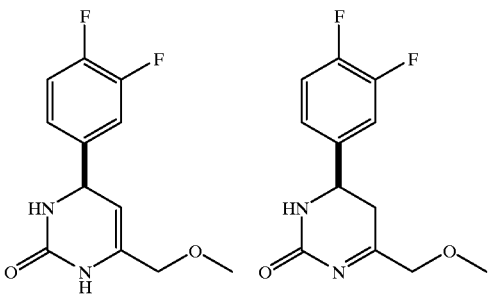

To a solution of (+)-4-(3,4-difluorophenyl)-6-methoxymethyl-2-oxo-1,2,3,4-tetrahydropyrimidine-5-carboxylic acid methyl ester (4.63 g, 14.7 mmol) in a methanol (100 ml) was added sodium hydroxide (2.94 g, 73.6 mmol). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.65 g mixture of the title compounds (71% yield). The $^1H$ NMR was consistent with the assigned structure.

MS (FAB) 255 (M+1);

EXAMPLE 81

Mixture of 4S-4-(3,4-difluorophenyl)-6-methoxymethyl-2-oxo-1,2,3,4-tetrahydropyrimidine and 4S-4-(3,4-difluorophenyl)-6-methoxymethyl-2-oxo-2,3,4,5-tetrahydropyrimidine

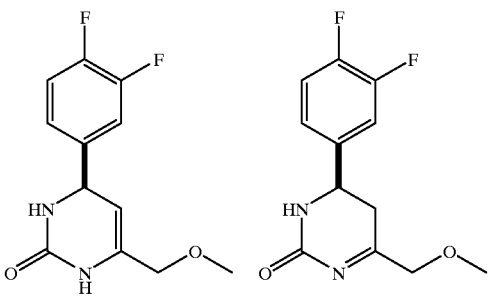

To a solution of (+)-4-(3,4-difluorophenyl)-6-methoxymethyl-2-oxo-1,2,3,4-tetrahydropyrimidine-5-carboxylic acid methyl ester (5.36 g, 17.0 mmol) in a methanol (150 ml) was added 1N NaOH (110 ml). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.35 g mixture of the title compounds (54% yield). The $^1H$ NMR was consistent with the assigned structure.

EXAMPLE 82

4S-4-(3,4-Difluorophenyl)-6-methoxymethyl-3-(4-nitrophenoxycarbonyl)-2-oxo-1,2,3,4-tetrahydropyrimidine-5-carboxylic acid methyl ester

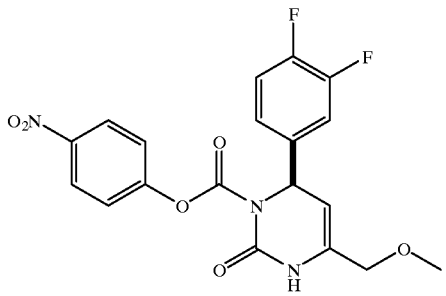

The title compound was prepared by treating the mixture obtained from Example 80 or Example 81 (1.93 g, 7.59 mmol) with lithium diisopropylamide (2.0M THF solution, 1.1 equivalents) in THF at −78° C. for 20 minutes followed by the rapid addition of 4-nitrophenyl chloroformate (1.5 equivalents) in THF. 0.488 g of the title compound was obtained in a 15% yield. The $^1$H NMR was consistent with the assigned structure.

EXAMPLE 83

Mixture of 4R-4-(3,4-difluorophenyl)-6-methoxymethyl-2-oxo-1,2,3,4-tetrahydropyrimidine and 4R-4-(3,4-difluorophenyl)-6-methoxymethyl-2-oxo-2,3,4,5-tetrahydropyrimidine

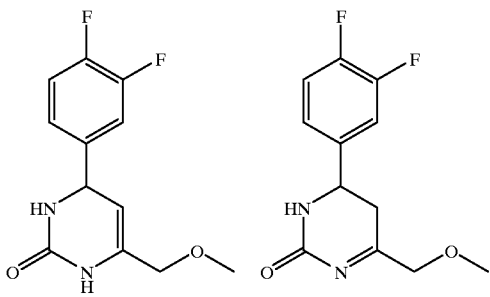

The title compounds were prepared from 4R-4-(3,4-difluorophenyl)-6-methoxymethyl-2-oxo-1,2,3,4-tetrahydropyrimidine-5-carboxylic acid methyl ester (5.0 g, 17.7 mmol) using the procedure described in Example 80. A mixture of 2.0 g of the title compounds was obtained in 50% yield. The $^1$H NMR was consistent with the assigned structure.

MS (FAB) 255 (M+1).

Compounds of the invention can be prepared by reacting the products obtained in Example 82 with an aminopiperidiiie, e.g., in accordance with Scheme 3. Compounds of the invention can also be prepared by preparing a nitrophenoxy derivative of the compound of Example 83 in accordance with the procedure set forth in Example 82 and then reacting the derivative with an aminopiperidine in accordance with Scheme 3.

The following compounds were prepared in accordance with procedures set forth in the preceding Examples and Schemes.

EXAMPLE 84 trans-(4S)-3-{1-[4-(2-Methoxyphenyl)cyclohexyl]azetidin-3-ylmethylcarbamoyl}-4-(3,4-difluorophenyl)-6-methoxymethyl-2-oxo-1,2,3,4-tetrahydropyrimidine-5-carboxylic acid methyl ester hydrochloride

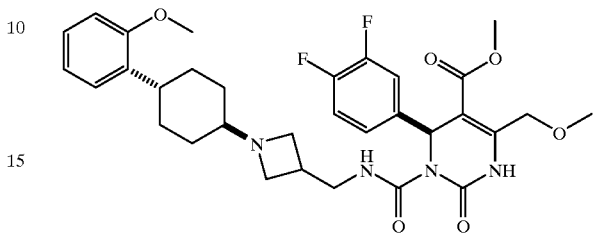

$^1$H NMR (CDCl$_3$, 400 MHz) consistent with assigned structure.

FABLRMS m/e 613.4 glmole (M$^+$+H, $C_{32}H_{38}F_2N_4O_6$= 612.67 g/mole.)

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 97% pure.

Anal. Calcd for $C_{32}H_{38}F_2N_4O_6$·1.0 HCl, 0.3 CHCl$_3$ and 0.35 H$_2$O: C=57.45, H=5.97, N=8.30. Found: C=57.48, H=5.97, N=8.40.

EXAMPLE 85 trans-(4S)-4-(3,4-Difluorophenyl)-2-oxo-oxazolidine-3-carboxylic acids {1-[4-(2-methoxyphenyl)-cyclohexyl]azetidin-3-ylmethyl-amid hydrochloride

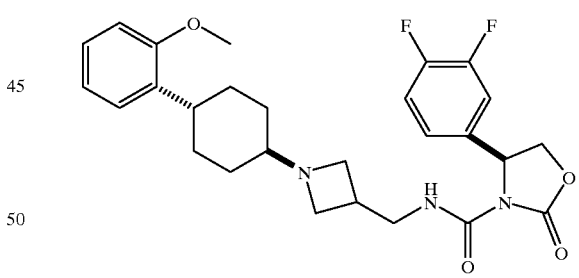

$^1$H NMR (CDCl$_3$, 400 MHz) consistent with assigned structure.

FABLRMS m/e 500.3 g/mole (M$^+$+H, $C_{27}H_{31}F_2N_3P_4$= 499.45 g/mole.).

HPLC (Vydac; C18; diameter=4.6 mm; length=150 mm; gradient=H$_2$O [0.1% H$_3$PO$_4$]—CH$_3$CN, 95%-5%, 5%95%, over 16 minutes, 2 ml/min flow rate) focus=215 nm; 99% pure.

Anal. Calcd for $C_{27}H_{31}F_2N_3$4·1.35 HCl and 1.1 Et$_2$O: C=59.83, H=6.93, N=9.56. Found: C=60.17, H=6.57, N=6.28.

EXAMPLE 86 trans-(4S)-3-{1-[4-(2-Cyanophenyl)cyclohexyl]azetidin-3-ylmethylcarbamoyl}-4-(3,4-difluorophenyl)-6-methoxymethyl-2-oxo-1,2,3,4-tetrahydropyrimidine-5-carboxylic acid methyl ester hydrochloride

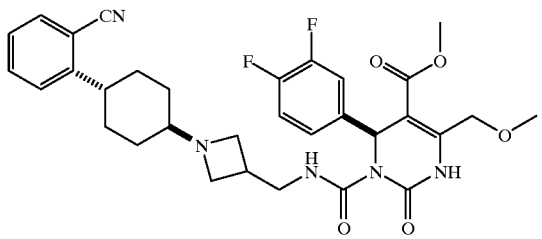

$^1$H NMR (CDCl$_3$, 400 MHz) consistent with assigned structure.

FABLRMS m/e 608 g/mole (M$^+$+H, C$_{32}$H$_{35}$F$_2$N$_5$O$_5$= 607.65 g/mole.)

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 97% pure.

Anal. Calcd for C$_{32}$H$_{35}$F$_2$N$_5$O$_5$•1.0 HCl and 0.8 H$_2$O: C=58.36, H=5.76, N=10.64. Found: C=58.40, H=5.80, N=10.42.

EXAMPLE 87 trans-(4S)-4-(3,4-Difluorophenyl)-2-oxo-oxazolidine-3-carboxylic acid {1-[4-(2-cyanophenyl)-cyclohexyl]azetidin-3-ylmethyl-amide hydrochloride

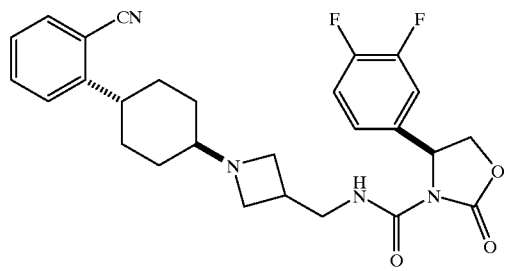

$^1$H NMR (CDCl$_3$, 400 MHz) consistent with issigned structure.

FABLRMS m/e 495 g/mole (M$^+$+H, C$_{27}$H$_{28}$F$_2$N$_4$O$_3$= 494.54 g/mole.)

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; >97% pure.

Anal. Calcd for C$_{27}$H$_{28}$F$_2$N$_4$O$_3$•1.0 HCl and 0.85 H$_2$O: C=59.36, H=5.66, N=10.26. Found: C=59.48, H=5.84, N=9.87.

EXAMPLE 88

(High Rf) (4S)-3-{1-[4-(2-pyridyl)cyclohexyl]azetidin-3-lmethylcarbamoyl}-4-(3,4-difluorophenyl)-6-methoxymethyl-2-oxo-1,2,3,4-tetrahydropyrimidine-5-carboxylic acid methyl ester hydrochloride

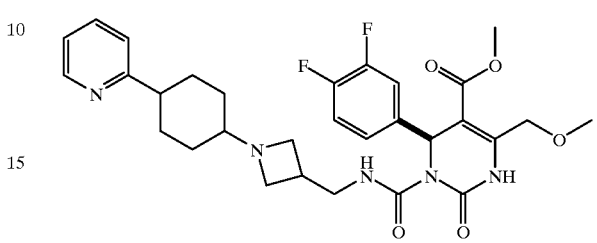

$^1$H NMR (CDCl$_3$, 400 MHz) consistent with assigned structure.

FABLRMS m/e 584 g/mole (M$^+$+H, C$_{30}$H$_{35}$F$_2$N$_5$O$_5$= 583.63 g/mole.)

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 99% pure.

Anal. Calcd for C$_{30}$H$_{35}$F$_2$N$_5$O$_5$•2.0 HCl, 0.5 CHCl$_3$ and 0.75 Et2O: C=52.19, H=5.75, N=9.09. Found: C=52.21, H=5.88, N=9.12.

EXAMPLE 90

(High Rf) (4S)-4-(3,4-Difluorophenyl)-2-oxo-oxazolidine-3-carboxylic acid {1-[4-(2-pyridyl)-cyclohexyl]azetidin-3-ylmethyl-amide hydrochloride

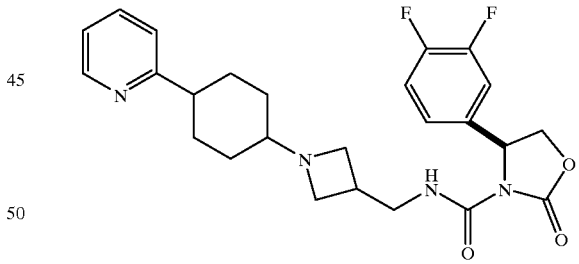

$^1$H NMR (CDCl$_3$, 400 MHz) consistent with assigned structure.

FABLRMS ni/e 471 g/mole (M++H, C$_{25}$H$_{28}$F$_2$N$_4$O$_3$= 470.51 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 99% pure.

Anal. Calcd for C$_{25}$H$_{28}$F$_2$N$_4$O$_3$•2.0 HCl, 0.4 CHCl$_3$ and 0.45 Et$_2$O: C=52.31, H=5.63, N=8.97. Found: C=52.33, H=5.60, N=9.15.

EXAMPLE 91

(Low Rf) (4S)-3-{1-[4-(2-pyridyl)cyclohexyl]
azetidin-3-ylmethylcarbamoyl}-4-(3,4-
difluorophenyl)-6-methoxymethyl-2-oxo-1,2,3,4-
tetrahydropyrimidine-5-carboxylic acid methyl ester
hydrochloride

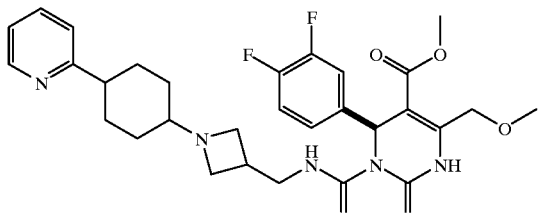

$^1$H NMR (CDCl$_3$, 400 MHz) consistent with assigned structure.

FABLRMS m/e 584 g/mole (M$^+$+H, C$_{30}$H$_{35}$F$_2$N$_5$O$_5$=583.63 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 99% pure.

Anal. Calcd for C$_{30}$H$_{35}$F$_2$N$_5$O$_5$•2.0 HCl and 2.35 Et$_2$O: C=51.63, H=5.88, N=10.04. Found: C=51.63, H=5.83, N=10.20.

EXAMPLE 92

(Low Rf) (4S)-4-(3,4-Difluorophenyl)-2-oxo-
oxazolidine-3-carboxylic acid {1-[4-(2-pyridyl)-
cyclohexyl]azetidin-3-ylmethyl-amide hydrochloride

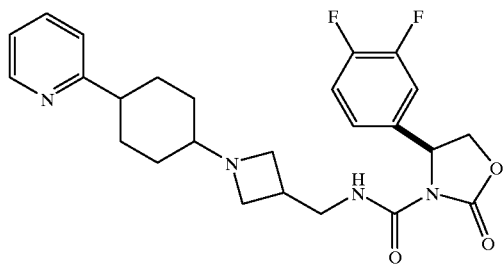

$^1$H NMR (CDCl$_3$, 400 MHz) consistent with assigned structure.

FABLRMS m/e 471 g/mole (M$^+$+H, C$_{25}$ $_{28}$F$_2$N$_4$O$_3$=470.51 g/mole.).

HPLC (Vydac; C18; diameter=4.6 mm; length=150 mm; gradient=H$_2$O [0.1% H$_3$PO4]—CH$_3$CN, 95%-5%, 5%-95%, over 16 minutes, 2 ml/min flow rate) focus=215 mm; 99% pure.

Anal. Calcd for C$_{25}$ $_{28}$F$_2$N$_4$O$_3$•2.0 HCl, 0. 15 CHCl$_3$ and 1.5 H$_2$O: C=51.34, H=5.68, N=9.52. Found: C=51.34, H=5.63, N=9.64.

EXAMPLE 93 trans-(4S)-3-{1-[4-(2-Cyanophenyl)cyclohexyl]
azetidin-3-ylcarbamoyl}-4-(3,4-difluorophenyl)-6-
methoxymethyl-2-oxo-1,2,3,4-tetrahydropyrimidine-
5-carboxylic acid methyl ester

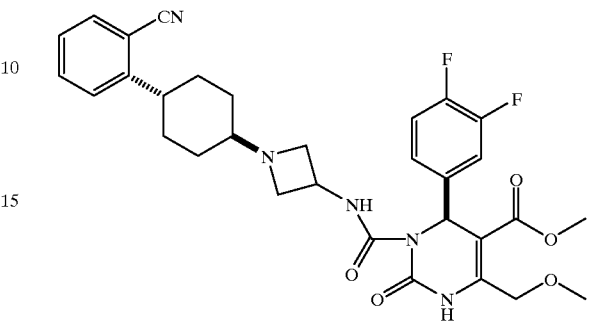

$^1$H NMR (CDCl$_3$, 400 MHz) consistent with assigned structure.

FABLRMS m/e 594 g/mole (M$^+$+H, C$_{31}$H$_{33}$F$_2$N$_5$O$_5$=593.63 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 mmin flow rate) focus=215 nm; 100% pure.

Anal. Calcd for C$_{31}$H$_{33}$F$_2$N$_5$O$_5$•0.3 H$_2$O: C=62.15, H=5.65, N=11.69. Found: C=62.19, H=5.75, N=11.39.

EXAMPLE 94 trans-(4S)-4-(3,4-Difluorophenyl)-2-oxo-
oxazolidine-3-carboxylic acid {1-[4-(2-
cyanophenyl)-cyclohexyl]azetidin-3-yl-amide

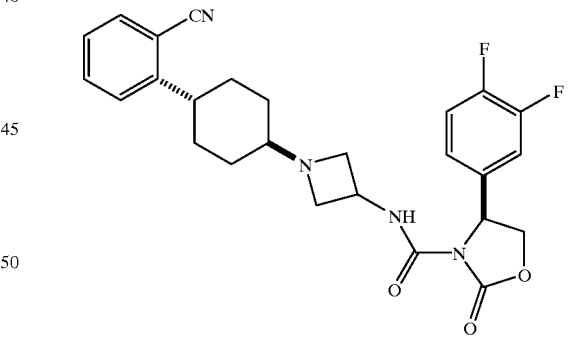

$^1$H NMR (CDCl$_3$, 400 MHz) consistent with assigned structure.

FABLRMS m/e 481 g/mole (M$^+$+H, C$_{26}$ $_{26}$F$_2$N$_4$O$_3$=480.51 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

Anal. Calcd for C$_{26}$ $_{26}$F$_2$N$_4$O$_3$•0.2 CHCl$_3$ and 0.2 H$_2$O: C=63.84, H=5.44, N=11.43. Found: C=63.85, H=5.30, N=11.41.

EXAMPLE 95 trans-(4S)-3-{1-[4-(2-Methoxyphenyl)cyclohexyl]
azetidin-3-ylcarbamoyl}-4-(3,4-difluorophenyl)-6-
methoxymethyl-2-oxo-1,2,3,4-tetrahydropyrimidine-
5-carboxylic acid methyl ester

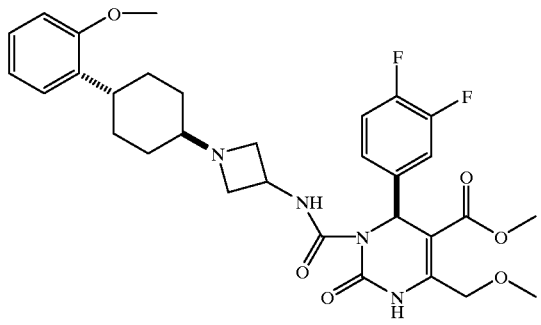

$^1$H NMR (CDCl$_3$, 400 MHz) consistent with assigned structure.

FABLRMS m/e 599 g/mole (M$^+$+H, C$_{31}$H$_{36}$F$_2$N$_4$O$_6$= 598.64 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

Anal. Calcd for C$_{31}$H$_{36}$F$_2$N$_4$O$_6$: C=62.19, H=6.06, N=9.35. Found: C=62.18, H=5.96, N=9.28.

EXAMPLE 96 trans-(4S)-4-(3,4-Difluorophenyl)-2-oxo-
oxazolidine-3- carboxylic acid {1-[4-(2-
methoxyphenyl)-cyclohexyl]azetidin-3-yl-amide

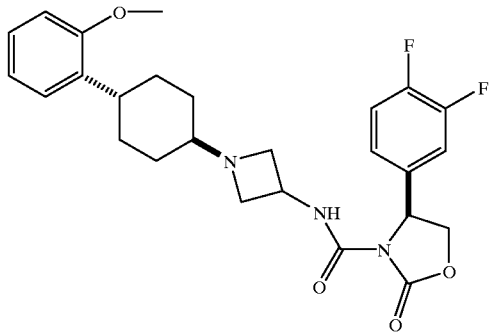

$^1$H NMR (CDCl$_3$, 400 MHz) consistent with assigned structure.

FABLRMS m/e 486 g/mole (M$^+$+H, C$_{26}$ $_{29}$F$_2$N$_3$O$_4$= 485.53 g/mole.).

HPLC (Vydac; C18; diameter 4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

Anal. Calcd for C$_{26}$ $_{29}$F$_2$N$_3$O$_4$: C=64.31, H=6.02, N=8.65. Found: C=64.28, H=6.04, N=8.68.

EXAMPLE 97

(Low Rf) (4S)-3-{1-[4-(2-pyridyl)cyclohexyl]
azetidin-3-ylcarbamoyl}-4-(3,4-difluorophenyl)-6-
methoxymethyl-2-oxo-1,2,3,4-tetrahydropyrimidine-
5-carboxylic acid methyl ester hydrochloride

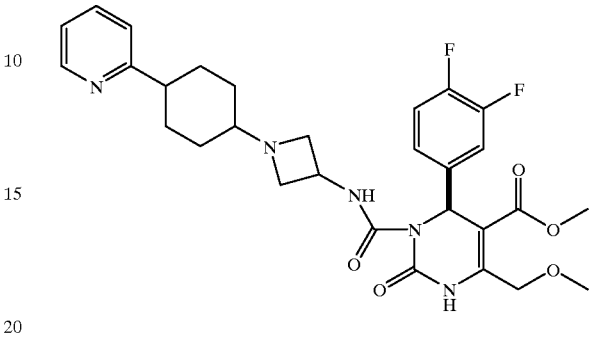

$^1$H NMR (CDCl$_3$, 400 MHz) consistent with assigned structure.

FABLRMS m/e 570 g/mole (M$^+$+H, C$_{29}$H$_{33}$F$_2$N$_5$O$_5$= 466.577 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 mmin flow rate) focus=215 nm; 100% pure.

Anal. Calcd for C$_{29}$H$_{33}$F$_2$N$_5$O$_5$: C=61.12, H=6.04, N=11.88. Found: C=61.14, H=5.90, N=11.88.

EXAMPLE 98

(Lower Rf) (4S)-4-(3,4-Difluorophenyl)-2-oxo-
oxazolidine-3-carboxylic acid {1-[4-(2-pyridyl)-
cyclohexyl]azetidin-3-ylmethyl-amide

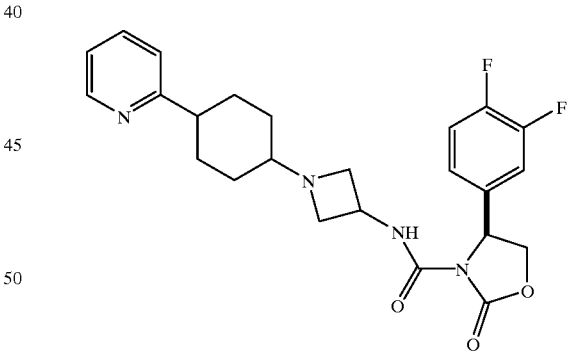

$^1$H NMR (CDCl$_3$, 400 MHz) consistent with assigned structure.

FABLRMS m/e 457 g/mole (M$^+$+H, C$_{24}$ $_{26}$F$_2$N$_4$O$_4$= 456.49 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

Anal. Calcd for C$_{24}$ $_{26}$F$_2$N$_4$O$_4$•0.2 CHCl$_3$ and 0.45 EtOAc: C=60.05, H=5.78, N=10.77. Found: C=59.92, H=5.77, N=10.79.

EXAMPLE 99 trans-(4S)-3-{1-[4-(2-Carboxymethoxyphenyl)cyclohexyl]azetidin-3-ylmethylcarbamoyl}-4-(3,4-difluorophenyl)-6-methoxymethyl-2-oxo-1,2,3,4-tetrahydropyrimidine-5-carboxylic acid methyl ester

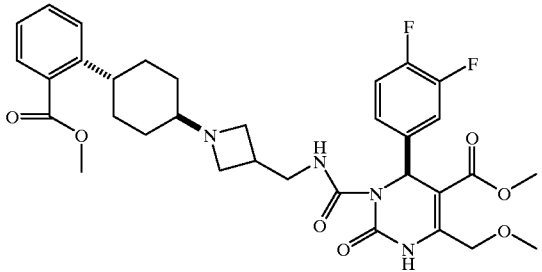

$^1$H NMR (CDCl$_3$, 400 MHz) consistent with assigned structure.

FABLRMS m/e 641 g/mole (M$^+$+H, C$_{33}$H$_{38}$F$_2$N$_4$O$_7$= 640.69 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 97% pure.

Anal. Calcd for C$_{33}$H$_{38}$F$_2$N$_4$O$_7$•0.2 CHCl$_3$ and 0.25 EtOAc: C=59.82, H=5.90, N=8.16. Found: C=59.81, H=5.80, N=8.13.

EXAMPLE 100 trans-(4S)-4-(3,4-Difluorophenyl)-2-oxo-oxazolidine-3-carboxylic acid {1-[4-(2-carboxymethoxyphenyl)-cyclohexyl]azetidin-3-ylmethyl-amide

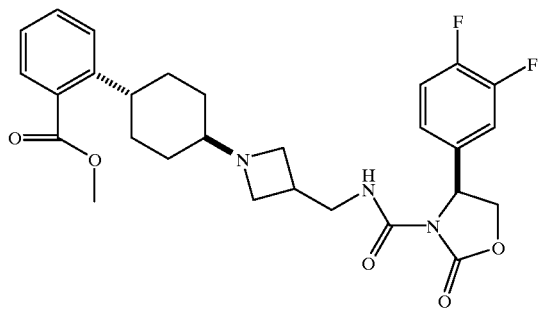

$^1$H NMR (CDCl$_3$, 400 MHz) consistent with assigned structure.

FABLRMS m/e 528 g/mole (M$^+$+H, C$_{28}$H$_{31}$F$_2$N$_3$O$_5$= 527.57 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 98% pure.

Anal. Calcd for C$_{28}$H$_{31}$F$_2$N$_3$O$_5$•0.35 CHCl$_3$ and 0.1 EtOAc: C=59.72, H=5.61, N=7.27. Found: C=59.72, H=5.78, N=7.37.

EXAMPLE 101 trans-(4S)-3-{1-[4-(2-Carboxyethoxyphenyl)-cyclohexyl]azetidin-3-ylmethylcarbamoyl}-4-(3,4-difluorophenyl)-6-methoxymethyl-2-oxo-1,2,3,4-tetrahydropyrimidine-5-carboxylic acid methyl ester

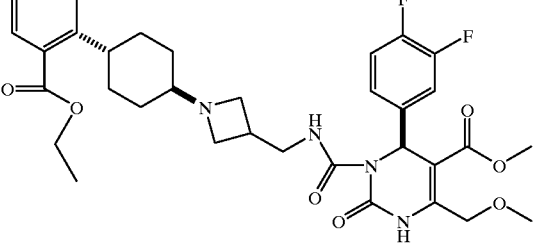

$^1$H NMR (CDCl$_3$, 400 MHz) consistent mith assigned structure.

FABLRMS m/e 655 g/mole (M$^+$+H, C$_{34}$H$_{40}$F$_2$N$_4$O$_7$= 654.71 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 98% pure.

Anal. Calcd for C$_{34}$H$_{40}$F$_2$N$_4$O$_7$•0.3 EtOAc: C=62.06, H=6.27, N=8.23. Found: C=61.91, H=6.09, N=8.25.

EXAMPLE 102 trans-(4S)-3-{1-[4-(2-Carboxyethoxyphenyl)-cyclohexyl]azetidin-3-ylmethylcarbamoyl}-4-(3,4-difluorophenyl)-2-oxo-1,2,3,4-tetrahydro-4H-furo[3,4-d]pyrimidine

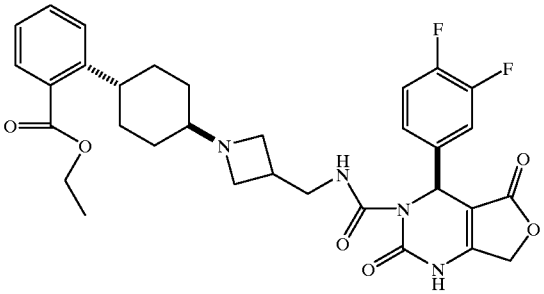

$^1$H NMR (CDCl$_3$, 400 MHz) consistent with assigned structure.

FABLRMS m/e 609 g/mole (M$^+$+H, C$_{32}$H$_{34}$F$_2$N$_4$O$_6$= 608.64 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 98% pure.

Anal. Calcd for C$_{32}$H$_{34}$F$_2$N$_4$O$_6$•0.4 EtOAc: C=62.67, H=5.82, N=8.70. Found: C=62.31, H=5.71, N=8.83.

EXAMPLE 103 trans-(4S)-4-(3,4-Difluorophenyl)-2-oxo-oxazolidine-3-carboxylic acid {1-[4-(2-carboxyethoxyphenyl)-cyclohexyl]azetidin-3-ylmethyl-amide

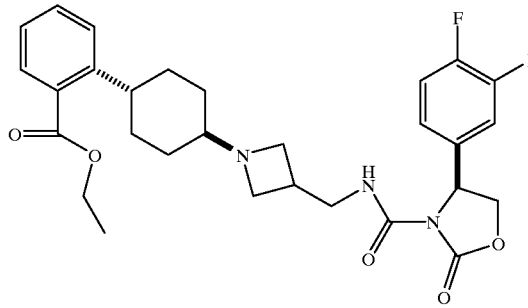

$^1$H NMR (CDCl$_3$, 400 MHz) consistent with assigned structure.

FABLRMS m/e 542 g/mole (M$^+$+H, C$_{29}$H$_{33}$F$_2$N$_3$O$_5$= 541.59 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 98% pure.

Anal. Calcd for C$_{29}$H$_{33}$F$_2$N$_3$O$_5$•0.3 EtOAc: C=63.85, H=6.28, N=7.40. Found: C=63.54, H=6.12, N=7.43.

EXAMPLE 104

(Diast A) (4S)-4-(3,4-Difluorophenyl)-2-oxo-oxazolidine-3-carboxylic acid{1-[4-(2-pyridyl)cyclohexyl]-3-hydroxy-pyrrolidin-4-yl}amide

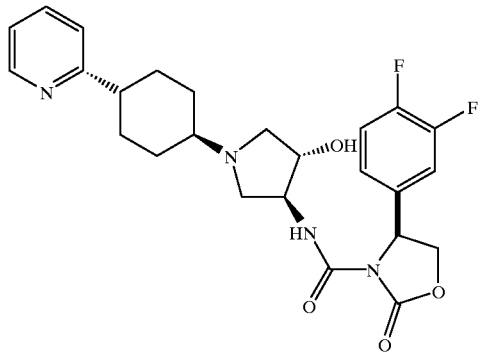

$^1$H NMR (CDCl$_3$, 400 MHz) consistent with assigned structure.

FABLRMS m/e 487.2 g/mole (M$^+$+H, C$_{25}$ $_{28}$F$_2$N$_4$O$_4$= 486.51 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

EXAMPLE 105

(Diast B) (4S)-4-(3,4-Difluorophenyl)-2-oxo-oxazolidine-3-carboxylic acid{1-[4-(2-pyridyl)cyclohexyl]-3-hydroxy-pyrrolidin-4-yl}amide

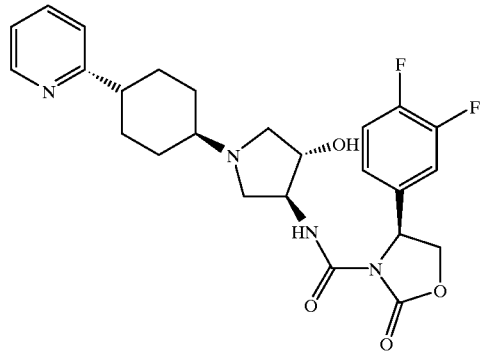

$^1$H NMR (CDCl$_3$, 400 MHz) consistent with assigned structure.

FABLRMS m/e 487.2 g/mole (M$^+$+H, C$_{25}$ $_{28}$F$_2$N$_4$O$_4$= 486.51 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 100% pure.

EXAMPLE 106

(Diast A) (4S)-4-(3,4-Difluorophenyl)-2-oxo-oxazolidine-3-carboxylic acid{1-[4-(2-cyanophenyl)cyclohexyl]-3-hydroxy-pyrrolidin-4-yl}amide

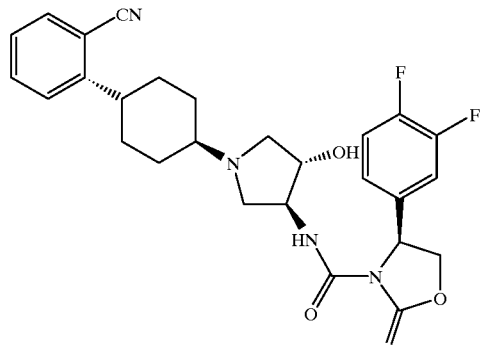

$^1$H NMR (CDCl$_3$, 400 MHz) consistent with assigned structure.

FABLRMS m/e 511 g/mole (M$^+$+H, C$_{27}$ $_{28}$F$_2$N$_4$O$_4$= 510.54 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 mmin flow rate) focus=215 nm; 99% pure.

Anal. Calcd for C$_{27}$ $_{28}$F$_2$N$_4$O$_4$•0.5 H$_2$O and 0.25 Et$_2$O: C=62.50, H=5.90, N=10.41. Found: C=62.55, H=5.69, N=10.36.

EXAMPLE 107

(Diast B) (4S)-4-(3,4-Difluorophenyl)-2-oxo-oxazolidine-3-carboxylic acid{1-[4-(2-cyanophenyl)cyclohexyl]-3-hydroxy-pyrrolidin-4-yl}amide

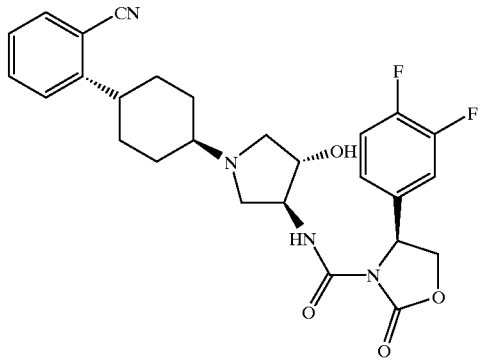

$^{1}$H NMR (CDCl$_{3}$, 400 MHz) consistent with assigned structure.

FABLRMS m/e 511 g/mole (M$^{+}$+H, C$_{27\ 28}$F$_{2}$N$_{4}$O$_{4}$= 510.54 g/mole.).

HPLC (Vydac; C18; diameter=4.6 mm; length=150 mm; gradient=H$_{2}$O [0.1% H$_{3}$PO$_{4}$]—CH$_{3}$CN, 95%-5%, 5%-95%, over 16 minutes, 2 ml/min flow rate) focus=215 nm; 99% pure.

Anal. Calcd for C$_{27\ 28}$F$_{2}$N$_{4}$O$_{4}$•0.4 H$_{2}$O and 0.4 Et$_{2}$O: C=62.75, H=6.04, N=10.24. Found: C=62.77, H=5.71, N=10.23.

EXAMPLE 108

(Racemic@ pyrrolidine) (4S)-3-{1-[4-(2-Pyridyl)-cyclohexyl]-3-hydroxy-pyrrolidin-4-ylcarbamoyl}-4-(3,4-difluorophenyl)-6-methyl-2-oxo-1,2,3,4-tetrahydropyrimidine-5-carboxylic acid methyl ester

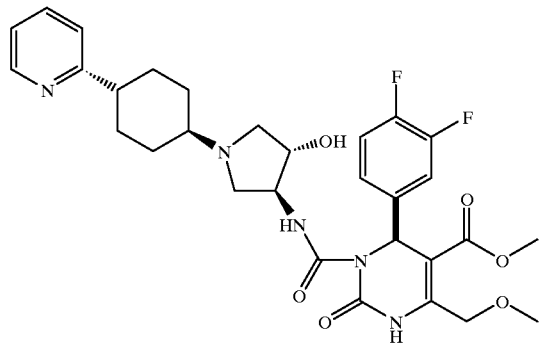

$^{1}$H NMR (CDCl$_{3}$, 400 MHz) consistent with assigned structure.

FABLRMS m/e 600 g/mole (M$^{+}$+H, C$_{30}$H$_{35}$F$_{2}$N$_{5}$O$_{6}$= 599.63 g/mole.).

HPLC (Vydac; C18; diameter 4.6 mm; length=150 mm; gradient=H$_{2}$O [0.1% H$_{3}$PO$_{4}$]—CH$_{3}$CN, 95%-5%, 5%-95%, over 16 minutes, 2 ml/min flow rate) focus=215 nm; 98% pure.

Anal. Calcd for C$_{30}$H$_{35}$F$_{2}$N$_{5}$O$_{6}$•0.55 H$_{2}$O and 0.35 Et$_{2}$O: C=59.34, H=6.28, N=11.02. Found: C=59.32, H=5.99, N=10.98.

EXAMPLE 109 trans-(4S,5S)-4-(3,4-Difluorophenyl)-5-methyl-2-oxo-oxazolidine-3-carboxylic acid {1-[4-(2-cyanophenyl)-cyclohexyl]3-hydroxy-azetidin-3-ylmethyl-amide

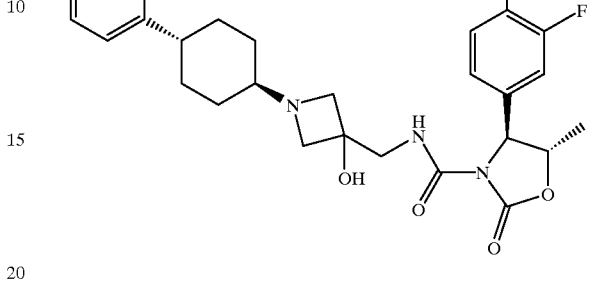

$^{1}$H NMR (CDCl$_{3}$, 400 MHz) consistent mith assigned structure.

FABLRMS m/e 525.0 g/mole (M$^{+}$+H, C$_{28}$H$_{30}$F$_{2}$N$_{4}$O$_{4}$= 524.56 g/mole.).

HPLC (Vydac; C18; diameter=4.6 mm; length=150 mm; gradient=H$_{2}$O [0.1% H$_{3}$PO$_{4}$]—CH$_{3}$CN, 95%-5%, 5%-95%, over 16 minutes, 2 ml/min flow rate) focus=215 nm; 99% pure.

Anal. Calcd for C$_{28}$H$_{30}$F$_{2}$N$_{4}$O$_{4}$•0.40 H$_{2}$O and 1.30 CH$_{2}$Cl$_{2}$: C=54.80, H=5.24, N=8.73. Found: C=54.78, H=5.25, N=8.67.

EXAMPLE 110 trans-(4S,5S)-4-(3,4-Difluorophenyl)-5-methyl-2-oxo-oxazolidine-3-carboxylic acid {1-[4-(2-pyridyl)-cyclohexyl]3-hydroxy-azetidin-3-ylmethyl-amide

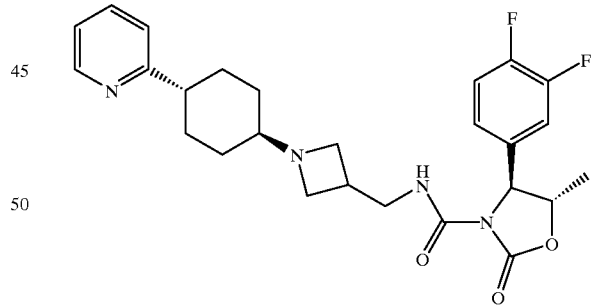

$^{1}$H NMR (CDCl$_{3}$, 400 MHz) consistent with assigned structure.

FABLRMS m/e 485 g/mole (M$^{+}$+H, C$_{26}$H$_{30}$F$_{2}$N$_{4}$O$_{3}$= 484.54 g/mole.).

HPLC (Vydac; C18; diameter=4.6 mm; length=150 mm; gradient=H$_{2}$O [0.1% H$_{3}$PO$_{4}$]—CH$_{3}$CN, 95%-5%, 5%-95%, over 16 minutes, 2 ml/min flow rate) focus=215 nm; 97% pure.

Anal. Calcd for C$_{26}$H$_{30}$F$_{2}$N$_{4}$O$_{3}$•0.15 CH$_{2}$Cl$_{2}$: C=63.15, H=6.14, N=11.27. Found: C=63.40, H=6.00, N=11.24.

EXAMPLE 111 trans-(4S,5S)-4-(3,4-Difluorophenyl)-5-methyl-2-oxo-oxazolidine-3-carboxylic acid {1-[4-(2-cyanophenyl)-cyclohexyl]azetidin-3-ylmethyl-amide

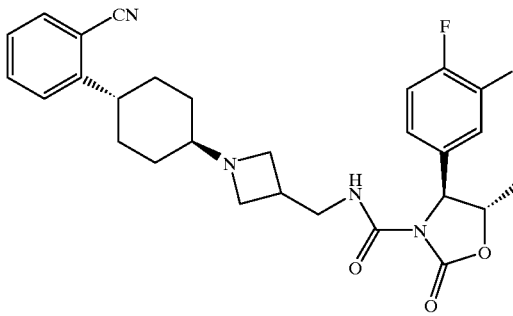

$^1$H NMR (CDCl$_3$, 400 MHz) consistent with assigned structure.

FABLRMS m/e 509 g/mole (M$^+$+H, C$_{28}$H$_{30}$F$_2$N$_4$O$_3$= 508.56 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 97% pure.

Anal. Calcd for C$_{28}$H$_{30}$F$_2$N$_4$O$_3$•0.05 Et$_2$O and 0.10 CH$_2$Cl$_2$: C=65.27, H=5.94, N=10.76. Found: C=65.36, H=65.36, N=10.73.

EXAMPLE 112 trans-(4±)-3-{1-[4-(2-Cyanophenyl)cyclohexyl]azetidin-3-ylmethylcarbamoyl}-4-(3,4-difluorophenyl)-2-oxo-1,2,3,4-tetrahydropyrimidine-5-carboxylic acid methyl ester

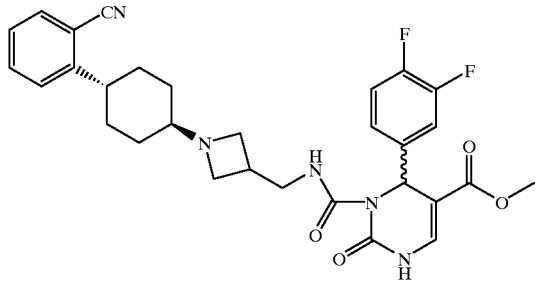

$^1$H NMR (CDCl$_3$, 400 MHz) consistent with assigned structure.

FABLRMS m/e 564 g/mole (M$^+$+H, C$_{30}$H$_{31}$F$_2$N$_5$O$_4$= 563.60 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 mmin flow rate) focus=215 nm; 98% pure.

Anal. Calcd for C$_{30}$H$_{31}$F$_2$N$_5$O$_4$•0.15 Et$_2$O and 0.15 CH$_2$Cl$_2$: C=62.86, H=5.63, N=11.92. Found: C=62.88, H=5.74, N=11.99.

EXAMPLE 113 trans-(4±)-3-{1-[4-(2-Cyanophenyl)cyclohexyl]3-hydroxy-azetidin-3-ylmethylcarbamoyl}-4-(3,4-difluorophenyl)-2-oxo-1,2,3,4-tetrahydropyrimidine-5-carboxylic acid methyl ester

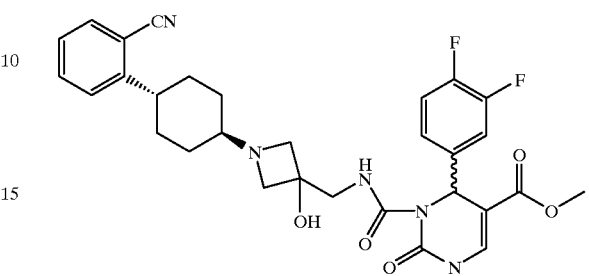

$^1$H NMR (CDCl$_3$, 400 MHz) consistent with assigned structure.

FABLRMS m/e 580 g/mole (M$^+$+H, C$_{30}$H$_{31}$F$_2$N$_5$O$_5$= 579.60 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 98% pure.

Anal. Calcd for C$_{30}$H$_{31}$F$_2$N$_5$O$_5$.0.05 CH$_2$Cl$_2$: C=61.81, H=5.37, N=12.00. Found: C=61.61, H=5.57, N=12.22.

EXAMPLE 114 trans-(4±)-3-{1-[4-(2-Pyridyl)cyclohexyl]3-hydroxy-azetidin-3-ylmethylcarbamoyl}-4-(3,4-difluorophenyl)-2-oxo-1,2,3,4-tetrahydropyrimidine-5-carboxylic acid methyl ester

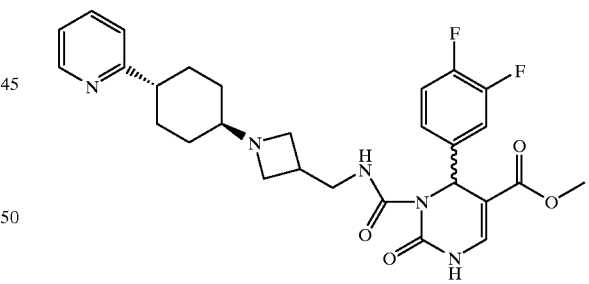

$^1$H NMR (CDCl$_3$, 400 MHz) consistent with assigned structure.

FABLRMS m/e 540 g/mole (M$^+$+H, C$_{28}$H$_{31}$F$_2$N$_5$O$_4$= 539.58 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 95% pure.

Anal. Calcd for C$_{28}$H$_{31}$F$_2$N$_5$O$_4$•0.05 Et$_2$O and 0.45 CH$_2$Cl$_2$: C=59.17, H=5.62, N=12.04. Found: C=59.18, H=5.62, N=12.04.

EXAMPLE 115 trans-(3R,4S,5S)-4-(3,4-Difluorophenyl)-5-methyl-2-oxo-oxazolidine-3-carboxylic acid {1-[4-(2-pyridyl)-cyclohexyl]azetidin-3-yl}methyl-amide

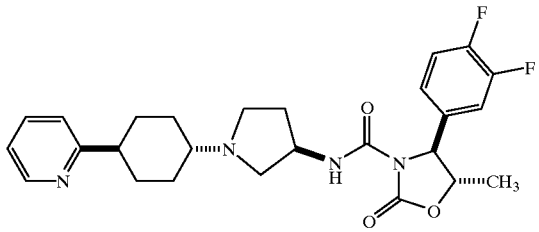

$^1$H NMR (CDCl$_3$, 400 MHz) consistent with assigned structure.

FABLRMS m/e 485 g/mole (M$^+$+H, C$_{26}$H$_{30}$F$_2$N$_4$O$_3$= 484.548 g/mole.).

HPLC (Vydac; C18; diameter=4.6 mm; length=150 mm; gradient=H$_2$O [0.1% H$_3$PO$_4$]—CH$_3$CN, 95%-5%, 5%-95%, over 16 minutes, 2 ml/min flow rate) focus=215 nm; 96.4% pure.

EXAMPLE 116

As a specific embodiment of an oral composition, 100 mg of the compound of Example 1 is formulated with sufficient finely divided lactose to provide a total amount of 580 to 590 mg to fill a size O hard gel capsule.

EXAMPLE 117

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦50 nM.

EXAMPLE 118

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 916 well cell harvester. Filters were washed three times with ice cold buffer and bound radioactivity was determined (Ki).

All of the compounds of the present invention prepared in the foregoing Examples were found to have alpha 1a Ki values of less than 50 nM as determined via the screening assay described in Example 117, except for Examples 12 (<200 nM), 16 (ca. 800 nM) and 20 (inactive). All of the compounds were further found to be at least about 50-fold more selective in binding to alpha 1a receptors versus binding to the alpha 1b and alpha 1d receptors, as determined via the selective binding assay described in the preceding paragraph, except for Examples 12 (at least about 3-fold), 16 (at least about 8-fold), 20, and 78 (about 37-fold). All of the compounds except for those of Examples 8, 12, 14, 16, 19, 20, 21, 24, 30, 40, 47, 50, 51, 52, 67, 69, 70, 76, 77 and 78 were at least about 100-fold more selective in binding to alpha 1a receptors versus alpha 1b and 1d receptors.

EXAMPLE 119

EXEMPLARY COUNTERSCREENS

1. Assay Title: Dopamine D2, D3, D4 in vitro Screen
Objective of the Assay:

The objective of this assay is to eliminate agents which specifically affect binding of [3H] spiperone to cells expressing human dopamine receptors D2, D3 or D4.

Method:

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a
Obiective of the Assay

The objective of this assay is to eliminate agents which specifically affect binding to cloned human 5HT1a receptor
Method:

Modified from Schelegel and Peroutka Biochemical Pharmacology 35: 1943–1949 (1986).

Mamnalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and lmg/ml ascorbate. Non-specific binding is defined using 10 μM propranolol. The assay is terminated after a 1 hour incubation at room temperature by rapid filtration over GF/Cfilters

EXAMPLE 120

EXEMPLARY FUNCTIONAL ASSAYS

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2:.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/ 95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. pA2 ($-\log K_b$) values were obtained from Schild plot when three or more concentrations were tested. When less than three concentrations of antagonist are tested, $K_b$ values are calculated according to the following formula $$K_b=[B], x-1$$

where x is the ratio of $EC_{50}$ of agonist in the presence and absence of antagonist and [B] is the antagonist concentration.

2. Measurement of Intra-Urethral Pressure in Anesthetized Dogs

PURPOSE:

Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS:

Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cinnulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50's}$ for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephriie responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonist that prevent the increase in intra-urethral pressure to phenylephrine without any activity at the vasculature.

While the foregoing specification teaches, the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

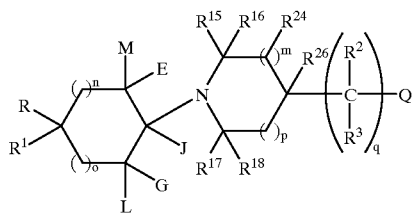

wherein Q is

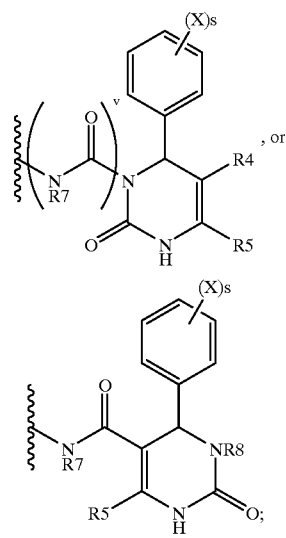

E, G, L and M are each independently selected from hydrogen, $C_{1-8}$ alkyl, $C_{3-8}$ cycloalkyl, $(CH_2)_{0-4}OR^6$, $(CH_2)_{0-4}N(R^{19})_2$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$;

J is selected from hydrogen, $C_{1-8}$ alkyl, $C_{3-8}$ cycloalkyl, $(CH_2)_{1-4}OR^6$, $(CH_2)_{1-4}N(R^{19})_2$, $(CH_2)_{1-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$, or $(CH_2)_{0-4}SO_2N(R^{19})_2$;

$R^1$ is selected from unsubstituted, mono- or poly-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, pyridyl N-oxide (N→O), pyrazinyl, thienyl, thiazolyl, furanyl, quinazolinyl or naphthyl wherein the substituents on the pyridyl, pyrazinyl, thienyl, thiazolyl, furanyl, quinazolinyl, or naphthyl are independently selected from $CF_3$, cyano, nitro, $N(R^{19})_2$, $(CH_2)_{0-4}CO_2R^{19}$, $CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

R is selected from hydrogen, cyano, $OR^6$, $CO_2R^{19}$, $CON(R^{19})_2$, tetrazole, isooxadiazole, unsubstituted, mono- or poly-substituted phenyl wherein the substituents on the phenyl are independently selected from halogen, cyano, nitro, $OR^6$, $(CH_2)_{0-4}CO_2R^{19}$, $(CH_2)_{0-4}CON(R^{19})_2$, $N(R^{19})_2$, $NR^{19}COR^6$, $NR^{19}CON(R^{20})_2$, $NR^{19}SO_2R^6$, $NR^{19}SO_2N(R^{20})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, thienyl, furanyl or naphthyl wherein the substituents on the pyridyl, thienyl, furanyl or naphthyl are independently selected from $CF_3$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;

$R^2$, $R^3$ and $R^7$ are each independently selected from hydrogen, $C_{1-8}$ alkyl, $C_{4-8}$ cycloalkyl, $(CH_2)_{0-4}CO_2R^{19}$, $(CH_2)_{0-4}CON(R^{19})_2$, $(CH_2)_{0-4}COR^6$, $(CH_2)_{2-4}OR^6$, $(CH_2)_{1-4}CF_3$, $(CH_2)_{0-4}SO_2R^6$, $(CH_2)_{0-4}SO_2N(R^{19})_2$ or $(CH_2)_{1-4}CN$;

$R^4$ is selected from hydrogen, $(CH_2)_{0-4}COR^6$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$;

$R^5$, $R^8$, $R^{15}$, $R^{16}$, $R^{17}$ and $R^{18}$ are each independently selected from hydrogen, $C_{1-8}$ alkyl, $C_{3-8}$ cycloalkyl, $(CH_2)_{2-4}OR^6$ or $(CH_2)_{0-4}CF_3$;

$R^6$ is selected from hydrogen, $C_{1-8}$ alkyl, $C_{3-8}$ cycloalkyl or $(CH_2)_{0-4}CF_3$;

$R^{19}$ and $R^{20}$ are each independently selected from hydrogen, $C_{1-8}$ alkyl, $C_{3-8}$ cycloalkyl or $(CH_2)_{1-4}CF_3$;

$R^{24}$ and $R^{26}$ are each independently selected from hydrogen or $OR^{28}$;

$R^{28}$ is selected from hydrogen, $C_{1-8}$ alkyl, $C_{3-8}$ cycloalkyl or $(CH_2)_{0-4}CF_3$;

each X is independently selected from halogen, cyano, nitro, $C_{1-8}$ alkyl, $C_{3-8}$ cycloalkyl, $(CH_2)_{0-4}OR^6$ or $(CH_2)_{0-4}CF_3$;

m, p and q are each independently an integer of from zero to two provided that when q is zero, $R^{26}$ is hydrogen;

n, o, and s are each independently an integer of from zero to four; and v is an integer from zero to one;

or a pharmaceutically acceptable salt thereof.

2. The compound of claim 1, having the structure

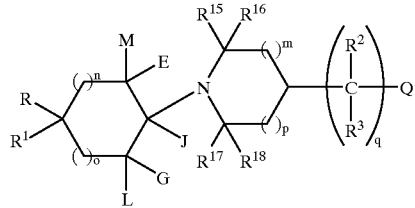

wherein $R^1$ is selected from unsubstituted, mono- or poly-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl, or naphthyl are independently selected from $CF_3$, cyano, nitro, $N(R^{19})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl; and $R^4$ is selected from $(CH_2)_{0-4}COR^6$, $(CH_2)_{0-4}CN$, $(CH_2)_{0-4}CF_3$, $(CH_2)_{0-4}CO_2R^{19}$, $(CH_2)_{0-4}CON(R^{19})_2$, $(CH_2)_{0-4}SO_2R^6$ or $(CH_2)_{0-4}SO_2N(R^{19})_2$;

or a pharmaceutically acceptable salt thereof.
3. The compound of claim 1, of the formula

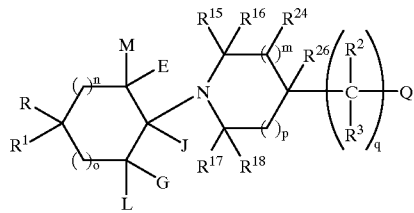

wherein

- E, G, L, M and J are each independently selected from hydrogen, $C_{1-8}$ alkyl, $C_{3-8}$ cycloalkyl, or $(CH_2)_{0-4}CF_3$;
- $R^1$ is selected from unsubstituted, mono-, di- or tri-substituted phenyl wherein the substituents on the phenyl are independently selected from halogen, $CF_3$, cyano, nitro, $OR^6$, $N(R^{19})_2$, $NR^{19}COR^{20}$, $NR^{19}CON(R^{20})_2$, $NR^{19}SO_2R^6$, $NR^{19}SO_2N(R^{20})_2$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$ or $C_{1-4}$ alkyl; or unsubstituted, mono-, di- or tri-substituted pyridyl, pyridyl N-oxide (N→O), pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;
- R is selected from hydrogen, cyano, $OR^6$, $CO_2R^{19}$, $CON(R^{19})_2$, tetrazole, isooxadiazole, unsubstituted, mono-, di- or tri-substituted phenyl wherein the substituents on the phenyl are independently selected from halogen, cyano, nitro, $OR^6$, $(CH_2)_{0-4}CO_2R^{19}$, $(CH_2)_{0-4}CON(R^{19})_2$, $N(R^{19})_2$, $NR^{19}COR^6$, $NR^{19}CON(R^{20})_2$, $NR^{19}SO_2R^6$, $NR^{19}SO_2N(R^{20})_2$, $(CH_2)_{0-4}SO_2N(R^{19})_2$, $(CH_2)_{0-4}SO_2R^6$ or $C_{1-4}$ alkyl; or unsubstituted, mono-, di- or tri-substituted pyridyl, thienyl, furanyl or naphthyl wherein the substituents on the pyridyl, thienyl, furanyl or naphthyl are independently selected from $CF_3$, $(CH_2)_{0-4}CO_2R^{19}$, $(CH_2)_{0-4}CON(R^{19})_2$, $(CH_2)_{0-4}SO_2N(R^{19})_2$, $(CH_2)_{0-4}SO_2R^6$, phenyl, $OR^6$, halogen, $C_{1-4}$ alkyl or $C_{3-8}$ cycloalkyl;
- $R^2$, $R^3$ and $R^7$ are each independently selected from hydrogen, $C_{1-8}$ alkyl, $C_{4-8}$ cycloalkyl or $(CH_2)_{1-4}CF_3$; and
- n is an integer from zero to two;

or a pharmaceutically acceptable salt thereof.
4. The compound of claim 3, selected from

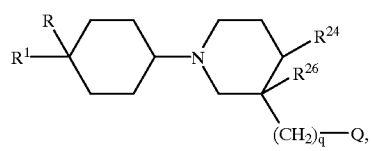

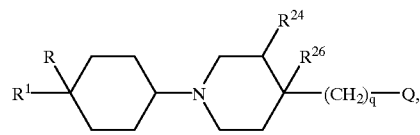

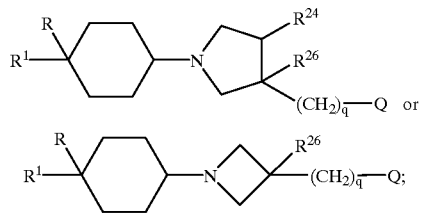

wherein Q is

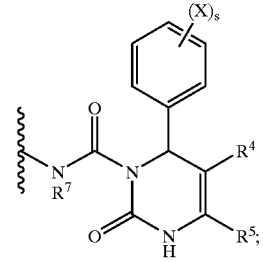

- $R^1$ is selected from unsubstituted, mono-, di- or tri-substituted phenyl wherein the substituents on the phenyl are independently selected from halogen, $CF_3$, cyano, nitro, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl; or unsubstituted, mono-, or di-substituted pyridyl or pyridyl N-oxide, wherein the substituents on the pyridyl or pyridyl N-oxide are independently selected from halogen, $CF_3$, cyano, $OR^6$, $(CH_2)_{0-2}CO_2R^{19}$, $(CH_2)_{0-2}CON(R^{19})_2$, $(CH_2)_{0-2}SO_2N(R^{19})_2$, $(CH_2)_{0-2}SO_2R^6$ or $C_{1-4}$ alkyl;
- R is selected from hydrogen, cyano, $OR^6$, $CO_2R^{19}$, $CON(R^{19})_2$, or unsubstituted, mono- or di-substituted phenyl wherein the substituents on the phenyl are independently selected from halogen, cyano, nitro, $OR^6$, $(CH_2)_{0-2}CO_2R^{19}$, $(CH_2)_{0-2}CON(R^{19})_2$ or $C_{1-4}$ alkyl;
- $R^4$ is selected from hydrogen, $COR^6$, $CO_2R^{19}$, $SO_2R^6$ or $CON(R^{19})_2$;
- $R^5$ is selected from hydrogen, $C_{1-6}$ alkyl, $C_{3-6}$ cycloalkyl, $(CH_2)_{0-3}OR^6$ or $(CH_2)_{0-3}CF_3$;
- $R^6$ is selected from hydrogen, $C_{1-6}$ alkyl, $C_{3-6}$ cycloalkyl or $(CH_2)_{0-3}CF_3$;
- $R^{19}$ is selected from hydrogen, $C_{1-6}$ alkyl, $C_{3-6}$ cycloalkyl or $(CH_2)_{1-3}CF_3$; and
- $R^{28}$ is selected from hydrogen, $C_{1-6}$ alkyl, $C_{3-6}$ cycloalkyl or $(CH_2)_{1-3}CF_3$;
- s is an integer from zero to three;

or a pharmaceutically acceptable salt thereof.
5. The compound of claim 4, selected from

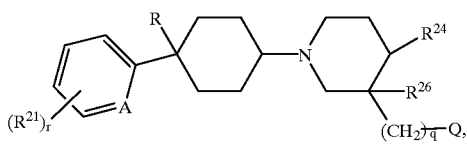

-continued

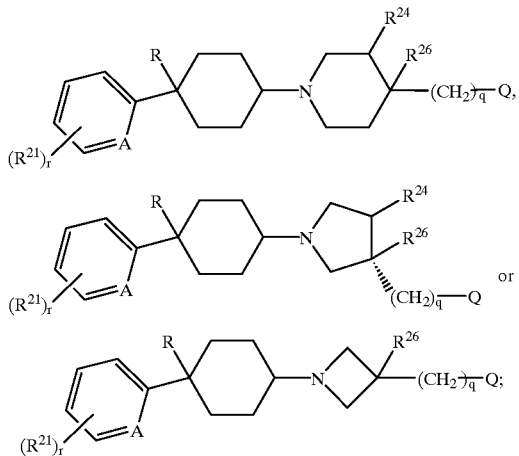

wherein Q is

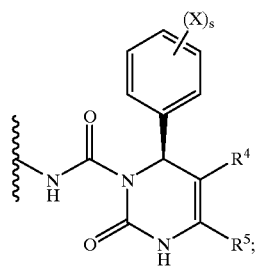

R is selected from hydrogen, OR$^6$ or cyano;
A is selected from C—R$^{21}$ or N or N→O;
each X is a halogen;
each R$^{21}$ is independently selected from hydrogen, halogen, hydroxy, cyano, OC$_{1-4}$ alkyl, OCF$_3$, OCH$_2$CF$_3$, CO$_2$-C$_{1-4}$ alkyl, CONH$_2$, SO$_2$NH$_2$ or SO$_2$C$_{1-4}$ alkyl;
R$^{28}$ is selected from hydrogen, C$_{1-4}$ alkyl, or (CH$_2$)$_{0-2}$CF$_3$; and
r is an integer from zero to two;
or a pharmaceutically acceptable salt thereof.

6. The compound of claim 5, wherein Q is

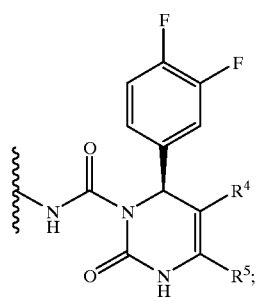

R is selected from hydrogen, hydroxy or cyano;
A is selected from C—R$^{21}$ or N;

R$^4$ is CO$_2$R$^{19}$;
R$^5$ is (CH$_2$)$_{0-3}$OR$^6$; and
q is an integer from zero to one;
or a pharmaceutically acceptable salt thereof.

7. The compound of claim 6, selected from
(4S)-3-{1-[4-(2-cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester;

(4S)-cis-3-{1-[4-(2-cyano-phenyl)-cyclohexyl]-(3R)-pyrrolidin-3-ylcarbamoyl}-4-(3,4-difluoro-phenyl)-6-methyoxymethyl-2-oxo-1,2,3,4-tetrahydropyrimidine-5-carboxylic acid methyl ester;

(4S)-trans-4-(3,4-difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-cis-4-(3,4-difluoro-phenyl)-3-{1-[4-(2-ethoxycarbonyl-phenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;

(4S)-trans-4-(3,4-difluorophenyl)-3-[1-(4-pyridin-2-yl-cyclohexyl)-(3R)-pyrro-lidin-3-ylcarbamoyl]-6-methoxymethyl-2-oxo-1,2,3,4-tetrahydro-pyrimidine-5-carboxylic acid methyl ester;

(4S)-cis-4-(3,4-difluorophenyl)-3-[1-(4-pyridin-2-yl-cyclohexyl)-(3R)-pyrrolidin-3-ylcarbomoyl]-6-methoxymethyl-2-oxo-1,2,3,4-tetrahydro-pyrimidine-5-carboxylic acid methyl ester;

(4S)-trans-4-(3,4-difluorophenyl)-6-methoxymethyl-3-{1-[4-(2-methoxyl-phenyl)-cyclohexl]-(3R)-pyrrolidin-3-ylcarbamoyl}-2-oxo-1,2,3,4-tetrahydro-pyrimidine-5-carboxylic acid methyl ester;

(4S)-cis-4-(3,4-difluoro-phenyl)-6-methoxymethyl-3-{1-[4-(2-methoxyl-phenyl)-cyclohexyl]-(3R)-pyrrolidin-3-ylcarbamoyl}-2-oxo-1,2,3,4-tetrahydro-pyrimidine-5-carboxylic acid methyl ester;

(4S)-cis-4-(3,4-difluoro-phenyl)-3-[1-(4-hydroxy-4-pyridin-2-yl-cyclohexyl)-(3R)-pyrrolidin-ylcarbamoyl]-6-methoxymethyl-2-oxo-1,2,3,4-tetrahydro-pyrimidine-5-carboxylic acid methyl ester;

(4S)-trans-4-(3,4-difluoro-phenyl)-3-[1-(4-hydroxy-4-pyridin-2-yl-cyclohexyl)-(3R)-pyrrolidin-3-ylcarbamoyl]-6-methoxymethyl-2-oxo-1,2,3,4-tetrahydro-pyrimidine-5-carboxylic acid methyl ester;

(4S)-4-(3,4-difluoro-phenyl)-3-{1-[4-(2-hydroxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester;

(4S)-cis-4-(3,4-difluoro-phenyl)-6-methoxymethyl-3-{1-[4-(2-hydroxy-phenyl)-cyclohexyl]-(3R)-pyrrolidin-3-ylcarbamoyl}-2-oxo-1,2,3,4-tetrahydro-pyrimidine-5-carboxylic acid methyl ester;

and the pharmaceutically acceptable salts thereof.

8. The compound of claim 5, wherein
R is H or OH;

Q is

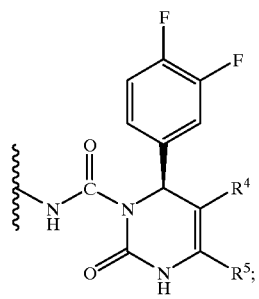

R[4] is H or CO$_2$CH$_3$;
R[5] is H, CH$_3$, or CH$_2$OCH$_3$; and
q is an integer from zero to one; or a pharmaceutically acceptable salt thereof.

9. The compound of claim 8, selected from
(4S)-trans-4-(3-,4-difluoro-phenyl)-3-{1-4-(2-fluoro-phenyl)-cyclohexyl]-(3R)-pyrrolidin-3-ylcarbamoyl}-6-methoxymethyl-1,2,3,4-tetrahydro-pyrimidine-5-carboxylic acid methyl ester;
(4S)-trans-4-(3,4-difluoro-phenyl)-3-{1-[4-(4-fluoro-2-methoxy-phenyl)-cyclohexyl]-(3R)-pyrrolidin-3-ylcarbamoyl}-6-methoxymethyl-2-oxo-1,2,3,4-tetrahydro-pyrimidine-5-carboxylic acid methyl ester;
(4S)-4-(3,4-difluoro-phenyl)-3-{1-[4-(2-fluoro-phenyl)-4-hydroxy-cyclohexyl]-(3R)-pyrrolidin-3-ylcarbamoyl}-6-methoxymethyl-1,2,3,4-tetrahydro-pyrimidine-5-carboxylic acid methyl ester;
(4S)-4-(3,4-difluorophenyl)-3-{1-[4-hydroxy-4-(2-trifluoromethylphenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;
(4S)-4-(3,4-difluorophenyl)-6-methoxymethyl-2-oxo-3-{1-[4-(2-trifluoromethylphenyl)-cyclohexyl]-(3R)-pyrrolidin-3-ylcarbamoyl}-1,2,3,4-tetrahydropyrimidine-5-carboxylic acid methyl ester;
(4S)-4-(3,4-difluorophenyl)-3-{1-[4-(4-fluorophenyl)-4-hydroxy-cyclohexyl]-(3R)-pyrrolidin-3-ylcarbamoyl}-6-methoxymethyl-2-oxo-1,2,3,4-tetrahydropyrimidine-5-carboxylic acid methyl ester;
(4S)-4-(3,4-difluorophenyl)-3-{1-[4-(4-fluorophenyl)-4-hydroxy-cyclohexyl]-(3R)-pyrrolidin-3-ylcarbamoyl}-6-methyl-2-oxo-1,2,3,4-tetrahydropyrimidine-5-carboxylic acid methyl ester;
(4S)-4-(3,4-difluorophenyl)-3-{1-[4-(4-fluorophenyl)-cyclohexyl]-(3R)-pyrrolidin-3-ylcarbamoyl}-6-methyl-2-oxo-1,2,3,4-tetrahydropyrimidine-5-carboxylic acid methyl ester;
(4S)-4-(3,4-difluorophenyl)-3-{1-[4-(4-fluorophenyl)-cyclohexyl]-(3R)-pyrrolidin-3-ylcarbamoyl}-6-methoxymethyl-2-oxo-1,2,3,4-tetrahydropyrimidine-5-carboxylic acid methyl ester;
(4S)-4-(3,4-difluorophenyl)-3-{1-[4-(4-fluorophenyl)-4-hydroxy-cyclohexyl]-(3R)-pyrrolidin-3-ylcarbamoyl}-2-oxo-1,2,3,4-tetrahydropyrimidine-5-carboxylic acid methyl ester;
(4S)-3-{1-[4-(4-cyanophenyl)-4-hydroxycyclohexyl]-(3R)-pyrrolidin-3-ylcarbamoyl}-4-(3,4-difluorophenyl)-6-methoxymethyl-2-oxo-1,2,3,4-tetrahydropyrimidine-5-carboxylic acid methyl ester;
(4S)-3-{1-[4-(4-cyanophenyl)-cyclohexyl]-(3R)-pyrrolidin-3-ylcarbamoyl}-4-(3,4-difluorophenyl)-6-methyl-2-oxo-1,2,3,4-tetrahydropyrimidine-5-carboxylic acid methyl ester;
(4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester;
(4S)-3-{1-[4-(2-cyano-phenyl)-cyclohexyl]-(3R)-pyrrolidin-3-ylcarbamoyl}-4-(3,4-difluoro-phenyl)-6-methyl-2-oxo-1,2,3,4-tetrahydro-pyrimidine-5-carboxylic acid methyl ester;
(4S)-3-{1-[4-(2-cyano-4-fluoro-phenyl)-cyclohexyl]-(3R)-pyrrolidin-3-ylcarbamoyl]-4-(3,4-difluoro-phenyl)-6-methoxymethyl-2-oxo-1,2,3,4-tetrahydro-pyrimidine-5-carboxylic acid methyl ester;
(4S)-4-(3,4-difluoro-phenyl)-3-{1-[4-(4-fluoro-2-hydroxy-phenyl)-cyclohexyl]-(3R)pyrrolidin-3-ylcarbamoyl}-6-methoxymethyl-2-oxo-1,2,3,4-tetrahydro-pyrimidine-5-carboxylic acid methyl ester;
(4S)-4-(3,4-difluoro-phenyl)-3-{1-[4-(2-fluoro-phenyl)-4-hydroxy-cyclohex-1-yl]-(3R)-pyrrolidin-3-ylcarbamoyl}-6-methyl-2-oxo-1,2,3,4-tetrahydro-pyrimidine-5-carboxylic acid methyl ester;
(4S)-trans-4-(3,4-difluoro-phenyl)-3-{1-[4-(2-fluoro-phenyl)-cyclohexyl]-(3R)-pyrrolidin-3-ylcarbamoyl}-6-methyl-2-oxo-1,2,3,4-tetrahydro-pyrimidine-5-carboxylic acid methyl ester;
(4S)-cis-4-(3,4-difluoro-phenyl)-3-[1-(4-hydroxy-4-pyridin-2-yl-cyclohexyl)-(3R)-pyrrolidin-3-ylcarbamoyl]-2-oxo-1,2,3,4-tetrahydro-pyrimidine-5-carboxylic acid methyl ester;
(4S)-trans-4-(3,4-difluoro-phenyl)-3-[1-(4-pyridin-2-yl-cyclohexyl)-(3R)-pyrrolidin-3-ylcarbamoyl]-2-oxo-1,2,3,4-tetrahydro-pyrimidine-5-carboxylic acid methyl ester;
(4S)-trans-3{1-[4-(2-cyano-phenyl)-piperidin-1-yl]-(3R)-pyrrolidin-3-ylcarbamoly}-4-(3,4-difluoro-phenyl)-2-oxo-1,2,3,4-tetrahydro-pyrimidine-5-carboxylic acid methyl ester;
(4S)4-(3,4-difluoro-phenyl)-3-[1-(4-hydroxy-4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester;
trans-4S-(3,4-difluorophenyl)-3-[1-(4-oxopyridin-2-yl-cyclohexyl)-3R-pyrrolidin-3-ylcarbamoyl]-6-methyl-2-oxo-1,2,3,4-tetrahydro-pyrimidine-5-carboxylic acid. methyl ester;
trans-2-(3,4-difluorophenyl)-1-[1-(4-pyridin-2-yl-cyclohexyl)-3R-pyrrolidin-3-ylcarbamoyl]-6-methoxymethyl-2-oxo-1,2,3,4-tetrahydro-pyrimidine;
and pharmaceutically acceptable salts thereof.

10. The compound of claim 8, which is Compound B:

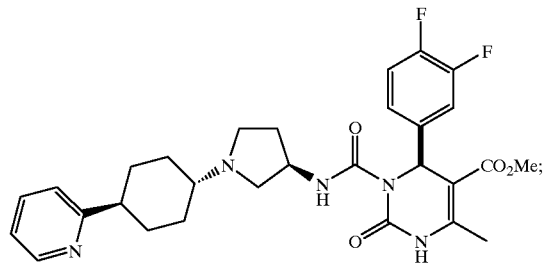

pharmaceutically acceptable salt thereof.

11. The compound of claim 8, which is Compound C:

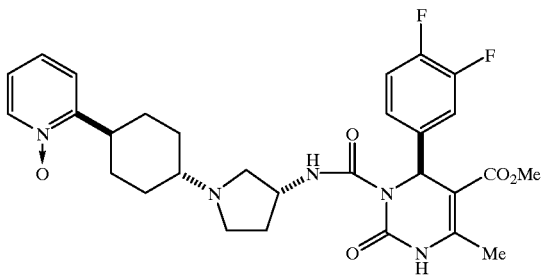

or a pharmaceutically acceptable salt thereof.

12. A pharmaceutical composition comprising the compound of claim 1 and a pharmaceutically acceptable carrier.

13. A pharmaceutical composition made by combining a compound of claim 1 and a pharmaceutically acceptable carrier.

14. A process for making a pharmaceutical composition comprising combining a compound of claim 1 and a pharmaceutically acceptable carrier.

15. The composition of claim 12 further comprising a testosterone 5-alpha reductase inhibitor.

16. The composition of claim 15, wherein the testosterone 5-alpha reductase inhibitor is a type 1, a type 2, both a type 1 and a type 2 or a dual type 1 and type 2 testosterone 5-alpha reductase inhibitor.

17. The composition of claim 16, wherein the testosterone 5-alpha reductase inhibitor is a type 2 testosterone 5-alpha reductase inhibitor.

18. The composition of claim 17, wherein the testosterone 5-alpha reductase inhibitor is finasteride.

19. A method of treating benign prostatic hyperplasia in a subject in need thereof which comprises administering to the subject a therapeutically effective amount of the compound of claim 1.

20. The method of claim 19, wherein the compound additionally does not cause a fall in blood pressure at dosages effective to alleviate benign prostatic hyperplasia.

21. The method of claim 19, wherein the compound is administered in combination with a testosterone 5-alpha reductase inhibitor.

22. The method of claim 21, wherein the testosterone 5-alpha reductase inhibitor is finasteride.

23. A method of treating benign prostatic hyperplasia in a subject in need thereof which comprises administering a therapeutically effective amount of the composition of claim 12.

24. The method of claim 23, wherein the composition further comprises a therapeutically effective amount of a testosterone 5-alpha reductase inhibitor.

25. A method of relaxing lower urinary tract tissue in a subject in need thereof which comprises administering to the subject a therapeutically effective amount of the compound of claim 1.

26. The method of claim 25, wherein the compound additionally does not cause a fall in blood pressure at dosages effective to relax lower urinary tract tissue.

27. The method of claim 25, wherein the compound is administered in combination with a testosterone 5-alpha reductase inhibitor.

28. The method of claim 27, wherein the testosterone 5-alpha reductase inhibitor is finasteride.

29. A method of treating a condition which is susceptible to treatment by antagonism of the alpha 1a receptor which comprises administering to a subject in need thereof an amount of the compound of claim 1 effective to treat the condition.

30. A method of eliciting an alpha 1a receptor antagonizing effect in a mammal in need thereof, comprising administering to the mammal a therapeutically effective amount of the compound of claim 1.

* * * * *